(12) United States Patent
Vidal Juan et al.

(10) Patent No.: US 8,258,122 B2
(45) Date of Patent: Sep. 4, 2012

(54) 3-([1,2,4]TRIAZOLO[4,3-A]PYRIDIN-7-YL) BENZAMIDE DERIVATIVES

(75) Inventors: Bernat Vidal Juan, St. Cebrià de Vallalta (ES); Paul Robert Eastwood, Rubi (ES); Jacob Gonzalez Rodriguez, Molins de Rei (ES); Cristina Esteve Trias, Barcelona (ES)

(73) Assignee: Almirall, S.A., Barcelona (ES)

( * ) Notice: Subject to any disclaimer, the term of this patent is extended or adjusted under 35 U.S.C. 154(b) by 195 days.

(21) Appl. No.: 12/529,490

(22) PCT Filed: Feb. 29, 2008

(86) PCT No.: PCT/EP2008/001616
§ 371 (c)(1),
(2), (4) Date: Sep. 1, 2009

(87) PCT Pub. No.: WO2008/107125
PCT Pub. Date: Sep. 12, 2008

(65) Prior Publication Data
US 2010/0120731 A1 May 13, 2010

(30) Foreign Application Priority Data

Mar. 2, 2007 (ES) .................................. 200700565

(51) Int. Cl.
| | |
|---|---|
| A61K 31/56 | (2006.01) |
| A61K 31/437 | (2006.01) |
| A61K 31/5377 | (2006.01) |
| A61K 31/506 | (2006.01) |
| C07D 471/04 | (2006.01) |
| C07D 413/14 | (2006.01) |
| C07D 401/14 | (2006.01) |
| A61P 37/02 | (2006.01) |
| A61P 19/02 | (2006.01) |
| A61P 25/00 | (2006.01) |
| A61P 9/00 | (2006.01) |
| A61P 1/00 | (2006.01) |

(52) U.S. Cl. ..................... 514/171; 514/303; 514/233.2; 514/256; 546/119; 544/127; 544/333

(58) Field of Classification Search .................. 546/119; 514/303, 256, 233.2, 171; 544/127, 333
See application file for complete search history.

(56) References Cited

U.S. PATENT DOCUMENTS

| | | | |
|---|---|---|---|
| 4,550,166 A | 10/1985 | Moran et al. | |
| 4,959,368 A | 9/1990 | Awaya et al. | |
| 5,414,088 A | 5/1995 | Von Der Saal et al. | |
| 6,586,447 B1 | 7/2003 | Lyssikatos et al. | |
| 8,106,190 B2 | 1/2012 | Kuramochi et al. | |
| 2003/0166724 A1 | 9/2003 | Hangeland | |
| 2005/0131014 A1 | 6/2005 | Collini et al. | |
| 2006/0106048 A1 | 5/2006 | Inoue et al. | |
| 2007/0213341 A1 | 9/2007 | Chen et al. | |
| 2008/0009486 A1 | 1/2008 | Chen et al. | |
| 2010/0130517 A1 | 5/2010 | Lumeras Amador et al. | |
| 2010/0227881 A1 | 9/2010 | Caturla Javaloyes et al. | |
| 2011/0046097 A1 | 2/2011 | Eastwood et al. | |
| 2011/0053936 A1 | 3/2011 | Eastwood et al. | |

FOREIGN PATENT DOCUMENTS

| | | |
|---|---|---|
| CN | 1502608 | 6/2004 |
| EP | 0 549 892 | 7/1993 |
| EP | 0 743 066 | 11/1996 |
| JP | 57-203068 | 12/1982 |
| JP | 10-79183 | 3/1989 |
| JP | 1996-005887 | 1/1996 |
| JP | 9-104638 | 4/1997 |
| WO | WO 87/04928 | 8/1987 |
| WO | WO 91/04974 | 4/1991 |
| WO | WO 91/06545 | 5/1991 |
| WO | WO 99/01449 A1 | 1/1999 |
| WO | WO 99/64400 | 12/1999 |
| WO | WO 00/63204 A1 | 10/2000 |
| WO | WO 00/66583 A2 | 11/2000 |

(Continued)

OTHER PUBLICATIONS

Redman et al., Bioorganic & medicinal chemistry letters, (Jan. 8, 2001) vol. 11, No. 1, pp. 9-12.*
Restriction Requirement dated Aug. 2, 2010 for U.S. Appl. No. 12/376,499.
Notice of Allowance dated Nov. 8, 2010 for U.S. Appl. No. 12/376,499.
Adams, R.H. et al. "Essential Role of p38α MAP Kinase in Placental but not Embryonic Cardiovascular Development," Molecular Cell, 6: 109-116 (2000).
Allen, M. et al. "Deficiency of the Stress Kinase p38α Results in Embryonic Lethality: Characterization of the Kinase Dependence of Stress Responses of Enzyme-deficient Embryonic Stem Cells," J. Exp. Med. 191(5): 859-869 (2000).

(Continued)

*Primary Examiner* — Niloofar Rahmani
(74) *Attorney, Agent, or Firm* — Finnegan, Henderson, Farabow, Garrett & Dunner, LLP

(57) ABSTRACT

New inhibitors of the p38 mitogen-activated protein kinase having the general formula (I) are disclosed herein, as well as processes for their preparation, pharmaceutical compositions comprising them, and their use in therapy.

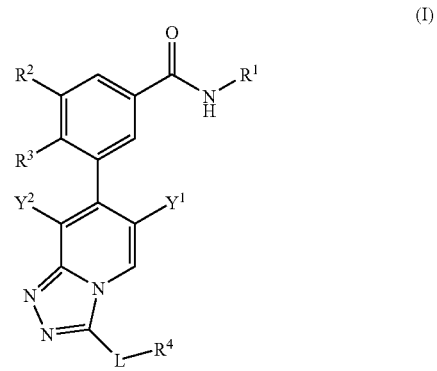

(I)

12 Claims, No Drawings

FOREIGN PATENT DOCUMENTS

| | | |
|---|---|---|
| WO | WO 01/01986 A1 | 1/2001 |
| WO | WO 01/29042 A1 | 4/2001 |
| WO | WO 02/02549 A1 | 1/2002 |
| WO | WO 02/46184 A1 | 6/2002 |
| WO | WO 02/058695 A1 | 8/2002 |
| WO | WO 02/072576 A1 | 9/2002 |
| WO | WO 02/072579 A1 | 9/2002 |
| WO | WO 03/008413 A1 | 1/2003 |
| WO | WO 03/033502 A1 | 4/2003 |
| WO | WO 03/043998 | 5/2003 |
| WO | WO 03/087087 A2 | 10/2003 |
| WO | WO 03/097062 A1 | 11/2003 |
| WO | WO 03/103590 A2 | 12/2003 |
| WO | WO 2004/010995 | 2/2004 |
| WO | WO 2004/010995 A1 | 2/2004 |
| WO | WO 2004/011470 | 2/2004 |
| WO | WO 2004/014900 A1 | 2/2004 |
| WO | WO 2004/020438 A2 | 3/2004 |
| WO | WO 2004/020440 A1 | 3/2004 |
| WO | WO 2004/074290 A1 | 9/2004 |
| WO | WO 2005/000232 | 1/2005 |
| WO | WO 2005/018624 A2 | 3/2005 |
| WO | WO 2005/032551 A1 | 4/2005 |
| WO | WO 2005/070929 | 8/2005 |
| WO | WO 2005/073219 A1 | 8/2005 |
| WO | WO 2005/121142 | 12/2005 |
| WO | WO 2007/063925 | 6/2007 |
| WO | WO 2007/098214 | 8/2007 |
| WO | WO 2007/104664 | 9/2007 |
| WO | WO 2008/017461 A1 | 2/2008 |
| WO | 2008045393 | * 4/2008 |
| WO | WO 2008/045393 | 4/2008 |
| WO | WO 2008/131922 | 11/2008 |
| WO | WO 2009/124692 | 10/2009 |
| WO | WO 2009/132774 | 11/2009 |
| WO | WO 2011/057757 | 5/2011 |

OTHER PUBLICATIONS

Amato, J.S. et al. "Synthesis of 1-*tert*-Butyl-4-chloropiperidine: Generation of an N-*tert*-Butyl Group by the Reaction of a Dimethyliminium Salt with Methylmagnesium Chloride," The Journal of Organic Chemistry, 70(5): 1930-1933 (2005).
Bao, J. et al. "p38 MAP kinase inhibitors: Metabolically stabilized piperidine-substituted quinolinones and naphthyridines," Bioorganic & Medicinal Chemistry Letters, 16: 64-68 (2006).
Beardmore, V.A. et al. "Generation and Characterization of p38β (MAPK11) Gene Targeted Mice," Molecular and Cellular Biology, 25(23): 10454-10464 (2005).
Brancho, D. et al. "Mechanism of p38 MAP kinase activation in vivo," Genes & Development, 17: 1969-1978 (2003).
Cheng, C. et al. "The Friedländer Synthesis of Quinolines," Organic Reactions, Chapter 2:37-201 (1982).
English Language Abstract for JP 57-203068 from esp@cenet, dated Dec. 13, 1982.
Gavrin, L.K. et al. "Inhibition of Tpl2 kinase and TNF-α production with 1,7-naphthyridine-3-carbonitriles: Synthesis and structure-activity relationships," Bioorganic & Medicinal Chemistry Letters, 15: 5288-5292 (2005).
Gilman, H. et al. "Some Substituted Isoquinolines," Journal of American Chemical Society, 69(8): 1946-1948 (1947).
Hale, K.K. et al. "Differential Expression and Activation of p38 Mitogen-Activated Protein Kinase α, β, γ, and δ in Inflammatory Cell Lineages," The Journal of Immunology, 162: 4246-4252 (1999).
Hideshima, T. et al. "Targeting p38 MAPK inhibits multiple myeloma cell growth in the bone marrow milieu," Blood, 101(2): 703-705 (2003).
Hildesheim, J. et al. "p38 Mitogen-Activated Protein Kinase Inhibitor Protects the Epidermis Against the Acute Damaging Effects of Ultraviolet Irradiation by Blocking Apoptosis and Inflammatory Responses," The Journal of Investigative Dermatology, 122:497-502 (2004).
Hollenbach, E. et al. "Inhibition of RICK/Nuclear Factor-κB and p38 Signaling Attenuates the Inflammatory Response in a Murine Model of Crohn Disease," The Journal of Biological Chemistry, 280(15): 14981-14988 (2005).
International Search Report mailed Oct. 18, 2007, for International Application No. PCT/EP2007/006981 (WO 2008/017461 A1).
Jin, S. et al. "p38 Mitogen-Activated Protein Kinase is Activated After a Spinal Nerve Ligation in Spinal Cord Microglia and Dorsal Root Ganglion Neurons and Contributes to the Generation of Neuropathic Pain," The Journal of Neuroscience, 23(10): 4017-4022 (2003).
Katsoulidis, E. et al. "Role of the p38 Mitogen-Activated Protein Kinase Pathway in Cytokine-Mediated Hematopoietic Suppression in Myelodysplastic Syndromes," Cancer Research, 65(19): 9029-9037 (2005).
Kotlyarov, A. et al. "MAPKAP Kinase 2 is essential for LPS-induced TNF-α biosynthesis," Nature Cell Biology, 1: 94-97 (1999).
Kumar, S. et al. "p38 Map Kinases: Key Signaling Molecules as Therapeutic Targets for Inflammatory Diseases," Nature Reviews Drug Discovery, 2: 717-726 (2003).
Kyriakis, J.M. et al. "Mammalian Mitogen-Activated Protein Kinase Signal Transduction Pathways Activated by Stress and Inflammation," Physiological Reviews, 81(2): 807-869 (2001).
Lee, J.C. et al. "A protein kinase involved in the regulation of inflammatory cytokine biosynthesis," Nature, 372(22/29): 739-746 (1994).
Miyaura, N. et al. "Palladium-Catalyzed Cross-Coupling Reactions of Organoboron Compounds," Chem. Rev., 95(7): 2457-2483 (1995).
Negishi, E. et al. "Novel Stereoselective Alkenyl-Aryl Coupling via Nickel-catalysed Reaction of Alkenylalanes with Aryl Halides," J.C.S. Chem. Comm., 596-597 (1976).
Nick, J.A. et al. "Selective Suppression of Neutrophil Accumulation in Ongoing Pulmonary Inflammation by Systemic Inhibition of p38 Mitogen-Activated Protein Kinase," The Journal of Immunology, 169: 5260-5269 (2002).
Pargellis, C. et al. "Inhibitors of p38 mitogen-activated protein kinase for the treatment of rheumatoid arthritis," Current Opinion in Investigational Drugs, 4(5): 566-571 (2003).
Sabio, G. et al. "p38γ regulates the localisation of SAP97 in the cytoskeleton by modulating its interaction with GKAP," The EMBO Journal, 24(6): 1134-1145 (2005).
Saccani, S. et al. "p38-dependent marking of inflammatory genes for increased NF-κB recruitment," Nature Immunology, 3(1): 69-75 (2002).
Schäfers, M. et al. "Tumor Necrosis Factor-α Induces Mechanical Allodynia After Spinal Nerve Ligation by Activation of p38 MAPK in Primary Sensory Neurons," The Journal of Neuroscience, 23(7): 2517-2521 (2003).
See, F. et al. "p38 MAP kinase as a therapeutic target in cardiovascular disease," Drug Discovery Today: Therapeutic Strategies, 1(2): 149-154 (2004).
Shi, Y. et al. "In the Cellular Garden of Forking Paths: How p38 MAPKs Signal for Downstream Assistance," Biol. Chem., 383: 1519-1536 (2002).
Tamura, K. et al. "Requirement for p38α in Erythropoietin Expression: A Role for Stress Kinases in Erythropoiesis," Cell, 102: 221-231 (2000).
Tsuda, M. et al. "Activation of p38 Mitogen-Activated Protein Kinase in Spinal Hyperactive Microglia Contributes to Pain Hypersensitivity Following Peripheral Nerve Injury," GLIA, 89:89-95 (2004).
Underwood, D.C. et al. "SB 239063, a p38 MAPK inhibitor, reduces neutrophilia, inflammatory cytokines, MMP-9, and fibrosis in lung," Am. J. Physiol. Lung Cell Mol. Physiol., 279: L895-L902 (2000).
Waetzig, G.H. et al. "p38 Mitogen-Activated Protein Kinase Is Activated and Linked to TNF-α Signaling in Inflammatory Bowel Disease," The Journal of Immunology, 168: 5342-5351 (2002).
Wang, X.S. et al. "Molecular Cloning and Characterization of a Novel p38 Mitogen-activated Protein Kinase," The Journal of Biological Chemistry, 272(38): 23668-23674 (1997).
U.S. Appl. No. 12/376,499, filed Feb. 5, 2009, Caturla Javaloyes et al.
Moran, D. B. et al., "Synthesis of (Pyridinyl)-1,2,4-triazolo[4,3-*a*]pyridines," J. Heterocyclic Chem., 23: 1071-1077 (1986).
International Search Report for PCT/EP2008/001616 dated May 28, 2008.
U.S. Appl. No. 12/597,187, filed Jan. 7, 2010, Wenceslao et al.
U.S. Appl. No. 12/936,784, filed Oct. 26, 2010, Eastwood et al.
U.S. Appl. No. 12/989,696, filed Oct. 26, 2010, Eastwood et al.

Balaban, A., "Aminyloxides (Nitroxides) from 1-Hydroxy-2-Indolinones," Tetrahedron, vol. 30, pp. 739-744 (1974).
Baxter, I. et al., "The Oxidation of 5-Arylsulphonamido-3,3-dimethyloxindoles and Related Compounds," Journal of the Chemical Society (C), pp. 952-955 (1971).
Dopp, D., "Substituenteneinflüsse auf die Photocyclisierung von 1-tert-Butyl-2-nitrobenzolen," Liebigs Annalen der Chemie, pp. 554-563 (1979).
English Language Abstract for JP 1996-005887 (2012).
English Language Abstract for JP 10-79183 (2012).
English Language Abstract for JP 09-104638 (2012).
English Language Abstract for WO 1987/04928 (2012).
English Language Abstract for WO 1991/04974 (2012).
English Language Abstract for WO 1991/06545 (2012).
English Language Abstract for WO 2004/011470 (2012).
English Language Abstract for WO 2007/063925 (2012).
Fang, C. et al., "Dimerization of a 3-Substituted Oxidindole at C-3 and Its Application to the Synthesis of (±)-Folicanthine," Journal of the American Chemical Society, 116: 9480-9486 (1994).
International Search Report for International Application No. PCT/EP2009/0002783 dated May 28, 2009.
International Search Report for International Application No. PCT/EP2009/002458 dated Jun. 3, 2009.
International Search Report mailed Aug. 12, 2008, for International Application No. PCT/EP2008/003357.
International Search Report mailed Nov. 9, 2010, for International Application No. PCT/EP2010/006817.
Karp, G. et al., "Preparation and Alkylation of Regioisomeric Tetrahydrophthalimide-Substituted Indolin-2(3H)-ones," Journal of Heterocyclic Chemistry, vol. 31, pp. 1513-1520 (1994).
Lee, H. et al., "Biochemical and Physiological Effects of Benzheterocycles and Related Compounds," Journal of Agricultural and Food Chemistry, vol. 43, pp. 2722-2727 (1995).
Lyga, J. et al., "Structural Replacements for the Benzoxazinone Protox Inhibitors," Pesticide Science, vol. 55, pp. 281-287 (1999).
Office Action dated Aug. 2, 2010 for U.S. Appl. No. 12/376,499.
Office Action dated Feb. 8, 2012 for U.S. Appl. No. 12/597,187.
Müller, C. et al., "Chiral Pyrrolo[2,3-d]pyrimidine and Pyrimido[4,5-b]indole Derivatives: Structure-Activity Relationships of Potent, Highly Stereoselective A1-Adenosine Receptor Antagonists," Journal of Medicinal Chemistry, vol. 39, pp. 2482-2491 (1996).
Patani et al., Bioisosterism: A Rational Approach in Drug Design, Chemical Reviews, ACS, vol. 96, No. 8, Jan. 1, 1996, pp. 3147-3176.
Santilli, A. et al., "7-Deazapurines V. Synthesis and Reactions of 7-Amino-5,7-dihydro-4-methyl-2-phenyl-6H-pyrrolo[2,3-d]pyrimidin-6-one," Journal of Heterocyclic Chemistry, vol. 12, pp. 1291-1293 (1975).
Wang, XS et al. "Molecular Cloning and Characterization of a Novel p38 Mitogen-activated Protein Kinase," The Journal of Biological Chemistry, 272(38): 23668-23674 (1997).
Zhou, et al. "TNFR-induced the NF-κB, but not the ERK, p38MAPK or JNK activation, mediates TNF-induced ICAM-1 and VCAM-1 expression on endothelial cells," Cellular Signalling, 19: 1238-1248 (2007).

* cited by examiner

3-([1,2,4]TRIAZOLO[4,3-A]PYRIDIN-7-YL) BENZAMIDE DERIVATIVES

This is a national stage filing under 35 U.S.C. §371 of International Application No. PCT/EP2008/001616, filed on Feb. 29, 2008, which claims priority to Spanish Patent Application No. P200700565, filed Mar. 2, 2007. The contents of both applications are incorporated herein by reference.

The present invention relates to new inhibitors of the p38 mitogen-activated protein kinase.

MAP kinases are evolutionary conserved enzymes translating membrane signals into gene expression responses. In mammals, four MAPK families can be distinguished: extracellular signal-related kinases (ERK1/2), Jun amino terminal kinases (JNK1/2/3), p38 proteins (alpha, beta, gamma and delta) and ERK5. The regulation of these proteins is exerted by a three-tier cascade composed of MAPK, MAPK kinase, and MAPK kinase kinase.

p38 MAPK was originally identified as the target of CSAIDs (cytokine suppressive anti-inflammatory drugs), having a central role in the signal transduction pathway leading to the production of TNF-alpha and other cytokines (Lee et al, 1984). p38 is activated by phosphorylation in Thr and Tyr by either MKK3, MKK4, or MKK6 (Kyriakis and Avruch, 2001) in response to stress and pro-inflammatory stimuli. In turn, p38 phosphorylates its effectors in Ser and Thr residues, namely protein kinases phosphatases and transcription factors, such as ATF-2, MEF2, MAPKAPK2, MSK1/2 or MNK1/2. Altogether this activation cascade results in control of gene expression through four different mechanisms: transcription factor activation; mRNA stabilization; mRNA translation; and histone phosphorylation at NF-kB binding sites in chromatin (Shi and Gaestel, 2002; Sacanni et al, 2001).

There are four different p38 isoforms encoded by separate genes: p38 alpha, beta, gamma and delta, each one showing a distinct tissue expression pattern. As assessed by mRNA and protein levels (Beardmore et al, 2005; Wang et al, 1997), p38 alpha and beta are ubiquitously expressed, with p38 beta expression being more relevant in CNS tissues (brain, cortex, cerebellum, hippocampus, etc). The expression of p38 gamma is more prominent in skeletal muscle while p38 delta localizes mainly in heart, kidney, lung and adrenal gland. At the cellular level, p38 alpha and delta seem to be the most relevant isoforms in immune cells (monocytes, macrophages, neutrophils and T cells) (Hale et al, 1999). Pharmacological inhibition with specific p38alpha/beta inhibitors as well as gene targeting studies have indicated that p38alpha is the isoform regulating inflammatory responses most probably through its downstream substrate MAPKAP-K2 (Kotlyarov et al, 1999). Likewise, this isoform is necessary in early embryonic development as p38alpha KO (knock-out) mice die in embryonic day 12.5 due to placental insufficiency and vascular defects (Allen et al, 2000; Tamura et al, 2000; Adams et al, 2000), a phenotype that is also reproduced in the MKK3/MKK6 double KO mice (Brancho et al, 2003). In contrast, p38 beta, gamma and delta knock-out mice do not show any developmental deficiencies (Beardmore et al, 2005; Sabio et al, 2005). p38 beta KO mice appear to respond similarly to pro-inflammatory stimuli (LPS) as wild type controls, indicating that this isoform does not have a role in inflammation (Beardmore et al 2005).

The contribution of the p38MAPK pathway to inflammation has been studied both in vitro and in vivo by employing different chemical series of p38 inhibitors (Pargellis and Regan, 2003; Kumar et al, 2003). The most widely used inhibitor molecule, SB203580, is, in fact, a dual p38alpha/beta inhibitor. Inhibition of p38 abrogates the release of TNF-alpha as well as other pro-inflammatory cytokines like IL-1, IL-6, and IL-8, in PBMC, whole blood, or the human monocytic cell line THP-1.

By virtue of the involvement of p38 in TNFalpha production, inhibitors of p38 have been tested in animal models of diseases in which TNFalpha has a pathophysiological role. p38 inhibition decreases murine collagen-induced arthritis and rat adjuvant-induced arthritis severity (Pargellis and Regan, 2003). Furthermore, p38 inhibitors also improve bone resorption in animal models of arthritis, probably due to the implication of p38 MAPK in the differentiation of osteoclasts. p38 inhibition attenuates the inflammatory response in a murine model of Crohn's disease and diminishes TNF-alpha production in human Crohn's disease patient biopsies (Hollenbach et al 2005; Waetzig et al, 2002). Due to the exclusive usage of the p38 pathway by neutrophils, p38 has also been considered a target for chronic obstructive pulmonary disease (COPD) (Nick et al, 2002). p38 inhibition reduces neutrophilia, inflammatory cytokines, MMP-9 and fibrosis in lung (Underwood et al, 2000). In skin models of irradiation, inhibition of p38 protects the epidermis against acute ultraviolet radiation exposure by blocking apoptosis and inflammatory responses (Hildesheim et al, 2004). p38 inhibition also reverses hematopoietic defects in bone marrow from patients with myelodysplastic syndromes, in which TNF-alpha overproduction has a pathophysiological role (Katsoulidis et al, 2005).

In hematopoietic malignancies, a study has shown that p38 inhibitors can block the proliferation of multiple myeloma cells by inhibiting the production of IL-6 and VEGF in bone marrow stromal cells (Hideshima et al, 2002).

p38 is involved in key cellular mechanisms such as apoptosis, fibrosis and cellular hypertrophy, which are common to cardiac and vascular pathologies. Pharmacological inhibition of p38 has proven useful in improving ischemia-reperfusion injury, cerebral focal ischemia, acute coronary syndrome, chronic heart failure and post-myocardial infarction remodelling (See et al, 2004).

Experimental inhibition of p38 has been reported effective in reducing pain in animal models of neuropathy that rely on COX-2 expression and TNF-alpha production by glial cells (Schafers et al, 2003; Jin et al, 2003; Tsuda et al, 2004).

Therefore, the compounds of the invention may be useful in the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, immune and inflammatory diseases, destructive bone disorders, neoplastic disorders, neurodegenerative disorders, viral diseases, infectious diseases, cardiovascular diseases, angiogenesis-related disorders, and pain-related disorders.

Autoimmune diseases which may be prevented or treated include but are not limited to rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease.

Immune and inflammatory diseases which may be prevented or treated include but are not limited to asthma, COPD, respiratory distress syndrome, acute or chronic pancreatitis, graft versus-host disease, Behcet syndrome, inflammatory eye conditions such as conjunctivitis and uveitis, psoriasis, contact dermatitis, atopic dermatitis, sarcoidosis, gout, pyresis, transplant rejection, allergic rhinitis, allergic conjunctivitis, Cardiovascular diseases which may be prevented or treated include but are not limited to ischemia-reperfusion injury, cerebral focal ischemia, acute coronary syndrome, congestive heart failure, cardiomyopathy, myocarditis, atherosclerosis, vasculitis and restenosis.

Destructive bone disorders which may be prevented or treated include but are not limited to osteoporosis, osteoarthritis and multiple myeloma-related bone disorder.

Neoplastic disorders which may be prevented or treated include but are not limited to solid tumors such as Kaposi's sarcoma, metastatic melanoma, and hematopoietic malignancies such as acute or chronic myelogenous leukemia and multiple myeloma.

Neurodegenerative diseases which may be prevented or treated include but are not limited to Parkinson's disease, Alzheimer's disease, neurodegenerative disease caused by traumatic injury, or Huntington's disease.

Viral diseases which may be prevented or treated include but are not limited to acute hepatitis infection (including hepatitis A, hepatitis B and hepatitis C), HIV infection, Epstein-Barr infection, CMV retinitis, SARS or avian influenza A infection.

Infectious diseases which may be prevented or treated include but are not limited to sepsis, septic shock, endotoxic shock, Gram negative sepsis, toxic shock syndrome, Shigellosis, or cerebral malaria.

Angiogenesis-related disorders which may be prevented or treated include but are not limited to hemangiomas, ocular neovascularization, macular degeneration or diabetic retinopathy.

Pain-related disorders which may be prevented or treated include but are not limited to neuropathic pain (such as diabetic neuropathy, post-herpetic or trigeminal neuralgia), cancer-related pain, chronic pain (such as lower back pain syndrome), and inflammatory pain.

Other miscellaneous diseases or disorders which may be prevented or treated include but are not limited to myelodysplastic syndrome, cachexia, endometriosis, acute skin injuries such as sunburn, and wound healing.

In view of the physiological effects mediated by inhibition of the p38 mitogen-activated protein kinase, several compounds have been recently disclosed for the treatment or prevention of rheumatoid arthritis, ischemia-reperfusion injury, cerebral focal ischemia, acute coronary syndrome, COPD, Crohn's disease, irritable bowel syndrome, adult respiratory distress syndrome, osteoporosis, neurodegenerative diseases such as Alzheimer's disease, rheumatoid spondylitis, psoriasis, atherosclerosis, osteoarthritis, multiple myeloma. See for example WO 99/01449, WO 00/63204, WO 01/01986, WO 01/29042, WO 02/046184, WO 02/058695, WO 02/072576, WO 02/072579, WO 03/008413, WO 03/033502, WO 03/087087, WO 03/097062, WO 03/103590, WO 2004/010995, WO 2004/014900, WO 2004/020438, WO 2004/020440, WO 2005/018624, WO 2005/032551, WO 2005/073219.

It has now been found that certain 3-([1,2,4]triazolo[4,3-a]pyridin-7-yl)benzamide derivatives are novel potent inhibitors of the p38 mitogen-activated protein kinase and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by inhibition of the p38 mitogen-activated protein kinase; and methods of treatment of pathological conditions or diseases susceptible to amelioration by inhibition of the p38 mitogen-activated protein kinase comprising the administration of the compounds of the invention to a subject in need of treatment.

Thus, the present invention is directed to new 3-([1,2,4]triazolo[4,3-a]pyridin-7-yl)benzamide derivatives of formula (I)

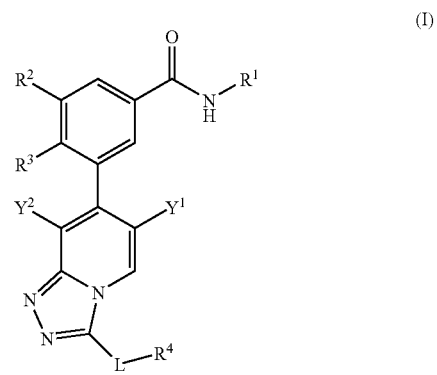

wherein
$R^1$ is selected from the group consisting of $C_{1-4}$ alkyl group, $C_{3-7}$ cycloalkyl and $-(CH_2)_{(1-3)}-C_{3-7}$ cycloalkyl, $R^2$ is selected from the group consisting of hydrogen atoms and halogen atoms $R^3$ is selected from the group consisting of methyl groups and halogen atoms L is selected from the group consisting of a direct bond, —$(CR_aR_b)_{(1-2)}$—, —CO—, —S—, —O—, —$(CR_aR_b)_{(0-1)}$—NH—CO—, —CO—NH—$(CR_aR_b)_{(0-1)}$—, —$(CR_aR_b)_{(0-1)}$—NH—$SO_2$—, —$(CR_aR_b)_{(0-1)}$—$N(R^5)$— and —$N(R^5)$—$(CR_aR_b)_{(0-1)}$—; wherein $R_a$, $R_b$ and $R^5$ independently are selected from the group consisting of hydrogen atoms and $C_{1-4}$ alkyl groups, $R^4$ is selected from the group consisting of hydrogen atoms, hydroxy, $C_{1-4}$ alkoxy groups, $C_{1-4}$ alkyl groups optionally substituted with fluorine atoms, $C_{3-6}$ cycloalkyl optionally substituted with fluorine atoms or $C_{1-4}$ alkyl groups, $C_{5-14}$ aryl groups which are optionally substituted with halogen atoms or with groups selected from $C_{1-4}$ alkyl, trifluoromethyl and difluoromethyl, or 5 to 14-membered heteroaryl groups containing at least one heteroatom selected from N, O and S, which heteroaryl groups are optionally substituted with halogen atoms or with groups selected from $C_{1-4}$ alkyl, trifluoromethyl and difluoromethyl; or 3 to 7-membered heterocyclic groups containing at least one heteroatom selected from N, O and S, which heterocyclic groups are optionally substituted with $C_{1-4}$ alkyl groups;

$Y^1$ and $Y^2$ are independently selected from the group consisting of hydrogen atoms, fluorine and chlorine atoms and pharmaceutically acceptable salts and N-oxides thereof.

As used herein the term $C_{1-4}$ alkyl embraces optionally substituted, linear or branched hydrocarbon radicals having 1 to 4 carbon atoms. Preferred substituents on the alkyl groups are halogen atoms and hydroxy groups.

Examples include methyl, ethyl, n-propyl, i-propyl, n-butyl, sec-butyl and tert-butyl radicals.

As used herein the term $C_{1-4}$ alkoxy embraces optionally substituted, linear or branched hydrocarbon radicals having 1 to 4 carbon atoms. Examples include methoxy, ethoxy, n-propoxy, i-propoxy, n-butoxy, sec-butoxy and t-butoxy.

As used herein, the term cycloalkyl embraces saturated carbocyclic radicals and, unless otherwise specified, a cycloalkyl radical typically has from 3 to 7 carbon atoms, preferably from 3 to 5 carbon atoms and more preferably from 3 to 4 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and methyl groups.

As used herein, the term aryl radical embraces typically a $C_5$-$C_{14}$ monocyclic or polycyclic aryl radical such as phenyl or naphthyl, anthranyl or phenanthryl. Phenyl is preferred. When an aryl radical carries 2 or more substituents, the substituents may be the same or different.

As used herein, the term heteroaryl radical embraces typically a 5 to 14 membered ring system comprising at least one heteroaromatic ring and containing at least one heteroatom selected from O, S and N. A heteroaryl radical may be a single ring or two or more fused rings wherein at least one ring contains a heteroatom. Preferably a heteroaryl radical is a 5 or 6 membered single ring.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl and pyrazolyl radicals. Pyridyl, thienyl, furanyl, pyridazinyl, pyrimidinyl and quinolyl radicals are preferred.

When a heteroaryl radical carries 2 or more substituents, the substituents may be the same or different.

As used herein, the term heterocyclic group embraces typically a saturated or unsaturated, non-aromatic, $C_3$-$C_7$ carbocyclic ring, such as a 5, 6 or 7 membered radical, in which one or more, for example 1, 2, or 3 of the carbon atoms preferably 1 or 2 of the carbon atoms are replaced by a heteroatom selected from N, O and S. Saturated heterocyclyl radicals are preferred. A heterocyclic radical may be a single ring or two or more fused rings wherein at least one ring contains a heteroatom. When a heterocyclyl radical carries 2 or more substituents, the substituents may be the same or different.

Examples of heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl. Where a heterocyclyl radical carries 2 or more substituents, the substituents may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

In one embodiment of the present invention, -L-$R^4$ represents a saturated nitrogen-containing, 3-7 membered heterocyclic ring linked to the carbon atom of the triazolo ring through a nitrogen atom, which 3-7 membered heterocyclic ring comprises 1 or 2 nitrogen atoms and 0 or 1 oxygen atoms and is optionally substituted with $C_{1-4}$ alkyl groups. More preferably -L-$R^4$ represents a 5 or 6 membered heterocyclic ring, for example 3-morpholin-4-yl or pyrrolidinyl.

Typically, when L is a direct bond and $R^4$ is a heterocyclic ring, the heterocyclic ring is preferably a saturated nitrogen-containing, 3-7 membered heterocyclic ring linked to the carbon atom of the triazolo ring through a nitrogen atom, which 3-7 membered heterocyclic ring comprises 1 or 2 nitrogen atoms and 0 or 1 oxygen atoms and is optionally substituted with $C_{1-4}$ alkyl groups.

In one embodiment of the present invention, $R^1$ is selected from the group consisting of $C_{1-4}$ alkyl group, $C_{3-7}$ cycloalkyl and —$(CH_2)_{(1-3)}$—$C_{3-7}$cycloalkyl), $R^2$ is selected from the group consisting of hydrogen atoms and halogen atoms, $R^3$ is selected from the group consisting of methyl groups and halogen atoms, L is selected from the group consisting of —$(CH_2)_{(0-2)}$—, —S—, —O— and —$NR^5$—$(CH_2)_{0-1}$—; wherein $R^5$ is selected from the group consisting of hydrogen atoms and $C_{1-4}$ alkyl groups, $R^4$ is selected from the group consisting of hydrogen atoms, $C_{1-4}$ alkyl groups optionally substituted with fluorine atoms, $C_{3-6}$ cycloalkyl optionally substituted with fluorine atoms or $C_{1-4}$ alkyl groups, $C_{5-6}$ aryl groups which are optionally substituted with halogen atoms or with groups selected from $C_{1-4}$ alkyl, trifluoromethyl and difluoromethyl or 5 to 14-membered heteroaryl groups containing at least one heteroatom selected from N, O and S, which heteroaryl groups are optionally substituted with halogen atoms or with groups selected from $C_{1-4}$ alkyl, trifluoromethyl and difluoromethyl; or -L-$R^4$ represents a saturated, nitrogen-containing, 3-7 membered heterocyclic ring linked to the carbon atom of the triazolo ring through a nitrogen atom, which 3-7 membered heterocyclic ring comprises 1 or 2 nitrogen atoms and 0 or 1 oxygen atoms and is optionally substituted with $C_{1-4}$ alkyl groups; and $Y^1$ and $Y^2$ are independently selected from the group consisting of hydrogen atoms, fluorine and chlorine atoms Typically $R^1$ is selected from the group consisting of $C_{3-6}$ cycloalkyl and —$(CH_2)_{(1-3)}$—$C_{3-6}$ cycloalkyl. Preferably $R^1$ represents a $C_{3-4}$ cycloalkyl. More preferably $R^1$ represents a cyclopropyl group.

Typically $R^2$ represents a hydrogen atom or a fluorine atom.

Typically $R^3$ is a methyl group

In a preferred embodiment of the present invention, L is a direct bond and $R^4$ is selected from the group consisting of $C_{1-4}$ alkyl groups, $C_{3-6}$ cycloalkyl optionally substituted with a methyl group and a $C_{5-6}$ aryl group which is optionally substituted with halogen atoms. Preferably $R^4$ is selected from the group consisting of branched $C_{3-4}$ alkyl groups and a phenyl group which is optionally substituted with a chlorine or fluorine atoms.

For the avoidance of doubt, the orientation of the L moiety is such that the left-hand side of the L moiety depicted is attached to triazolio ring and the right-hand side of the L moiety depicted is attached to $R^4$.

Typically, when $R^4$ is hydrogen, L is other than —CO—, —NHCO— or —$(CR_aR_b)_{(0-1)}$—NH—$SO_2$—. Preferably when $R^4$ is hydrogen, L is —CONH— or —$(CR_aR_b)_{(0-1)}$—$N(R^5)$—.

Typically, $Y^1$ and $Y^2$ are independently selected from the group consisting of hydrogen atom and fluorine atom.

In yet a preferred embodiment of the present invention, $R^1$ represents a cyclopropyl group, $R^2$ is selected from hydrogen atom and fluorine atom, $R^3$ represents a methyl group, L is a direct bond, $R^4$ is selected from the group consisting of branched $C_{3-4}$ alkyl groups or a phenyl group which is optionally substituted with a chlorine or fluorine atoms and $Y^1$ and $Y^2$ are independently selected from the group consisting of hydrogen atom and fluorine atom.

Particular individual compounds of the invention include:

3-(3-tert-Butyl-[1,2,4]triazolo[4,3-a]pyridin-7-yl)-N-cyclopropyl-4-methylbenzamide N-Cyclopropyl-3-(3-isopropyl-[1,2,4]triazolo[4,3-a]pyridin-7-yl)-4-methylbenzamide N-Cyclopropyl-3-(3-cyclopropyl-[1,2,4]triazolo[4,3-a]pyridin-7-yl)-4-methylbenzamide N-Cyclopropyl-4-methyl-3-(3-(1-methylcyclopropyl)-[1,2,4]triazolo[4,3-a]pyridin-7-yl)benzamide 3-(3-Cyclobutyl-[1,2,4]triazolo[4,3-a]pyridin-7-yl)-N-cyclopropyl-4-methylbenzamide 3-(3-(2-Chlorophenyl)-[1,2,4]triazolo[4,3-a]pyridin-7-yl)-N-cyclopropyl-4-methylbenzamide N-Cyclopropyl-3-(3-(cyclopropylmethylamino)-[1,2,4]triazolo[4,3-a]pyridin-7-yl)-4-methylbenzamide 3-(3-tert-Butyl-[1,2,4]triazolo[4,3-a]pyridin-7-yl)-N-(cyclopropylmethyl)-4-methylbenzamide 3-(3-tert-Butyl-[1,2,4]triazolo[4,3-a]pyridin-7-yl)-N-cyclopropyl-5-fluoro-4-methylbenzamide 3-(3-tert-Butyl-[1,2,4]triazolo[4,3-a]pyridin-7-yl)-4-chloro-N-cyclopropylbenzamide N-Cyclopropyl-3-[3-(2-fluorophenyl)-[1,2,4]triazolo[4,3-a]pyridin-7-yl]-4-methyl-benzamide N-Cyclopropyl-3-[3-(2,6-difluorophenyl)-[1,2,4]triazolo[4,3-a]pyridin-7-yl]-4-methylbenzamide N-Cyclopropyl-3-[3-(2,6-dichlorophenyl)-[1,2,4]triazolo[4,3-a]pyridin-7-yl]-4-methylbenzamide N-Cyclopropyl-3-[3-(2,6-dichlorophenyl)-[1,2,4]triazolo[4,3-a]pyridin-7-yl]-5-fluoro-4-methylbenzamide N-Cyclopropyl-4-methyl-3-(3-morpholin-[1,2,4]triazolo[4,3-a]pyridin-7-yl)-benzamide N-Cyclopropyl-4-methyl-3-(3-pyrrolidin-[1,2,4]triazolo[4,3-a]pyridin-7-yl)-benzamide N-Cyclopropyl-3-[3-(cyclopropylmethylamino)-[1,2,4]triazolo[4,3-a]pyridin-7-yl]-5-fluoro-4-methylbenzamide 3-(3-tert-Butyl-6-fluoro-[1,2,4]triazolo[4,3-a]pyridin-7-yl)-N-cyclopropyl-4-methylbenzamide 3-(3-tert-Butyl-6-fluoro-[1,2,4]triazolo[4,3-a]pyridin-7-yl)-N-cyclopropyl-5-fluoro-4-methylbenzamide 3-(3-tert-Butyl-6,8-difluoro-[1,2,4]triazolo[4,3-a]pyridin-7-yl)-N-cyclopropyl-4-methylbenzamide 3-(3-tert-Butyl-6,8-difluoro-[1,2,4]triazolo[4,3-a]pyridin-7-yl)-N-cyclopropyl-5-fluoro-4-methylbenzamide N-Cyclopropyl-3-(6,8-difluoro-3-isopropyl[1,2,4]triazolo[4,3-a]pyridin-7-yl)-5-fluoro-4-methylbenzamide N-cyclopropyl-3-(3-cyclopropyl-6,8-difluoro[1,2,4]triazolo[4,3-a]pyridin-7-yl)-5-fluoro-4-methylbenzamide
3-(3-(2-Chlorophenyl)-[1,2,4]triazolo[4,3-a]pyridin-7-yl)-N-cyclopropyl-5-fluoro-4-methylbenzamide
3-[3-(3-Chloropyridin-4-yl)-6,8-difluoro[1,2,4]triazolo[4,3-a]pyridin-7-yl]-N-cyclopropyl-5-fluoro-4-methylbenzamide
N-Cyclopropyl-3-[6,8-difluoro-3-(2-methylpyridin-3-yl)[1,2,4]triazolo[4,3-a]pyridin-7-yl]-5-fluoro-4-methylbenzamide
N-cyclopropyl-3-(3-cyclopropyl[1,2,4]triazolo[4,3-a]pyridin-7-yl)-5-fluoro-4-methylbenzamide
N-cyclopropyl-3-fluoro-5-(3-isopropyl[1,2,4]triazolo[4,3-a]pyridin-7-yl)-4-methylbenzamide
3-(3-Cyclobutyl[1,2,4]triazolo[4,3-a]pyridin-7-yl)-N-cyclopropyl-5-fluoro-4-methylbenzamide
3-[3-(3-Chloropyridin-4-yl)[1,2,4]triazolo[4,3-a]pyridin-7-yl]-N-cyclopropyl-4-methylbenzamide
3-[3-(3-Chloropyridin-4-yl)[1,2,4]triazolo[4,3-a]pyridin-7-yl]-N-cyclopropyl-5-fluoro-4-methylbenzamide
N-Cyclopropyl-4-methyl-3-[3-(tetrahydro-2H-pyran-4-yl)[1,2,4]triazolo[4,3-a]pyridin-7-yl]benzamide
N-Cyclopropyl-3-fluoro-4-methyl-5-[3-(tetrahydro-2H-pyran-4-yl)[1,2,4]triazolo[4,3-a]pyridin-7-yl]benzamide
3-[3-(1-Amino-1-methylethyl)[1,2,4]triazolo[4,3-a]pyridin-7-yl]-N-cyclopropyl-4-methylbenzamide
3-[3-(1-Amino-1-methylethyl)[1,2,4]triazolo[4,3-a]pyridin-7-yl]-N-cyclopropyl-5-fluoro-4-methylbenzamide
N-Cyclopropyl-3-[3-(1-methoxy-1-methylethyl)[1,2,4]triazolo[4,3-a]pyridin-7-yl]-5-fluoro-4-methylbenzamide
3-(3-Cyclohexyl[1,2,4]triazolo[4,3-a]pyridin-7-yl)-N-cyclopropyl-5-fluoro-4-methylbenzamide
N-Cyclopropyl-3-{3-[(1S)-1-methoxyethyl][1,2,4]triazolo[4,3-a]pyridin-7-yl}-4-methylbenzamide
N-Cyclopropyl-3-fluoro-5-{3-[(1S)-1-methoxyethyl][1,2,4]triazolo[4,3-a]pyridin-7-yl}-4-methylbenzamide
N-Cyclopropyl-3-fluoro-4-methyl-5-[3-(trifluoromethyl)[1,2,4]triazolo[4,3-a]pyridin-7-yl]benzamide
3-{3-[1-(Acetylamino)-1-methylethyl][1,2,4]triazolo[4,3-a]pyridin-7-yl}-N-cyclopropyl-5-fluoro-4-methylbenzamide
N-Cyclopropyl-3-fluoro-4-methyl-5-[3-(pyrrolidin-1-ylcarbonyl)[1,2,4]triazolo[4,3-a]pyridin-7-yl]benzamide
N-Cyclopropyl-3-{3-[1-(dimethylamino)-1-methylethyl][1,2,4]triazolo[4,3-a]pyridin-7-yl}-5-fluoro-4-methylbenzamide
N-Cyclopropyl-3-fluoro-4-methyl-5-(3-{1-methyl-1-[(methylsulfonyl)amino]ethyl}[1,2,4]triazolo[4,3-a]pyridin-7-yl)benzamide
N-Cyclopropyl-3-fluoro-5-[3-(1-hydroxy-1-methylethyl)[1,2,4]triazolo[4,3-a]pyridin-7-yl]-4-methylbenzamide
3-{3-(1-Amino-1-methylethyl)-6,8-difluoro[1,2,4]triazolo[4,3-a]pyridin-7-yl}-N-cyclopropyl-5-fluoro-4-methylbenzamide
N-Cyclopropyl-3-{3-[1-(dimethylamino)-1-methylethyl]-6,8-difluoro[1,2,4]triazolo[4,3-a]pyridin-7-yl}-5-fluoro-4-methylbenzamide
N-Cyclopropyl-3-fluoro-4-methyl-5-[3-(1-methylcyclopropyl)[1,2,4]triazolo[4,3-a]pyridin-7-yl]benzamide
N-Cyclopropyl-3-fluoro-4-methyl-5-[3-(2,2,2-trifluoro-1,1-dimethylethyl)[1,2,4]triazolo-[4,3-a]pyridin-7-yl]benzamide
N-Cyclopropyl-4-methyl-3-(3-pyrimidin-5-yl[1,2,4]triazolo[4,3-a]pyridin-7-yl)benzamide
N-Cyclopropyl-4-methyl-3-[3-(trifluoromethyl)[1,2,4]triazolo[4,3-a]pyridin-7-yl]benzamide
N-Cyclopropyl-3-fluoro-4-methyl-5-(3-pyrimidin-5-yl[1,2,4]triazolo[4,3-a]pyridin-7-yl)benzamide
7-{5-[(Cyclopropylamino)carbonyl]-3-fluoro-2-methylphenyl}[1,2,4]triazolo[4,3-a]pyridine-3-carboxamide Of outstanding interest are:

3-(3-tert-Butyl-[1,2,4]triazolo[4,3-a]pyridin-7-yl)-N-cyclopropyl-4-methylbenzamide
N-Cyclopropyl-3-(3-isopropyl-[1,2,4]triazolo[4,3-a]pyridin-7-yl)-4-methylbenzamide
3-(3-(2-Chlorophenyl)-[1,2,4]triazolo[4,3-a]pyridin-7-yl)-N-cyclopropyl-4-methylbenzamide
3-(3-tert-Butyl-[1,2,4]triazolo[4,3-a]pyridin-7-yl)-N-cyclopropyl-5-fluoro-4-methylbenzamide
N-Cyclopropyl-3-[3-(2-fluorophenyl)-[1,2,4]triazolo[4,3-a]pyridin-7-yl]-4-methyl-benzamide
3-(3-tert-Butyl-6-fluoro-[1,2,4]triazolo[4,3-a]pyridin-7-yl)-N-cyclopropyl-4-methylbenzamide
3-(3-tert-Butyl-6-fluoro-[1,2,4]triazolo[4,3-a]pyridin-7-yl)-N-cyclopropyl-5-fluoro-4-methylbenzamide
3-(3-tert-Butyl-6,8-difluoro-[1,2,4]triazolo[4,3-a]pyridin-7-yl)-N-cyclopropyl-4-methylbenzamide
3-(3-tert-Butyl-6,8-difluoro-[1,2,4]triazolo[4,3-a]pyridin-7-yl)-N-cyclopropyl-5-fluoro-4-methylbenzamide
N-Cyclopropyl-3-(6,8-difluoro-3-isopropyl[1,2,4]triazolo[4,3-a]pyridin-7-yl)-5-fluoro-4-methylbenzamide
3-(3-(2-Chlorophenyl)-[1,2,4]triazolo[4,3-a]pyridin-7-yl)-N-cyclopropyl-5-fluoro-4-methylbenzamide
N-cyclopropyl-3-fluoro-5-(3-isopropyl[1,2,4]triazolo[4,3-a]pyridin-7-yl)-4-methylbenzamide According to a further feature of the present invention, compounds of general formula (I) are prepared following the synthetic scheme illustrated in FIG. 1.

The 3-([1,2,4]triazolo[4,3-a]pyridin-7-yl)benzamide derivatives of formula (I) can be converted by methods known per se into pharmaceutically acceptable salts or N-oxides. Preferred salts are acid addition salts obtainable by treatment with organic or inorganic acids such as fumaric, tartaric, succinic or hydrochloric acid.

The compounds of the present invention may be prepared by methods such as those illustrated in the following Schemes. Solvents, temperatures, pressures and other reaction conditions may readily be selected by one of ordinary skill in the art. Starting materials are commercially available or can be readily prepared by one of ordinary skill in the art using known methods. For all the schemes and compounds described below, $R^1$, $R^2$, $R^3$, L, $R^4$, $R^5$, $Y^1$ and $Y^2$ are as described for a compound of general formula (I).

According to a further feature of the present invention, compounds of general formula (I) can be prepared by a coupling reaction between a 7-halo[1,2,4]triazolo[4,3-a]pyridine of formula (III), wherein $X^1$ represents an iodine, bromine or hydrogen atom, and a borolane derivative (IIA), boronic acid (IIB), or an aromatic iodine derivative (IIC) as shown in FIG. 1.

FIG. 1

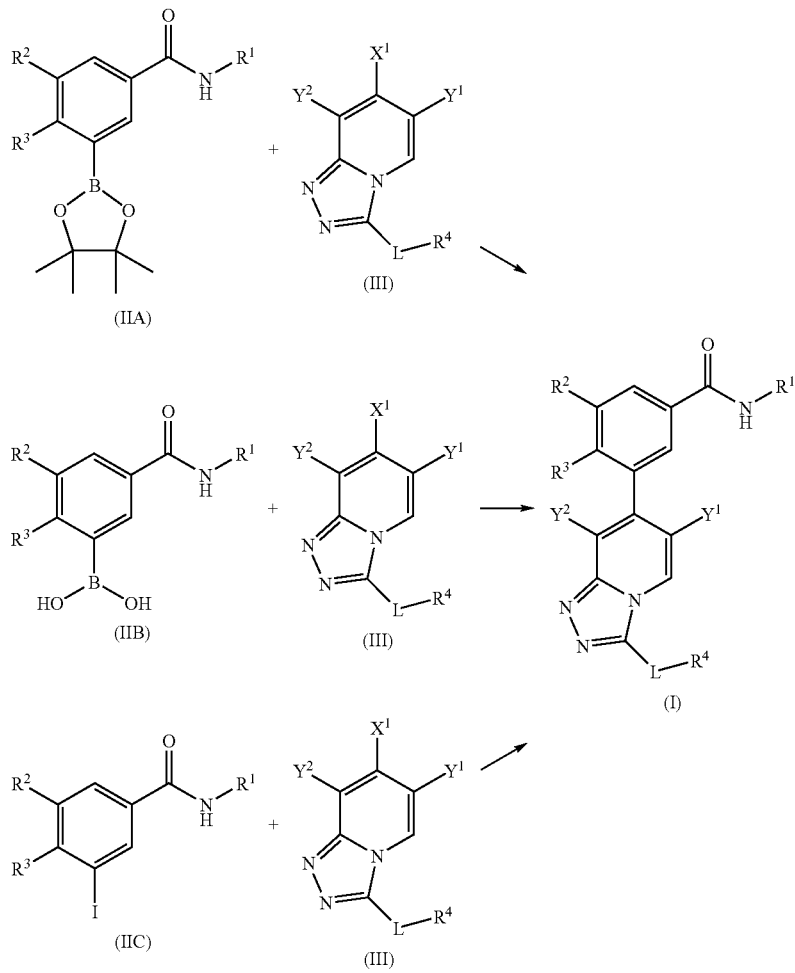

Compounds of general formula (I) can be prepared by reacting a compound of formula (IIA) or (IIB) with a compound of general formula (III) using typical Suzuki-Miyaura reaction conditions (Miyaura, N.; Suzuki, A. *Chem. Rev.* 1995, 95, 2457) such as in the presence of tetrakis(triphenylphosphine)palladium(0) or [1,1'-bis(diphenylphosphino)ferrocene] palladium(II) dichloride dichloromethane complex (1:1) in solvents such as toluene or dioxane in an aqueous solution of a base such as sodium or cesium carbonate.

In the particular case, wherein $Y^1$ and $Y^2$ are fluorine atoms, compounds of general formula (IA), may also be prepared as shown in FIG. 2.

FIG. 2

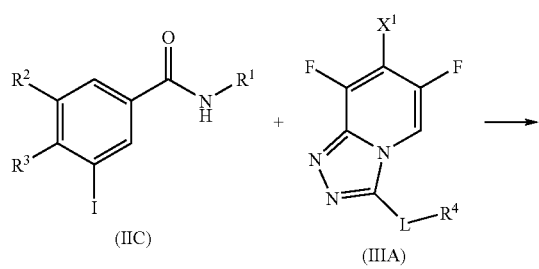

-continued

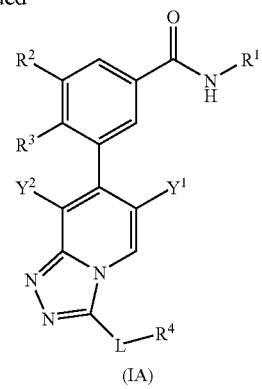

compounds of general formula (IA), may be obtained by reacting a compound of formula (IIIA), wherein $X^1$, L and $R^4$ are as defined above, with a base such as butyl lithium or lithium bis(trimethylsilyl)amide and then with zinc chloride in tetrahydrofuran to generate an organozinc compound that would react with a compound of general formula (IIC) using typical Negishi reaction conditions (Negishi, E.-I.; Liu, F. In Metal-Catalyzed Cross-Coupling Reactions; 1998, Diederich, F.; Stang, P. J. eds.; Wiley-VCH Verlag GmbH: Weinheim, Germany, pp 1-47) such as in the presence of tetrakis (triphenylphosphine) palladium(0) or [1,1'-bis(diphenylphosphino)-ferrocene] palladium(II) dichloride dichloromethane complex (1:1) or tris(dibenzylidene-acetone)dipalladium(0) with the use of a ligand such as XANTPHOS or 1,1'-bis(diphenyl-phosphino)ferrocene in tetrahydrofuran.

Compounds of formula (IIA) and (IIB) may be prepared following the general synthetic procedures disclosed in FIG. 3.

amine compound of formula $R^1$—$NH_2$ (XI) in which $R^1$ is as hereinbefore defined, under amide forming conditions.

Suitable amide forming conditions are well known in the art and include treating a solution of the acid of formula (X) or the activated form thereof, in for example DMF, with an amine of formula (XI) in the presence of a base such as triethylamine.

Compounds of general formula (X) are commercially available or can be prepared by direct halogenation of a com-

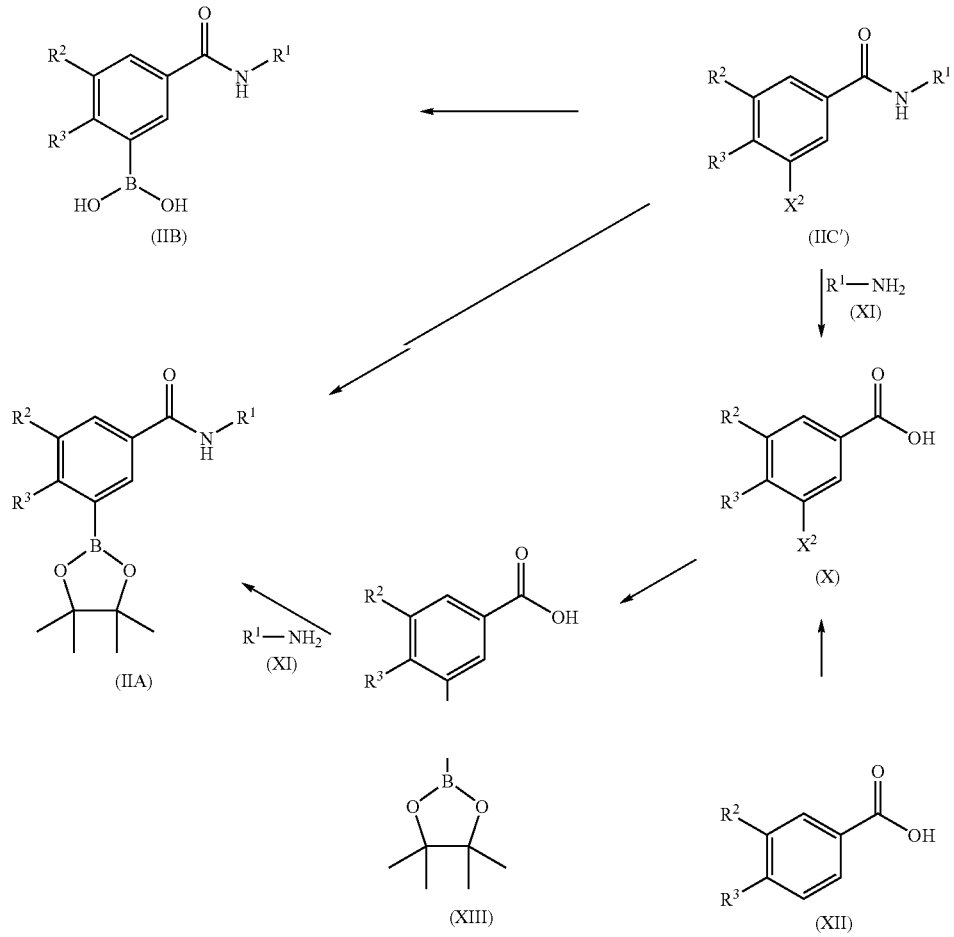

FIG. 3 pound of general formula (XII) with halogenating agents such as N-iodosuccinimide in the presence of a strong acid such as triflic acid.

In another alternative, compounds of formula (IIA) may be prepared by, for example, reacting a compound of formula (XIII) as hereinbefore defined, with an amine and a corresponding coupling agent such as O-(7-azabenzotriazol-1-yl-N,N,N',N'-tetramethyluronium hexafluorophosphate (HATU), in the presence of a base, such as diisopropylethylamine.

Compounds of formula (XIII) may be prepared from compounds of formula (X) following a similar procedure described hereinbefore for obtaining compounds of formula (IIA) from compounds of formula (IIC').

Compounds of general formula (III) are prepared following the synthetic scheme illustrated in FIG. 4.

Compounds of formula (IIB) may be prepared by, for example, reacting a compound of formula (IIC') in which $R^1$, $R^2$, and $R^3$ are as hereinbefore defined and $X^2$ is halogen atom, in particular iodine atom or bromine atom, with n-butyl lithium and triisopropyl borate in a solvent such as THF.

Compounds of formula (IIA) may be prepared by, for example, reacting a compound of formula (IIC'), as hereinbefore defined, with bis(pinnacolato)diboron, [1,1'-bis(diphenylphosphino)ferrocene]dichloropalladium (II) complex ($PdCl_2$(ppdf)) and potassium acetate in a solvent such as DMF Compounds of formula (IIC') may readily be prepared from a corresponding acid compound of formula (X) in which $R^2$, $R^3$ and $X^2$ are as hereinbefore defined, by converting the acid to an activated form of the acid, for example the acid chloride, by treatment with, for example, thionyl chloride, and then reacting the activated acid thus formed with an

FIG. 4

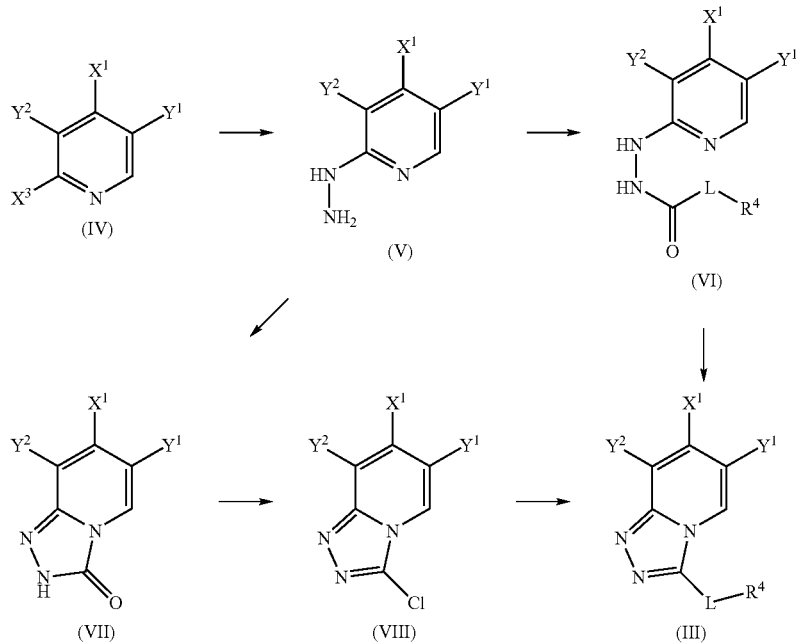

Compounds of formula (V) can be prepared by reacting compounds of formula (IV), wherein Y$^1$ and Y$^2$ are as above defined, X$^1$ represents I, Br or H atom, X$^3$ represents F or Cl atom) with hydrazine in a solvent such as ethanol or pyridine, at elevated temperature.

Compounds of general formula (IV) can be prepared by using known methodologies such as those described in *J. Org. Chem.* 1993, 58, 7832-7838.

Compounds of formula (VI) where L is a direct bond may be prepared by reacting compounds of formula (V) with a carboxylic acid or acid chloride (R$^4$—CO$_2$H or R$^4$—COCl) via amide bond formation procedures which employs for a carboxylic acid a coupling reagent, such as O-(7-azabenzotriazol-1-yl)-N,N,N',N'-tetramethyluronium hexafluorophosphate (HATU), in the presence of a base, such as diisopropylethylamine or in case of acid chlorides in the presence of a base such as triethylamine.

Alternatively, compounds of formula (VI) where L is O, S or NH may be prepared by reacting compounds of formula (V) with a chloroformate (R$^4$—O—COCl), a chlorothiolformate (R$^4$—S—COCl) or an isocianate (R$^4$—N—(CH$_2$)$_{0-1}$—CO) respectively in the presence of a base such as triethylamine or diisopropylethylamine.

Compounds of formula (III) may be prepared either by reacting compounds of formula (VI) with a chlorinating agent such as POCl$_3$, either neat or in an inert solvent such as toluene at elevated temperature or using Mitsunobu like conditions such as triphenylphosphine and diethyl azodicarboxylate in the presence of trimethylsilylazide and a base such as triethylamine or diisopropylethylamine in tetrahydrofuran.

Compounds of formula (VII) may be prepared by reacting compounds of formula (V) with a carbonylating agent such as carbonyldiimidazole or triphosgene in an inert solvent such as tetrahydrofuran. Compounds of formula (VIII) can be prepared by further treatment of compounds of formula (VII) with chlorinating agents such as POCl$_3$, either neat or in an inert solvent such as toluene at elevated temperature.

Compounds of general formula (III) may be prepared from compounds of formula (VIII) via displacement of the chlorine leaving group by the conjugate base of a compound R$^4$-L-H (where L is O, S or NR$^5$—(CH$_2$)$_{0-1}$) in an inert solvent such as THF in the presence of a base.

The starting material compounds of formula (XII) and (IV) are commercially available or may be readily prepared by using methologies already known in the art.

Biological Testing

Inhibition Assay

Enzymatic activity assay was performed in 96-well microtiter plates (Corning, catalog number # 3686) using a total volume of 50 µl of an assay buffer composed of 50 mM HEPES pH 7.5, 10 mM MgCl$_2$, 1.75 mM Na$_3$VO$_4$.

Various concentrations of the test compound or vehicle controls were pre-incubated for one hour with 0.055 µg/ml of the human p38alfa (SAPKa) enzyme (obtained from University of Dundee). The reaction started by addition of biotinylated ATF2 substrate and ATP in concentrations around their Km values (final concentration 0.62 µM and 60 µM respectively) and took place for one hour at 25° C. Addition of the detection reagents, streptavidin—XL665 and anti-phosphoresidue antibody coupled to Europium cryptate, caused the juxtaposition of the cryptate and the XL665 fluorophore, resulting in fluorescence energy transfer (FRET). The FRET intensity depends on the amount of bounded cryptate antibody, which is proportional to the extent of substrate phosphorylation. FRET intensity was measured using Victor 2V spectrofluorometer.

Data were analyzed by non-linear regression (Hill equation) to generate a dose-response curve. The calculated IC$_{50}$ value is the concentration of the test compound that caused a 50% decrease in the maximal FRET intensity.

Table 1 shows the activities inhibiting p38 assay of some compounds of the present invention.

TABLE 1

| Example | p38α IC$_{50}$ (nM) |
|---|---|
| 1 | 16 |
| 6 | 6 |
| 7 | 75 |
| 9 | 2 |
| 12 | 1.3 |
| 16 | 83 |
| 18 | 3.2 |
| 19 | 2 |
| 23 | 10 |
| 26 | 81 |
| 28 | 3 |
| 30 | 38 |
| 31 | 0.3 |
| 33 | 30 |
| 35 | 15.4 |
| 38 | 38 |
| 42 | 46 |
| 45 | 3.1 |
| 46 | 11.9 |
| 47 | 15.4 |

It can be seen from Table 1 that the compounds of formula (I) are potent inhibitors of the p38 mitogen-activated protein kinase. Preferred 3-([1,2,4]triazolo[4,3-a]pyridin-7-yl)benzamide derivatives of the invention possess a IC$_{50}$ value of inhibition of p38α of less than 1 μM, preferably less than 100 nM, more preferably less than 80 nM and most preferably less than 50 nM.

Functional Assay

The activity of compounds in inhibiting TNFα production was measured in a cellular assay using the human monocytic cell line THP-1. For this purpose, 2×10$^5$ cells/well were plated in tissue-culture treated round-bottom 96-well plates in RPMI (containing 10% FCS, L-Gln 2 mM, Hepes buffer 10 mM, sodium pyruvate 1 mM, glucose 4.5 gr/L, HNaCO$_3$ 1.5 g/L and beta-mercaptoethanol 50 μM), together with compounds at the desired test concentration and LPS (Sigma, L2630) at a final 10 μg/ml concentration. Compounds were resuspended in 100% DMSO at a concentration of 1 mM and titrated thereof in 10× dilutions in medium. Controls included stimulated cells alone and stimulated cells treated with the highest concentration of compound vehicle (1% DMSO). Cells were incubated for 5 h at 37° C. in a 5% CO$_2$ atmosphere. Cell supernatant was recovered by centrifugation and diluted 5-fold prior to testing in a standard human TNFα ELISA (RnD systems).

Data were analyzed by non-linear regression (Hill equation) to generate a dose-response curve. The calculated IC$_{50}$ value is the concentration of the test compound that caused a 50% decrease in the maximal TNFα production.

Compounds of the present invention are good inhibitors of TNFα production. Preferred 3-([1,2,4]triazolo[4,3-a]pyridin-7-yl)benzamide derivatives of the invention possess an IC$_{50}$ value for inhibiting TNFα production of less than 100 μM, preferably less than 10 μM, more preferably less than 1 μM and most preferably less than 100 nM.

The 3-([1,2,4]triazolo[4,3-a]pyridin-7-yl)benzamide derivatives of the invention are useful in the treatment or prevention of diseases known to be susceptible to improvement by inhibition of the p38 mitogen-activated protein kinase. Such diseases are, for example rheumatoid arthritis, ischemia-reperfusion injury, cerebral focal ischemia, acute coronary syndrome, asthma, COPD, Crohn's disease, irritable bowel syndrome, adult respiratory distress syndrome, osteoporosis, Alzheimer's disease, rheumatoid spondylitis, psoriasis, atherosclerosis, osteoarthritis or multiple myeloma.

Accordingly, the 3-([1,2,4]triazolo[4,3-a]pyridin-7-yl)benzamide derivatives of the invention and pharmaceutically acceptable salts thereof, and pharmaceutical compositions comprising such compound and/or salts thereof, may be used in a method of treatment of disorders of the human body which comprises administering to a subject requiring such treatment an effective amount of 3-([1,2,4]triazolo[4,3-a]pyridin-7-yl)benzamide derivative of the invention or a pharmaceutically acceptable salt thereof.

When the 3-([1,2,4]triazolo[4,3-a]pyridin-7-yl)benzamide derivatives of the invention are used for the treatment of respiratory diseases such as asthma, chronic obstructive pulmonary disorder, pulmonary fibrosis or emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) leukotriene D4 antagonists, (6) inhibitors of egfr-kinase, (7) antagonists of the A$_{2B}$ adenosine receptor, (8) NK1 receptor agonists, (9) CRTh2 antagonists, (10) syk kinase inhibitors, (11) CCR3 antagonists and (12) VLA-4 antagonists.

The present invention also provides pharmaceutical compositions comprising a 3-([1,2,4]triazolo[4,3-a]pyridin-7-yl)benzamide derivative of the invention and another active compound selected from the groups consisting of (1) antagonists of M3 muscarinic receptors, (2) β2-agonists, (3) PDE 4 inhibitors, (4) cortiocosteroids, (5) leukotriene D4 antagonists, (6) inhibitors of egfr-kinase, (7) antagonists of the A$_{2B}$ adenosine receptor, (8) NK1 receptor agonists, (9) CRTh2 antagonists, (10) syk kinase inhibitors, (11) CCR3 antagonists, (12) VLA-4 antagonists and (13) disease modifying antirheumatic drugs (DMARDs) such as methotrexate.

When 3-([1,2,4]triazolo[4,3-a]pyridin-7-yl)benzamide derivatives of the invention are used for the treatment of respiratory diseases such as asthma, chronic obstructive pulmonary disorder, pulmonary fibrosis, emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) CysLT1 and/or CysLT2 antagonists, (6) inhibitors of egfr-kinase, (7) A2b antagonits, (8) NK1 receptor agonists, (9) CRTh2 antagonists, (10) syk kinase inhibitors, (11) CCR3 antagonists and (12) VLA-4 antagonists.

When 3-([1,2,4]triazolo[4,3-a]pyridin-7-yl)benzamide derivatives of the invention are used for the treatment of autoimmune diseases such as psoriasis, rheumatoid arthritis, psoriatic arthritis, ankylosing spondilytis, Reiter's syndrome, fibromyalgia, inflammatory bowel disease such as ulcerative colitis and Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, autoimmune chronic active hepatitis, myasthenia gravis, or Addison's disease it may be advantageous to use them in combination with other active compounds known to be useful in the treatment of autoimmune diseases such as PDE4 inhibitors, CysLT1 and/or CysLT2 antagonists, inhibitors of egfr-kinase, A2b antagonits, NK1 receptor agonists, CCR3 antagonists, VLA-4 antagonists and disease modifying antirheumatic drugs (DMARDs).

Examples of suitable M3 antagonists (anticholinergics) that can be combined with the inhibitors of the p38 mitogen-activated protein kinase of the present invention are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N-[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Examples of suitable β2-agonists that can be combined with the inhibitors of the p38 mitogen-activated protein kinase of the present invention are: arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, milveterol, GSK-678007, GSK-642444, GSK-159802, LAS100977, HOKU-81, KUL-1248, carmoterol, indacaterol and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{-4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol optionally in the form of their racemates, their enantiomers, their diastereomers, and mixtures thereof, and optionally their pharmacologically-compatible acid addition salts and the compounds claimed in Spanish Patent application numbers P200501229 and P200601082. When the β2-agonists are in the form of a salt or derivative It is particularly preferred that it is in a form selected from the sodium salts, sulfobenzoates, phosphates, isonicotinates, acetates, propionates, dihydrogen phosphates, palmitates, pivalates, fumarates, furoates, xinafoates or mixtures thereof.

The following β2-agonists are of special interest for the combination with the compounds of formula (I): arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, milveterol, LAS100977, KUL-1248, carmoterol and indacaterol optionally in the form of their racemates, their enantiomers, their diastereomers, and mixtures thereof, and optionally their pharmacologically-compatible acid addition salts Still most preferred are the following β2-agonists: formoterol, salmeterol and GSK-597901, milveterol, LAS100977 and indacaterol optionally in the form of their racemates, their enantiomers, their diastereomers and mixtures thereof, and optionally their pharmacologically-compatible acid addition salts. Still more preferred are salmeterol and formoterol.

Examples of suitable PDE4 inhibitors that can be combined with the inhibitors of the p38 mitogen-activated protein kinase of the present invention are denbufylline, rolipram, cipamfylline, arofylline, filaminast, piclamilast, mesopram, drotaverine hydrochloride, lirimi-last, cilomilast, oglemilast, apremilast, 6-[2-(3,4-Diethoxyphenyl)thiazol-4-yl]pyridine-2-carboxylic acid (tetomilast), (R)-(+)-4-[2-(3-Cyclopentyloxy-4-methoxyphenyl)-2-phenylethyl]pyridine, N-(3,5-Dichloro-4-pyridinyl)-2-[1-(4-fluorobenzyl)-5-hydroxy-1H-indol-3-yl]-2-oxoacetamide(GSK-842470), 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluoromethoxyphenyl)cyclohexan1-one, cis[4-cyano-4-(3-cyclopropylmethoxy-4-difluoromethoxyphenyl)cyclohexan-1-ol, ONO-6126 (Eur Respir J 2003, 22(Suppl. 45): Abst 2557) and the compounds claimed in the PCT patent application numbers WO03/097613, WO2004/058729 A1, WO 2005/049581 A1, WO 2005/123693 and WO 2005/123692.

Examples of suitable corticosteroids and glucocorticoids that can be combined with the inhibitors of the p38 mitogen-activated protein kinase of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable CysLT1 and/or CysLT2 antagonists that can be combined with the inhibitors of the p38 mitogen-activated protein kinase of the present invention are tomelukast, Ibudilast, pobilukast, pranlukast hydrate, zafirlukast, ritolukast, verlukast, sulukast, tipelukast, cinalukast, iralukast sodium, masilukast, montelukast sodium, 5-[3-[3-(2-Quinolinylmethoxy)phenoxy]propyl]-1H-tetrazole, (E)-8-[2-[4-[4-(4-Fluorophenyl)butoxy]phenyl]vinyl]-2-(1H-tetrazol-5-yl)-4H-benzopyran-4-one sodium salt, 2-[N-[4-(4-Chlorophenylsulfonamido)butyl]-N-[3-(4-isopropylthiazol-2-ylmethoxy)benzyl]sulfamoyl]benzoic acid, (3R,4R)-3-[6-(5-Fluorobenzothiazol-2-ylmethoxy)-4-hydroxy-3,4-dihydro-2H-1-benzopyran-3-ylmethyl]benzoic acid, 2-[2-[2-(4-tert-Butylthiazol-2-yl)benzofuran-5-yloxymethyl]phenyl]acetic acid hydrochloride, 5-[2-[4-(Quinolin-2-ylmethoxy)phenoxymethyl]benzyl]-1H-tetrazole, (E)-2,2-Diethyl-3'[2-[2-(4-isopropyl)thiazolyl]ethenyl] succinanilic acid; 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H)-one, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, MCC-847 (from AstraZeneca), (+)-4(S)-(4-Carboxyphenylthio)-7-[4-(4-phenoxybutoxy)phenyl]-5(Z)-heptenoic acid and the compounds claimed in PCT patent application WO2004/043966A1.

Examples of suitable inhibitors of egfr-kinase that can be combined with the inhibitors of the p38 mitogen-activated protein kinase of the present invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable antagonists of the A2b adenosine receptor that can be combined with the inhibitors of the p38 mitogen-activated protein kinase of the present invention are CVT-6883 from CV Therapeutics, 4-(1-butylxanthin-8-yl) benzoic acid, 8-[1-[3-(4-chlorophenyl)-1,2,4-oxadiazol-5-ylmethyl]-1H-pyrazol-4-yl]-1,3-dipropylxanthine, N-(1,3-benzodioxol-5-yl)-2-[5-(1,3-dipropylxanthin-8-yl)-1-methyl-1H-pyrazol-3-yloxy]acetamide, 8-[4-[5-(2-methoxyphenyl)-1,2,4-oxadiazol-3-ylmethoxy]phenyl]-1,3-dipropylxanthine, 3-[5-(2-methyl-1H-imidazol-1-yl)-2-(pyrazin-2-ylamino)thiazol-4-yl]benzonitrile, 4-(2,6-dioxo-1-propyl-2,3,6,7-tetrahydro-1H-purin-8-yl)benzenesulfonic acid, 1-[2-[8-(3-fluorophenyl)-9-methyl-9H-adenin-2-yl] ethynyl]cyclopentanol hydrochloride, N-(2-acetylphenyl)-2-[4-(1,3-dipropylxanthin-8-yl)phenoxy]acetamide, N-(4-acetylphenyl)-2-[4-(1,3-dipropylxanthin-8-yl)phenoxy] acetamide, N-(4-cyanophenyl)-2-[4-(1,3-dipropylxanthin-8-yl)phenoxy]acetamide, 4-(3,4-dichlorophenyl)-5-(4-pyridinyl)thiazol-2-amine or the compounds of international patent applications WO 2005/040155 A1, WO2005/100353 A1, WO 2007/039297 and WO2007/017096 A1.

Examples of suitable NK1-receptor antagonists that can be combined with the inhibitors of the p38 mitogen-activated protein kinase of the present invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allothreonyl-asparaginyl-serine C-1.7-O-3.1 lactone, 1-Methylindol-3-ylcarbonyl-[4(R)-hydroxy]-L-prolyl-[3-(2-naphthyl)]-L-alanine N-benzyl-N-methylamide, (+)-(2S,3S)-3-[2-Methoxy-5-(trifluoromethoxy)benzylamino]-2-phenylpiperidine, (2R,4S)-N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine]2(S)-oxide hydrochloride and the compound CS-003 described in Eur Respir J 2003, 22(Suppl. 45): Abst P2664.

Examples of suitable CRTh2 antagonists that can be combined with the inhibitors of the p38 mitogen-activated protein kinase of the present invention are 2-[5-Fluoro-2-methyl-1-[4-(methylsulfonyl)phenylsulfonyl]-1H-indol-3-yl]acetic acid, Ramatroban, [(3R)-4-(4-chlorobenzyl)-7-fluoro-5-(methylsulfonyl)-1,2,3,4tetrahydrocyclopenta[b]indol-3-yl] acetic acid and (1R,2R,3S,5S)-7-[2-(5-Hydroxybenzothiophen-3-ylcarboxamido)-6,6-dimethylbicyclo[3.1.1] hept-3-yl]-5(Z)-heptenoic acid Examples of suitable Syk kinase inhibitors that can be combined with the inhibitors of the p38 mitogen-activated protein kinase of the present invention are piceatannol, 2-(2-Aminoethylamino)-4-[3-(trifluoromethyl)phenylamino]pyrimidine-5-carboxamide, R-091 (from Rigel), R-112 (from Rigel), R-343 (from Rigel), R-788 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate, 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide, 2-[7-(3,4-Dimethoxyphenyl)imidazo[1,2-c]pyrimidin-5-ylamino] pyridine-3-carboxamide dihydrochloride and AVE-0950 (from Sanofi-Aventis).

Examples of CCR3 antagonists that can be combined with the inhibitors of the p38 mitogen-activated protein kinase of the present invention are 4-[3-[4-(3,4-Dichlorobenzyl)morpholin-2(S)-ylmethyl]ureidomethyl]benzamide, N-[1(R)-[4-(3,4-Dichlorobenzyl)piperidin-1-ylmethyl]-2-methylpropyl]-N'-(3,4,5-trimethoxyphenyl)urea, N-[1(S)-[4-(4-Chlorobenzyl)piperidin-1-ylmethyl]-2-hydroxypropyl]-N'-(3,4,5-trimethoxyphenyl)urea, 3-[3-(3-Acetylphenyl) ureido]-2-[4-(4-fluorobenzyl)piperidin-1-ylmethyl]-N-methylbenzamide, 4-(3,4-Dichlorobenzyl)-1-methyl-1-[3-methyl-2(R)-[3-(3,4,5-trimethoxyphenyl)ureido]butyl] piperidinium chloride, N-[2-[4(R)-(3,4-Dichlorobenzyl) pyrrolidin-2(S)-yl]ethyl]-2-[5-(3,4-dimethoxyphenyl) pyrimidin-2-ylsulfanyl]acetamide, CRIC-3 (from IPF Pharmaceuticals), 2(R)-[1-[1-(2,4-Dichlorobenzyl)-4(S)-(3-thienyl)pyrrolidin-3(S)-ylmethyl]piperidin-4-ylmethyl]pentanoic acid, 8-[1-(2,4-Dichlorobenzyl)-4(S)-(3-thienyl)pyrrolidin-3(S)-ylmethyl]-3,3-dipropyl-1-oxa-8-azaspiro[4.5] decane-2(S)-carboxylic acid, 11-[1-(2,4-Dichlorobenzyl)-4(S)-(3-thienyl)pyrrolidin-3(S)-ylmethyl]-3,14-dioxa-11-azadispiro[5.1.5.2]pentadecane-15(S)-carboxylic acid, W-56750 (from Mitsubishi Pharma), N-[1(S)-[3endo-(4-Chlorobenzyl)-8-azabicyclo[3.2.1]oct-8-ylmethyl]-2(S)-hydroxypropyl]-N'-(3,4,5-trimethoxyphenyl)urea, N-(3-Acetylphenyl)-N'-[(1R,2S)-2-[3(S)-(4-fluorobenzyl) piperidin-1-ylmethyl]cyclohexyl]urea benzenesulfonate, trans-1-(Cycloheptylmethyl)-4-(2,7-dichloro-9H-xanthen- 9-ylcarboxamido)-1-methylpiperidinium iodide, GW-782415 (from GlaxoSmithKline), GW-824575 (from GlaxoSmithKline), N-[1'-(3,4-Dichlorobenzyl)-1,4'-bipiperidin-3-ylmethyl]quinoline-6-carboxamide, N-[1-(6-Fluoronaphthalen-2-ylmethyl)pyrrolidin-3(R)-yl]-2-[1-(3-hydroxy-5-methylpyridin-2-ylcarbonyl)piperidin-4-ylidene]acetamide fumarate and DIN-106935 (from Bristol-Myers Squibb).

Examples of VLA-4 antagonists that can be combined with the inhibitors of the p38 mitogen-activated protein kinase of the present invention are N-[4-[3-(2-Methylphenyl)ureido]phenylacetyl]-leucyl-L-aspartyl-L-valyl-L-proline, 3(S)-[2(S)-[4,4-Dimethyl-3-[4-[3-(2-methylphenyl)ureido]benzyl]-2,5-dioxoimidazolidin-1-yl]-4-methylpentanoylamino]-3-phenylpropionic acid, 2(S)-(2,6-Dichlorobenzamido)-3-(2',6'-dimethoxybiphenyl-4-yl)propionic acid, RBx-4638 (from Ranbaxy), R-411 (from Roche), RBx-7796 (from Ranbaxy), SB-683699 (from GlaxoSmithKline), DW-908e (from Daiichi Pharmaceutical), RO-0270608 (from Roche), AJM-300 (from Ajinomoto), PS-460644 (from Pharmacopeia) and the compounds claimed in PCT patent application numbers WO 02/057242 A2 and WO 2004/099126 A1.

Examples of disease modifying antirheumatic drugs (DMARs) that can be combined with the inhibitors of the p38 mitogen-activated protein kinase of the present invention are auranofin, azathioprine, bucillamine, cyclosporine, iguratimod, leflunomide, methotrexate, pentostatin, rimacalib hydrochloride, romazarit, salazodine, sulphasalazine, teriflunomide, (E)-5-(3,5-Di-tert-butyl-4-hydroxybenzylidene)-2-ethylisothiazolidine 1,1-dioxide, cis-2-(4-Chlorophenyl)-4,5-diphenyl-4,5-dihydro-1H-imidazole hydrochloride, 2-[8-[2-[6-(Methylamino)pyridyl-2-ylethoxy]-3-oxo-2-(2,2,2-trifluoroethyl)-2,3,4,5-tetrahydro-1H-2-benzazepin-4-(S)-yl]acetic acid, 4-acetoxy-2-(4-methylphenyl)benzothiazole, 3-[4-Methyl-3-[N-methyl-N-(7H-pyrrolo[2,3-d]pyrimidin-4-yl-amino]piperidin-1-yl]-3-oxopropionitrile (CP-690550), 3-Deazaadenosine, 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406), AD-452 from Sosei, AD-827 from Arakis, BB-2983 from British Biotech, SC-12267 from 4SC, CPH-82 from Conpharm, R-1295 from Roche, R-1503 from Roche and N2-[3-[1(S)-(2-Fluorobiphenyl-4-yl)ethyl]isoxazol-5-yl]morpholine-4-carboxamidine hydrochloride (SMP-114).

The combinations of the invention may be used in the treatment of disorders which are susceptible to amelioration by inhibition of the p38 mitogen-activated protein kinase. Thus, the present application encompasses methods of treatment of these disorders, as well as the use of the combinations of the invention in the manufacture of a medicament for the treatment of these disorders, specially for the treatment of rheumatoid arthritis.

The present invention also provides pharmaceutical compositions which comprise, as an active ingredient, at least a 3-([1,2,4]triazolo[4,3-a]pyridin-7-yl)benzamide derivative of formula (I) or a pharmaceutically acceptable salt thereof in association with a pharmaceutically acceptable excipient such as a carrier or a diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, inhaled, nasal, rectal, percutaneous or injectable administration. Compositions for oral administration may be in the form of syrups, tablets, capsules, lozenges, controlled-release preparations, fast-dissolving preparations, etc. Compositions for topical administration may be in the form of creams, ointments, lotions, nasal sprays or aerosols, etc). Compositions for administration by injection may be in the form of subcutaneous, intradermic, intramuscular or intravenous compositions. Compositions for administration by inhalation may be in the form of a dry powder, a solution, a dispersion, etc.

The active compounds in the combination, i.e. the inhibitiors of the p38 mitogen-activated protein kinase of the invention, and the other optional active compounds may be administered together in the same pharmaceutical composition or in different compositions intended for separate, simultaneous, concomitant or sequential administration by the same or a different route.

One execution of the present invention consists of a kit of parts comprising an the inhibitiors of the p38 mitogen-activated protein kinase of the present invention together with instructions for simultaneous, concurrent, separate or sequential use in combination with another active compound useful in the treatment of a respiratory disease which responds to inhibition of the p38 mitogen-activated protein kinase.

Another execution of the present invention consists of a package comprising an inhibitiors of the p38 mitogen-activated protein kinase of formula (I) and another active compound useful in the treatment of a respiratory disease for the simultaneous, concurrent, separate or sequential use in the treatment of a respiratory disease which responds to the inhibition of the p38 mitogen-activated protein kinase.

The pharmaceutically acceptable excipients which are admixed with the active compound or salts of such compound, to form the compositions of this invention are well-known per se and the actual excipients used depend inter alia on the intended method of administering the compositions.

The diluents which may be used in the preparation of the compositions include those liquid and solid diluents which are compatible with the active ingredient, together with colouring or flavouring agents, if desired. Tablets or capsules may conveniently contain between 1 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For single dose inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air; (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring plungers with a local or circumferential recess to displace a certain volume of powder from the container to a delivery chamber or an air conduit e.g. EP 0505321, WO 92/04068 and WO 92/04928, or measuring slides such as the Novolizer SD2FL (ex. Sofotec) which is described in the following patent applications: WO 97/000703, WO 03/000325 and WO 03/061742.

Apart from applications through dry powder inhalers the compositions of the invention can also be administered in aerosols which operate via propellant gases or by means of so-called atomisers, via which solutions of pharmacologically-active substances can be sprayed under high pressure so that a mist of inhalable particles results. Such atomisers are described, for example, in WO 91/14468 and WO 97/12687.

Effective doses are normally in the range of 1-2000 mg of active ingredient per day. Daily dosage may be administered in one or more treatments, preferably from 1 to 4 treatments, per day.

The syntheses of the compounds of the invention and of the intermediates for use therein are illustrated by the following Examples (1 to 53) including Preparation Examples (Intermediates 1-37) which do not limit the scope of the invention in any way.

$^1$H Nuclear Magnetic Resonance Spectra were recorded on a Varian Gemini 300 spectrometer. Melting points were recorded using a Büchi B-540 apparatus. The chromatographic separations were obtained using a Waters 2795 system equipped with a Symmetry C18 (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

INTERMEDIATES

Intermediate 1

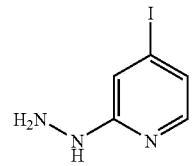

2-Hydrazinyl-4-iodopyridine

A solution of 2-fluoro-4-iodopyridine (prepared as described in Rocca, P. et al *J. Org. Chem.* 1993, 58, 7832-7838) (8.72 g, 39.1 mmol) in 80 mL of ethanol was treated with 20 mL of hydrazine hydrate and the mixture was stirred at room temperature (24-25° C.) for 20 hours. At the end of the reaction, the mixture was concentrated in vacuum and the resulting solid triturated with a mixture of hexanes/diethyl ether affording (8.52 g, 93%) the desired compound that was used in the following steps without further purification.

LRMS (m/z): 235 (M+1)$^+$.

$^1$H-NMR δ (CDCl$_3$): 3.78 (brs, 2H), 5.87 (brs, 1H), 7.02 (d, J=5.5 Hz, 1H), 7.19 (s, 1H), 7.77 (d, J=5.5 Hz, 1H).

Intermediate 2

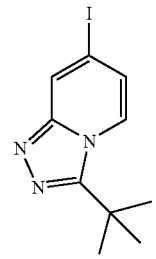

3-tert-Butyl-7-iodo-[1,2,4]triazolo[4,3-a]pyridine a) N'-(4-iodopyridin-2-yl)-2,2-dimethylpropanohydrazide To a suspension of Intermediate 1 (7.45 g, 31.70 mmol) in toluene (140 mL), under argon atmosphere was added at 0° C. triethylamine and pivaloyl chloride leaving the reaction at this temperature for 15 minutes. Afterwards, the reaction mixture was stirred at room temperature for 1.2 hours. Subsequently, the mixture was poured into water (200 mL) and it was extracted with ethyl acetate (3×200 mL). The organic layer was washed with aqueous sodium bicarbonate (4%) (3×200 mL) and brine, dried over anhydrous sodium sulphate and the solvent removed under reduced pressure. The resulting solid (9.64 g) was used in the next step without further purification.

b) 3-tert-Butyl-7-iodo-[1,2,4]triazolo[4,3-a]pyridine

The solid obtained in step a) was reacted with phosphorous oxychloride at 100° C. for 50 minutes, then the reaction was poured into ice, neutralized with sodium hydroxide 8M and extracted with ethyl acetate (500 mL). The organic phase was washed with aqueous sodium bicarbonate (4%), water and brine and it was dried over anhydrous sodium sulphate and the solvent removed under reduced pressure. The resulting residue was triturated with hexanes/diethyl ether to afford 6.72 g (57%) of the desired product. Variable amounts of the 7-chloro analogue were observed (approx. 10%) but the crude product obtained was used in the next step without further purification.

LRMS (m/z): 302 (M+1)$^+$.

$^1$H-NMR δ (CDCl$_3$): 1.60 (s, 9H), 7.00 (d, J=7.3 Hz, 1H), 7.93 (d, J=7.3 Hz, 1H), 8.21 (s, 1H).

Intermediate 3

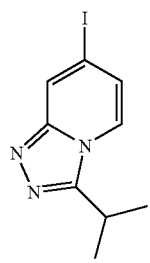

7-Iodo-3-isopropyl-[1,2,4]triazolo[4,3-a]pyridine

Obtained as a white solid (66%) from Intermediate 1 and isobutyryl chloride following the experimental procedure described for the synthesis of Intermediate 2.

LRMS (m/z): 288 (M+1)$^+$.

$^1$H-NMR δ (CDCl$_3$): 1.38 (d, J=6.9 Hz, 6H), 3.16 (m, 1H), 7.05 (d, J=6.8 Hz, 1H), 7.65-7.68 (m, 2H).

Intermediate 4

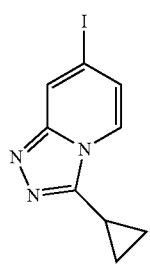

3-Cyclopropyl-7-iodo-[1,2,4]triazolo[4,3-a]pyridine

Obtained as a yellow solid (73%) from Intermediate 1 and cyclopropanecarbonyl chloride following the experimental procedure described for the synthesis of Intermediate 2.

LRMS (m/z): 286 (M+1)$^+$.

Intermediate 5

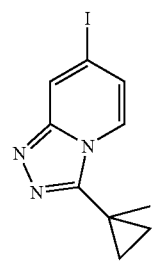

7-Iodo-3-(1-methylcyclopropyl)-[1,2,4]triazolo[4,3-a]pyridine

Obtained as a brown solid (66%) from Intermediate 1 and 1-methylcyclopropanecarbonyl chloride following the experimental procedure described for the synthesis of Intermediate 2.

LRMS (m/z): 300 (M+1)$^+$.

Intermediate 6

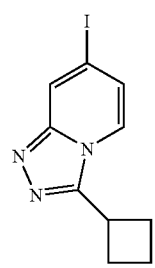

3-Cyclobutyl-7-iodo-[1,2,4]triazolo[4,3-a]pyridine

Obtained as a yellow solid (61%) from Intermediate 1 and cyclobutanecarbonyl chloride following the experimental procedure described for the synthesis of Intermediate 2.

LRMS (m/z): 300 (M+1)$^+$.

Intermediate 7

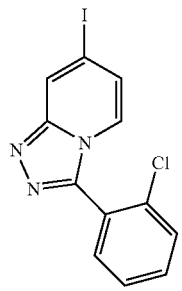

3-(2-Chlorophenyl)-7-iodo-[1,2,4]triazolo[4,3-a]pyridine

Obtained as a yellow solid (46%) from Intermediate 1 and 2-chlorobenzoyl chloride following the experimental procedure described for the synthesis of Intermediate 2.

LRMS (m/z): 356 (M+1)$^+$.

Intermediate 8

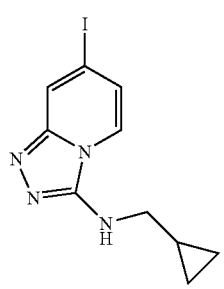

N-(Cyclopropylmethyl)-7-iodo-[1,2,4]triazolo[4,3-a]pyridin-3-amine

To a solution of triphosgene (220 mg, 0.74 mmol) in dried dichloromethane (5 mL) was added under argon at 0° C., a solution of cyclopropylmethylamine (154 mg, 2.16 mmol) in dichloromethane (3 mL) and afterwards a solution of triethylamine (590 µL, 4.24 mmol) in dichloromethane (2 mL), allowing the reaction to stir for 2 hours at room temperature. Subsequently, the reaction mixture was cooled down to 0° C. and a suspension of Intermediate 1 (500 mg, 2.12 mmol) in dichloromethane (5 mL) was added, stirring at room temperature for 18 hours. At the end of the reaction, a solid appeared that was filtered affording 385 mg of the corresponding urea. This intermediate urea was used in the next step without further purification, forming a suspension in phosphorous oxychloride (5 mL) and stirring the reaction mixture at 75° C. overnight. When the reaction was completed, it was allowed to cool to room temperature and was poured into ice-water carefully. This mixture was neutralized with sodium hydroxide 8M and was extracted with ethyl acetate (2×100 mL). The organic phase was washed with brine, dried and concentrated to afford 300 mg of a residue that was purified by reverse phase (C18 Waters 25+S). A yellow solid was obtained (106 mg, 16%) corresponding to the title intermediate compound.

LRMS (m/z): 315 (M+1)$^+$.

$^1$H-NMR δ (CDCl$_3$): 0.12-0.44 (m, 2H), 0.45-0.77 (m, 2H), 1.01-1.40 (m, 1H), 3.20-3.56 (m, 2H), 3.94-4.19 (m, 1H), 6.88 (d, J=7.4 Hz, 1H), 7.42 (d, J=7.4 Hz, 1H), 8.00 (s, 1H).

Intermediate 9

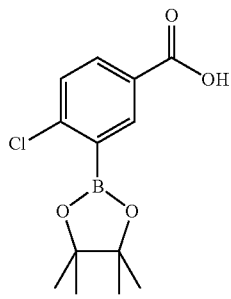

4-Chloro-3-(4,4,5,5-tetramethyl-1,3,2-dioxaborolan-2-yl)benzoic acid

In a Schlenk tube were charged 3-bromo-4-chlorobenzoic acid (2 g, 8.49 mmol), 4,4,5,5,4',4',5',5'-Octamethyl-[2,2']bi[[1,3,2]dioxaborolanyl] (3.23 g, 12.72 mmol), potassium acetate (4.17 g, 42.49 mmol) and dimethylformamide (40 mL). The mixture was submitted to three vacuum argon cycles, then [1,1'-bis(diphenylphosphino)ferrocene]dichloro-palladium(II) complex with dichloromethane (1:1) (700 mg, 0.87 mmol) was added and the mixture purged in the same way. The reaction was stirred at 80° C. under argon for 5 hours.

Subsequently, the dimethylformamide was removed under vacuum, sodium hydroxide 2N (50 mL) was added and this mixture extracted with ethyl acetate (2×100 mL). The aqueous phase was acidified with hydrochloric acid 5N until pH=3 in an ice-water bath, appearing a solid that was filtered affording 1.3 g (54%) of the title compound.

LRMS (m/z): 199 (M−1)$^+$ (corresponding to the boronic acid generated within the HPLC column).

$^1$H-NMR δ (DMSO-d6): 1.34 (s, 12H), 7.58 (d, J=8.3 Hz, 1H), 8.00 (d, J=8.3 Hz, 1H), 8.24 (s, 1H), 12.28 (brs, 1H).

Intermediate 10

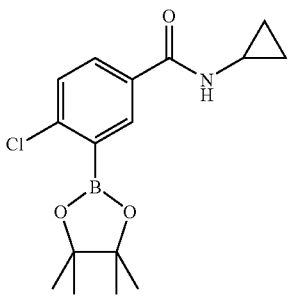

4-Chloro-N-cyclopropyl-3-(4,4,5,5-tetramethyl-1,3,2-dioxaborolan-2-yl)benzamide To a solution of Intermediate 9 (294 mg, 1.04 mmol) in dimethylformamide (3 mL) was added cyclopropylamine (88 µL, 1.28 mmol), diisopropylethylamine (408 µL, 2.34 mmol) and O-(7-azabenzotriazol-1-yl)-N,N,N',N'-tetramethyluronium hexafluorophosphate (388 mg, 1.02 mmol). The clear solution was stirred at room temperature for 1 day. Subsequently, the dimethylformamide was evaporated and the residue treated with ethyl acetate (75 mL). This organic phase was washed with aqueous sodium bicarbonate (4%) (100 mL), water and brine, dried and concentrated to afford an oily residue. This oil was treated with a mixture of hexanes-diethyl ether yielding 240 mg (72%) of the title compound.

LRMS (m/z): 240 (M+1)$^+$ (corresponding to the boronic acid generated within the HPLC column).

$^1$H-NMR δ (DMSO-d6): 0.58 (m, 2H), 0.70 (m, 2H), 1.33 (s, 12H), 2.84 (m, 1H), 7.51 (d, J=8.3 Hz, 1H), 7.88 (d, J=8.3 Hz, 1H), 8.06 (s, 1H), 8.59 (brs 1H).

Intermediate 11

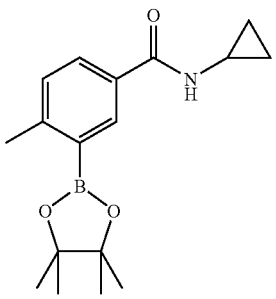

N-Cyclopropyl-4-methyl-3-(4,4,5,5-tetramethyl-1,3,2-dioxaborolan-2-yl)benzamide

Obtained as a white solid from 3-iodo-4-methylbenzoic acid following the experimental procedures described in Intermediates 9 and 10

LRMS (m/z): 302 (M+1)$^+$.

Intermediate 12

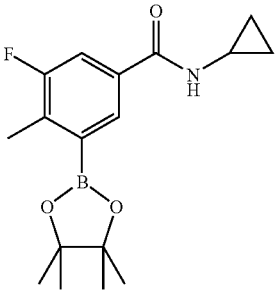

N-Cyclopropyl-3-fluoro-4-methyl-5-(4,4,5,5-tetramethyl-1,3,2-dioxaborolan-2-yl)benzamide a) N-Cyclopropyl-3-fluoro-5-iodo-4-methylbenzamide N-Iodosuccinimide (3.31 g) was added in portions to a solution of 3-fluoro-4-methylbenzoic acid (2.27 g) in trifluoromethanesulphonic acid (15 mL) at 0° C. over 3 hours and the mixture was allowed to warm to room temperature overnight. The reaction mixture was poured into ice/water and the precipitate was collected by filtration and rinsed with water. The solid was dissolved in ethyl acetate, washed with aqueous sodium thiosulphate and brine, dried over anhydrous magnesium sulphate and the solvent was removed under vacuum. The residue obtained was treated with thionyl chloride (20 mL) and heated at 100° C. for 2.5 hours. Excess thionyl chloride was removed under vacuum and the residue was dissolved in dichloromethane (20 mL). Sodium carbonate (3.7 g) and cyclopropylamine (1.9 mL) were added to the solution and the mixture was stirred at room temperature for 72 hours. The mixture was filtered and the residue was rinsed with dichloromethane and ethyl acetate. The combined filtrates and washings were concentrated under vacuum. The residue was purified by flash chromatography eluting with hexanes:ethyl acetate (10:1 to 5:1) to give 2.13 g (45%) of N-cyclopropyl-3-fluoro-5-iodo-4-methylbenzamide.

b) N-Cyclopropyl-3-fluoro-4-methyl-5-(4,4,5,5-tetramethyl-1,3,2-dioxaborolan-2-yl)benzamide The compound obtained in step a (1.0 g), 4,4,5,5,4',4',5',5'-octamethyl-[2,2']bi[[1,3,2]dioxaborolanyl] (1.2 g), potassium acetate (1.23 g) and [1,1'-bis(diphenylphosphino)ferrocene]dichloro-palladium(II) complex with dichloromethane (1:1) (154 mg) were mixed in dimethylformamide (38 mL) and heated at 110° C. for 18 hours. The cooled reaction was concentrated in vacuo and the residue was purified by flash chromatography eluting with hexanes:ethyl acetate (6:1) to give the title compound (710 mg, 57% yield).

LRMS (m/z): 320 (M+1)$^+$.

Intermediate 13

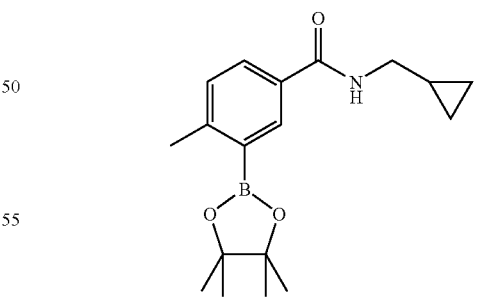

N-(Cyclopropylmethyl)-4-methyl-3-(4,4,5,5-tetramethyl-1,3,2-dioxaborolan-2-yl)benzamide Obtained as a white solid from 3-iodo-4-methylbenzoic acid following the experimental procedures described for the synthesis of Intermediates 9 and 10.

LRMS (m/z): 316 (M+1)$^+$.

Intermediate 14

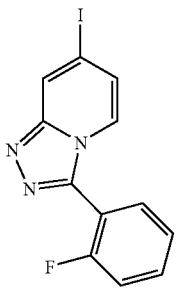

3-(2-Fluorophenyl)-7-iodo-[1,2,4]triazolo[4,3-a]pyridine

This compound was prepared (32%) from Intermediate 1 and 2-fluorobenzoyl chloride following the experimental procedure described for the synthesis of Intermediate 2.
LRMS (m/z): 339 (M+1)$^+$.

Intermediate 15

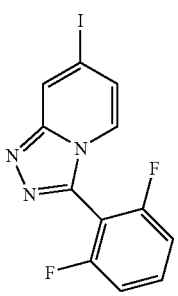

3-(2,6-Difluorophenyl)-7-iodo-[1,2,4]triazolo[4,3-a]pyridine

This compound was prepared (62%) from Intermediate 1 and 2,6-difluorobenzoyl chloride following the experimental procedure described for the synthesis of Intermediate 2.
LRMS (m/z): 358 (M+1)$^+$.

Intermediate 16

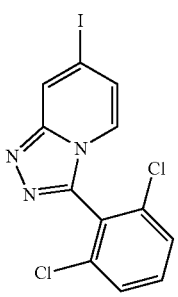

3-(2,6-Dichlorophenyl)-7-iodo-[1,2,4]triazolo[4,3-a]pyridine

This compound was prepared (34%) from Intermediate 1 and 2,6-dichlorobenzoyl chloride following the experimental procedure described for the synthesis of Intermediate 2.
LRMS (m/z): 390 (M+1)$^+$.

Intermediate 17

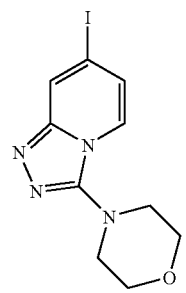

7-Iodo-3-morpholin-4-yl-[1,2,4]triazolo[4,3-a]pyridine

This compound was prepared (51%) from Intermediate 1 and morpholine-4-carbonyl chloride following the experimental procedure described for the synthesis of Intermediate 2.
LRMS (m/z): 331 (M+1)$^+$.
$^1$H-NMR δ (CDCl$_3$): 3.24-3.36 (m, 4H), 3.83-4.02 (m, 4H), 6.98 (d, J=7.4 Hz, 1H), 7.56 (d, J=7.4 Hz, 1H), 8.10 (d, J=0.8 Hz, 1H).

Intermediate 18

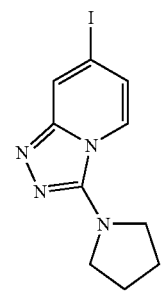

7-Iodo-3-pyrrolidin-1-yl-[1,2,4]triazolo[4,3-a]pyridine

This compound was prepared (15%) from Intermediate 1 and pyrrolidine-1-carbonyl chloride following the experimental procedure described for the synthesis of Intermediate 2.
LRMS (m/z): 315 (M+1)$^+$.

Intermediate 19

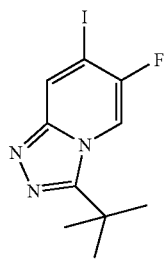

3-tert-Butyl-6-fluoro-7-iodo-[1,2,4]triazolo[4,3-a]pyridine a) 2,5-Difluoro-4-iodopyridine n-BuLi 2.5M in hexanes (4.9 mL, 12.25 mmol) was added to a solution of diisopropylamine (1.7 mL, 12.20 mmol) in tetrahydrofuran (22 mL) at −20° C., under nitrogen atmosphere, over a period of 10 minutes. The solution was stirred at −20° C. for 30 min and then it was cooled to −78° C. A solution of 2,5-difluoropyridine (1.33 g, 11.5 mmol) in tetrahydrofuran (3 mL) was added over a period of 30 min and the mixture was stirred at −78° C. for 4 hours. After this time, a solution of iodine (3.20 g, 12.6 mmol) in tetrahydrofuran (10 mL) was added dropwise and the mixture was stirred at −78° C. for 1 hour. Water (1 mL) and tetrahydrofuran (3 mL) were added and the temperature was allowed to raise until room temperature, then water (25 mL) and aqueous sodium bisulphite 40% p/v (3 mL) were added. The organic layer was separated and the aqueous layer was extracted with diethyl ether (3×50 mL), the combined organic layers were washed with brine, dried over anhydrous magnesium sulphate and the solvent removed under reduced pressure. The residue was purified by silica flash chromatography (5% diethyl ether in hexanes) to yield the title compound (1.35 g, 48%) as a white crystalline solid.

b) 5-Fluoro-2-hydrazinyl-4-iodopyridine

A solution of 2,5-difluoro-4-iodopyridine (1.35 g, 5.602 mmol) in ethanol (7 mL) was treated with hydrazine hydrate (2.75 mL) and the mixture was stirred at 50° C. for 19 hours. The mixture was concentrated in vacuum and the resulting solid triturated with water, filtered, rinsed with more water and dried to yield the title compound (0.57 g, 35%) that was used in the following steps without further purification.

c) N'-(5-Fluoro-4-iodopyridin-2-yl)pivalohydrazide

This compound was obtained as a brown solid (91%) from 5-fluoro-2-hydrazinyl-4-iodopyridine and pivaloyl chloride following the experimental procedure described for the synthesis of Intermediate 2, step a.

d) 3-tert-Butyl-6-fluoro-7-iodo-[1,2,4]triazolo[4,3-a]pyridine

Obtained as a brownish solid (53%) from N'-(5-fluoro-4-iodopyridin-2-yl)pivalohydrazide following the experimental procedure described for the synthesis of Intermediate 2, step b.
LRMS (m/z): 338 (M+1)+.

$^1$H-NMR δ (CDCl$_3$): 1.59 (s, 9H), 8.09 (s, 1H), 8.30 (d, J=6.0 Hz, 1H).

Intermediate 20

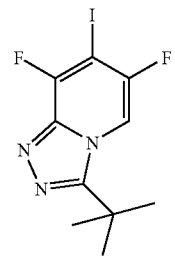

3-tert-Butyl-6,8-difluoro-7-iodo-[1,2,4]triazolo[4,3-a]pyridine a) 2,3,5-Trifluoro-4-iodopyridine This compound was obtained as a yellowish crystalline solid (84%) from 2,3,5-trifluoropyridine following the experimental procedure described for Intermediate 19, step a.

b) 3,5-Difluoro-2-hydrazinyl-4-iodopyridine

This compound was obtained as an orange solid (67%) from 2,3,5-trifluoro-4-iodopyridine following the experimental procedure described for Intermediate 1.

c) N'-(3,5-Difluoro-4-iodopyridin-2-yl)pivalohydrazide

This compound was obtained as a light yellow solid (85%) from 2-hydrazinyl-3,5-difluoro-4-iodopyridine and pivaloyl chloride following the experimental procedure described for the synthesis of Intermediate 2, step a.

d) 3-tert-Butyl-6,8-difluoro-7-iodo-[1,2,4]triazolo[4,3-a]pyridine

Obtained as an orange solid (82%) from N'-(3,5-difluoro-4-iodopyridin-2-yl)pivalohydrazide following the experimental procedure described for the synthesis of Intermediate 2, step b.
LRMS (m/z): 338 (M+1)+.

Intermediate 21

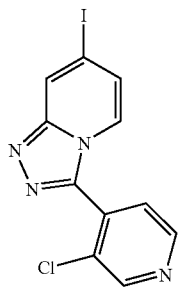

3-(3-Chloropyridin-4-yl)-7-iodo[1,2,4]triazolo[4,3-a]pyridine a) 3-Chloro-N'-(4-iodopyridin-2-yl)isonicotinohydrazide

To a mixture of 3-chloroisonicotinic acid (0.89 g, 5.48 mmol) in acetonitrile (10 mL) was added N-[3-(dimethylamino)propyl]-N'-ethylcarbodiimide hydrochloride (1.05 g, 5.50 mmol) and 1H-1,2,3-benzotriazol-1-ol (0.84 g, 5.50 mmol) and it was stirred at room temperature for 30 min. A solution of Intermediate 1 (1.30 g, 5.30 mmol) and triethyl amine (0.78 mL, 5.6 mmol) in acetonitrile (10 mL) was added during 15 min and the resulting mixture was stirred at room temperature for 1 hour. Water (40 mL) was added and the precipitate was filtered, rinsed with water and dried to yield the title compound as a yellowish solid (1.37 g, 68%).

LRMS (m/z): 375 (M+1)$^+$.

b) 3-(3-Chloropyridin-4-yl)-7-iodo[1,2,4]triazolo[4,3-a]pyridine

To a mixture of 3-chloro-N'-(4-iodopyridin-2-yl)isonicotinohydrazide (1.53 g, 4.08 mmol) and polymer supported triphenyl phosphine (2.83 g, 6.19 mmol) in tetrahydrofuran (35 mL) was added trimethylsilylazide (0.82 mL, 6.20 mmol) and a 40% solution of diethyl azodicarboxylate in toluene (3.40 mL, 7.42 mmol) and it was stirred in an orbital stirrer at room temperature for 2.5 hours. The mixture was filtered and rinsed with ethyl acetate, concentrated under reduced pressure and the resulting crude was purified by flash chromatography eluting with hexanes:isopropyl alcohol (3:2) to give the title compound (0.80 g, 55%) as a yellowish solid.

LRMS (m/z): 357 (M+1)$^+$.

$^1$H-NMR δ (CDCl$_3$): 7.17 (dd, J=6.0, 1.5 Hz, 1H), 7.59 (dd, J=6.0, 1.5 Hz, 1H), 7.66 (d, J=3.0 Hz, 1H), 8.36 (s, 1H), 8.74 (d, J=3.0 Hz, 1H), 8.85 (s, 1H).

Intermediate 22

7-Iodo-3-(tetrahydro-2H-pyran-4-yl)[1,2,4]triazolo[4,3-a]pyridine

This compound was prepared (66%) from Intermediate 1 and tetrahydro-2H-pyran-4-carboxylic acid following the experimental procedure described for the synthesis of Intermediate 21.

LRMS (m/z): 330 (M+1)$^+$.

$^1$H-NMR δ (CDCl$_3$): 1.97-2.02 (m, 1H), 2.15-2.28 (m, 2H), 3.26-3.36 (m, 1H), 3.58-3.66 (m, 2H), 4.12-4.18 (m, 1H), 7.05 (d, J=7.0 Hz, 1H), 7.71 (d, J=7.0 Hz, 1H), 8.21 (s, 1H).

Intermediate 23

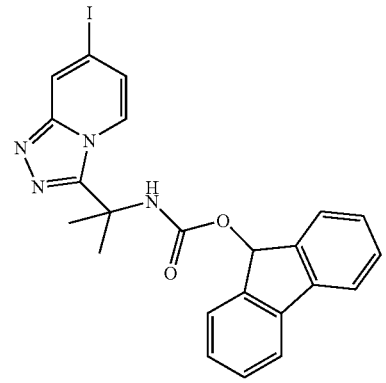

[1-(7-Iodo[1,2,4]triazolo[4,3-a]pyridin-3-yl)-1-methylethyl]amine

This compound was prepared (32%) from Intermediate 1 and N-[(9H-fluoren-9-ylmethoxy)carbonyl]-2-methylalanine following the experimental procedure described for the synthesis of Intermediate 21.

LRMS (m/z): 357 (M+1)$^+$.

$^1$H-NMR δ (DMSO-d6): 1.71 (s, 6H), 4.05-4.16 (m, 1H), 4.16-4.25 (m, 2H), 7.16 (d, J=7.1 Hz, 1H), 7.29 (t, J=7.6 Hz, 2H), 7.41 (t, J=7.4 Hz, 2H), 7.57-7.69 (m, 2H), 7.88 (d, J=7.7 Hz, 2H), 8.08 (s, 1H), 8.23 (d, J=7.4 Hz, 1H), 8.30 (s, 1H).

Intermediate 24

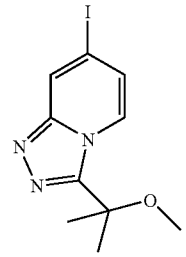

7-Iodo-3-(1-methoxy-1-methylethyl)[1,2,4]triazolo[4,3-a]pyridine

This compound was prepared (7%) from Intermediate 1 and 2-methoxy-2-methylpropanoic acid following the experimental procedure described for the synthesis of Intermediate 21.

LRMS (m/z): 318 (M+1)$^+$.

$^1$H-NMR δ (CDCl$_3$): 1.78 (s, 6H), 3.08 (s, 3H), 7.06 (dd, J=7.4, 2.8 Hz, 1H), 7.28 (s, 1H), 8.12-8.38 (m, 1H).

Intermediate 25

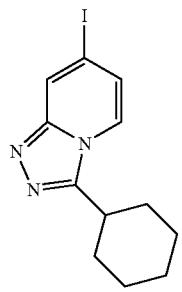

3-Cyclohexyl-7-iodo[1,2,4]triazolo[4,3-a]pyridine

This compound was prepared (60%) from Intermediate 1 and cyclohexanecarbonyl-chloride following the experimental procedure described for the synthesis of Intermediate 2.
LRMS (m/z): 328 (M+1)$^+$.
$^1$H-NMR δ (CDCl$_3$): 1.31-1.66 (m, 4H), 1.71-2.18 (m, 6H), 2.87-3.09 (m, 1H), 7.01 (d, J=7.1 Hz, 1H), 7.68 (d, J=7.4 Hz, 1H), 8.2 (s, 1H).

Intermediate 26

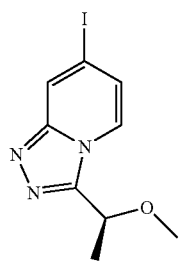

7-Iodo-3-[(1S)-1-methoxyethyl][1,2,4]triazolo[4,3-a]pyridine

This compound was prepared (50%) from Intermediate 1 and (S)-2-methoxypropionic acid following the experimental procedure described for the synthesis of Intermediate 21.
LRMS (m/z): 304 (M+1)$^+$.
$^1$H-NMR δ (CDCl$_3$): 1.70 (d, J=9.0 Hz, 3H), 3.28 (s, 3H), 5.12 (q, J=9.0 Hz, 1H), 7.04 (d, J=9.0 Hz, 1H), 8.12 (d, J=9.0 Hz, 1H), 8.22 (s, 1H).

Intermediate 27

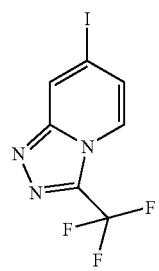

7-Iodo-3-(trifluoromethyl)[1,2,4]triazolo[4,3-a]pyridine

This compound was prepared (69%) from Intermediate 1 and trifluoroacetic anhydride following the experimental procedure described for the synthesis of Intermediate 21.
LRMS (m/z): 314 (M+1)$^+$.

Intermediate 28

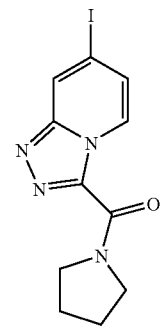

7-Iodo-3-(pyrrolidin-1-ylcarbonyl)[1,2,4]triazolo[4,3-a]pyridine a) Ethyl [2-(4-iodopyridin-2-yl)hydrazino](oxo)acetate To a solution of 2-hydraziyl-4-iodopyridine (2.00 g, 8.51 mmol) in dichloromethane (30 mL) under argon atmosphere was added diisopropylethylamine (7.50 mL, 43.10 mmol). The mixture was cooled to −78° C. and ethyl 2-chloro-2-oxoacetate (1.00 mL, 8.95 mmol) was added slowly. The resulting mixture was stirred at −78° C. for 2 hours, then water was added, extracted with dichloromethane, the combined organic layers were washed with water, brine, dried and the solvent removed under reduced pressure. The resulting crude was purified by flash chromatography eluting with hexanes/ethyl acetate (4:1) to give the title compound (0.68 g, 24%) as a yellow solid.
LRMS (m/z): 336 (M+1)$^+$.

b) [2-(4-Iodopyridin-2-yl)hydrazino](oxo)acetic acid

To a solution of ethyl [2-(4-iodopyridin-2-yl)hydrazino](oxo)acetate (0.15 g, 0.41 mmol) in tetrahydrofuran (3.5 mL) was added dropwise a solution of lithium hydroxide (0.030 g, 1.25 mmol) in water (1.5 mL). The resulting mixture was stirred at room temperature for 1 hour. Water was added and it was acidified using hydrochloric acid 2N until pH=3. The formed precipitate was filtered, rinsed with water and dried under vacuum to yield the title compound (0.20 g, 94%) as a white solid.
LRMS (m/z): 308 (M+1)$^+$.

c) N'-(4-iodopyridin-2-yl)-2-oxo-2-pyrrolidin-1-ylacetohydrazide

To a solution of [2-(4-iodopyridin-2-yl)hydrazino](oxo) acetic acid (0.64 g, 2.10 mmol) in di-methylformamide (21 mL) was added diisopropylethylamine (1.65 mL, 9.47 mmol), pyrrolidine (0.74 mL, 8.84 mmol) and finally HATU (2.40 g, 6.31 mmol). The resulting mixture was stirred at room temperature under argon atmosphere for 18 hours. The solvent was removed under reduced pressure, water was added and it was extracted with ethyl acetate. The combined organic layers were washed with brine, dried and concentrated. The crude was purified by reverse phase chromatography on a silica C18 cartridge eluting with water/acetonitrile:methanol (1:1), using a gradient from 100% water to 100% acetonitrile:methanol (1:1), to yield the title compound (0.26 g, 30%) as a white solid.
LRMS (m/z): 361 (M+1)+.

d) 7-Iodo-3-(pyrrolidin-1-ylcarbonyl)[1,2,4]triazolo[4,3-a]pyridine

This compound was prepared (90%) from N'-(4-iodopyridin-2-yl)-2-oxo-2-pyrrolidin-1-ylacetohydrazide following the experimental procedure described for the synthesis of Intermediate 21, step b.
LRMS (m/z): 343 (M+1)+.

Intermediate 29

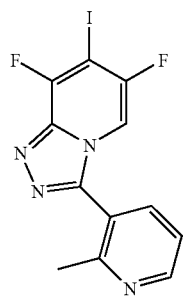

6,8-Difluoro-7-iodo-3-(3-methylpyridin-4-yl)[1,2,4]triazolo[4,3-a]pyridine

This compound was prepared (38%) from Intermediate 20b and 2-methylnicotinic acid following the experimental procedure described for the synthesis of Intermediate 21.
LRMS (m/z): 373 (M+1)+.
$^1$H-NMR δ (CDCl$_3$): 2.50 (s, 3H), 7.38 (dd, J=7.7, 4.9 Hz, 1H), 7.59 (dd, J=1.9, 1.4 Hz, 1H), 7.79 (dd, J=7.7, 1.9 Hz, 1H), 8.77 (dd, J=4.9, 1.9 Hz, 1H).

Intermediate 30

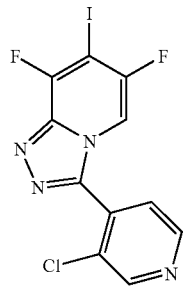

3-(3-Chloropyridin-4-yl)-6,8-difluoro-7-iodo[1,2,4]triazolo[4,3-a]pyridine

This compound was prepared (22%) from Intermediate 20b and 3-chloroisonicotinic acid following the experimental procedure described for the synthesis of Intermediate 21.
LRMS (m/z): 393 (M+1)+.

Intermediate 31

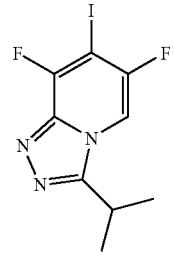

6,8-Difluoro-7-iodo-3-isopropyl[1,2,4]triazolo[4,3-a]pyridine

This compound was prepared (76%) from Intermediate 20b and isobutiryl chloride acid following the experimental procedure described for the synthesis of Intermediate 2.
LRMS (m/z): 324 (M+1)+.
$^1$H-NMR δ (CDCl$_3$): 1.59 (dd, J=6.9, 2.2 Hz, 6H), 3.27-3.51 (m, 1H), 7.83 (s, 1H).

Intermediate 32

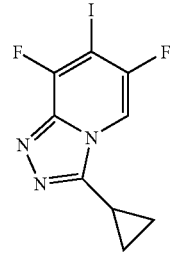

3-Cyclopropyl-6,8-difluoro-7-iodo[1,2,4]triazolo[4,3-a]pyridine a) N'-(3,5-Difluoro-4-iodopyridin-2-yl)cyclopropanecarbohydrazide This compound was obtained as a beige solid (59%) from Intermediate 20b and cyclopropanecarbonyl chloride following the experimental procedure described for Intermediate 2, step a.

b) 3-Cyclopropyl-6,8-difluoro-7-iodo[1,2,4]triazolo[4,3-a]pyridine

Obtained as a white solid (82%) from N'-(3,5-difluoro-4-iodopyridin-2-yl)pivalohydrazide following the experimental procedure described for the synthesis of Intermediate 21, step b. (Triphenylphosphine was used instead of polymer supported triphenylphosphine).

LRMS (m/z): 322 (M+1)⁺.

$^1$H-NMR δ (CDCl$_3$): 1.01-1.10 (m, 2H), 1.10-1.21 (m, 2H), 2.26-2.49 (m, 1H), 8.88 (s, 1H).

Intermediate 33

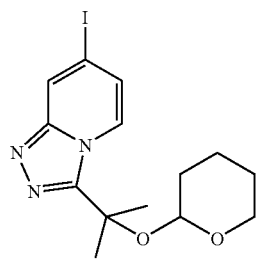

7-Iodo-3-[1-methyl-1-(tetrahydro-2H-pyran-2-yloxy)ethyl][1,2,4]triazolo[4,3-a]pyridine a) Ethyl 2-methyl-2-(tetrahydro-2H-pyran-2-yloxy)propanoate To a solution of ethyl 2-hydroxy-2-methylpropanoate (5.20 mL, 38.06 mmol) in dichloromethane (100 mL) were sequentially added pyridine 4-methylbenzenesulfonate (1.0 g, 3.80 mmol) and 3,4-dihydro-2H-pyran (5.20 ml, 57.0 mmol). The resulting mixture was stirred at room temperature overnight. Ethyl ether was added (600 mL) and the resulting organic layer was washed with brine (3×100 ml), dried over anhydrous sodium sulphate and the solvent removed under reduced pressure to give the title compound (7.85 g, 95%).

b) 2-Methyl-2-(tetrahydro-2H-pyran-2-yloxy)propanoic acid

To a solution of ethyl 2-methyl-2-(tetrahydro-2H-pyran-2-yloxy)propanoate (0.5 g, 2.31 mmol) in tetrahydrofuran (2 mL) and methanol (6 mL) was added a solution of lithium hydroxide (0.277 g, 11.56 mmol) in water (6 mL). The resulting mixture was stirred at room temperature overnight. The organic solvents were removed under reduced pressure and the resulting aqueous phase was acidified using hydrochloric acid 2N until pH=4. The formed precipitate was extracted with ethyl ether (3×25 mL). The combined organic layers were washed with brine, dried over anhydrous sodium sulphate and concentrated to yield the title compound (0.42 g, 96%) as a colourless oil.

LRMS (m/z): 187 (M−1)⁻.

c) N'-(4-iodopyridin-2-yl)-2-methyl-2-(tetrahydro-2H-pyran-2-yloxy)propanohydrazide To a solution of 2-methyl-2-(tetrahydro-2H-pyran-2-yloxy)propanoic acid (1.3 g, 6.91 mmol) and 2-hydraziyl-4-iodopyridine (1.95 g, 8.30 mmol) in dimethylformamide (30 mL) was added diisopropylethylamine (2.7 mL, 15.33 mmol) and HATU (2.52 g, 6.63 mmol). The resulting mixture was stirred at room temperature under argon atmosphere for 18 hours. The solvent was concentrated under reduced pressure, ethyl acetate was added and the resulting organic layer was washed with water, an aqueous solution of sodium bicarbonate and brine, dried over anhydrous sodium sulphate and concentrated under reduced pressure. The crude was purified by silica flash chromatography eluting with hexanes/ethyl acetate, using a gradient from 40% to 80% of ethyl acetate to yield the title compound (0.317 g, 12%) as a solid.

LRMS (m/z): 405 (M+1)⁺.

$^1$H-NMR δ (CDCl$_3$): 1.41-1.64 (m, 10H), 1.70-1.98 (m, 2H), 3.37-3.63 (m, 1H), 3.99-4.22 (m, 1H), 4.70-4.88 (m, 1H), 6.55 (s, 1H), 7.06-7.19 (m, 2H), 7.82 (d, J=5.2 Hz, 1H), 8.74 (s, 1H).

d) 7-iodo-3-[1-methyl-1-(tetrahydro-2H-pyran-2-yloxy)ethyl][1,2,4]triazolo[4,3-a]pyridine This compound was prepared (23%) from N'-(4-iodopyridin-2-yl)-2-methyl-2-(tetrahydro-2H-pyran-2-yloxy)propanohydrazide following the experimental procedure described for the synthesis of Intermediate 21, step b.

LRMS (m/z): 388 (M+1)⁺.

$^1$H-NMR δ (CDCl$_3$): 1.35-1.51 (m, 6H), 1.83 (s, 3H), 1.88 (s, 3H), 3.22-3.38 (m, 1H), 3.65-3.87 (m, 1H), 4.43-4.60 (m, 1H), 7.01 (d, J=7.7 Hz, 1H), 8.21 (s, 1H), 8.31 (d, J=7.4 Hz, 1H).

Intermediate 34

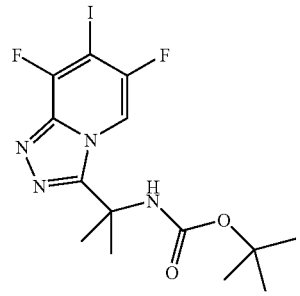

tert-Butyl [1-(6,8-difluoro-7-iodo[1,2,4]triazolo[4,3-a]pyridin-3-yl)-1-methylethyl]-carbamate a) 3,5-Difluoro-2-hydrazinopyridine This compound was obtained as a white solid (85%) from 2,3,5-trifluoropyridine following the experimental procedure described for Intermediate 19, step b.

b) tert-Butyl 1-(2-(3,5-difluoropyridin-2-yl)hydrazinyl)-2-methyl-1-oxopropan-2-ylcarbamate This compound was prepared (66%) from 3,5-difluoro-2-hydrazinopyridine and N-(tert-butoxycarbonyl)-2-methylalanine following the experimental procedure described for the synthesis of Intermediate 21, step a.

c) tert-Butyl [1-(6,8-difluoro[1,2,4]triazolo[4,3-a]pyridin-3-yl)-1-methylethyl]carbamate This compound was prepared (53%) from tert-butyl 1-(2-(3,5-difluoropyridin-2-yl)hydrazinyl)-2-methyl-1-oxopropan-2-ylcarbamate following the experimental procedure described for the synthesis of Intermediate 21, step b.

d) tert-Butyl [1-(6,8-difluoro-7-iodo[1,2,4]triazolo[4,3-a]pyridin-3-yl)-1-methylethyl]carbamate To a solution of tert-butyl [1-(6,8-difluoro[1,2,4]triazolo[4,3-a]pyridin-3-yl)-1-methylethyl]carbamate (1.32 g, 4.23 mmol) in tetrahydrofuran (20 mL) under argon atmosphere and at −78° C. was slowly added LiHMDS (1M in hexanes, 9.3 mL, 9.3 mmol). It was stirred at −78° C. for 45 min, afterwards a solution of iodine (1.13 g, 4.44 mmol) in tetrahydrofuran (10 mL) was added dropwise. The resulting mixture was stirred at −78° C. for 2 hours, warmed to 0° C. and diluted with aqueous sodium bisulphite (10 mL) and saturated ammonia chloride (10 mL). It was warmed to room temperature, extracted with ethyl acetate, dried over anhydrous sodium sulphate and concentrated under reduced pressure. The crude was purified by silica flash chromatography eluting with hexanes/ethyl acetate, using a gradient from 50% to 83% of ethyl acetate to yield the title compound (0.979 g, 53%) as a yellow solid.

LRMS (m/z): 439 (M+1)$^+$.

$^1$H-NMR δ (CDCl$_3$): 1.32 (brs, 9H), 1.91 (s, 6H), 4.03-4.51 (m, 1H), 8.36 (s, 1H).

Intermediate 35

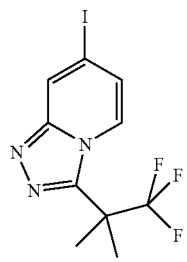

7-Iodo-3-(2,2,2-trifluoro-1,1-dimethylethyl)[1,2,4]triazolo[4,3-a]pyridine a) 3,3,3-Trifluoro-W-(4-iodopyridin-2-yl)-2,2-dimethylpropanohydrazide This compound was prepared (81%) from Intermediate 1 and 3,3,3-trifluoro-2,2-dimethylpropanoic acid following the experimental procedure described for the synthesis of Intermediate 21, step a.

b) 7-Iodo-3-(2,2,2-trifluoro-1,1-dimethylethyl)[1,2,4]triazolo[4,3-a]pyridine

This compound was prepared (80%) from 3,3,3-trifluoro-N'-(4-iodopyridin-2-yl)-2,2-dimethylpropanohydrazide following the experimental procedure described for the synthesis of Intermediate 21, step b.

LRMS (m/z): 356 (M+1)$^+$.

Intermediate 36

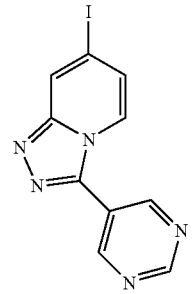

7-Iodo-3-pyrimidin-5-yl[1,2,4]triazolo[4,3-a]pyridine a) N'-(4-iodopyridin-2-yl)pyrimidine-5-carbohydrazide This compound was prepared (61%) from Intermediate 1 and pyrimidine-5-carboxylic acid following the experimental procedure described for the synthesis of Intermediate 21, step a.

b) 7-Iodo-3-pyrimidin-5-yl[1,2,4]triazolo[4,3-a]pyridine

This compound was prepared (61%) from N'-(4-iodopyridin-2-yl)pyrimidine-5-carbohydrazide following the experimental procedure described for the synthesis of Intermediate 21, step b.

LRMS (m/z): 324 (M+1)$^+$.

$^1$H-NMR δ (DMSO-d6): 7.89 (d, J=8.2 Hz, 1H), 7.96-8.03 (m, 1H), 8.05-8.20 (m, 3H), 8.28 (s, 1H).

Intermediate 37

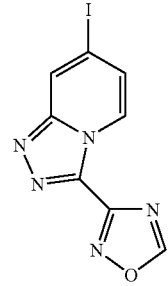

7-Iodo-3-(1,2,4-oxadiazol-3-yl)[1,2,4]triazolo[4,3-a]pyridine a) Ethyl 1,2,4-oxadiazole-3-carboxylate To a suspension of ethyl 2-(hydroxyamino)-2-iminoacetate (3 g, 22.71 mmol) in triethylorthoformate (14 mL, 84.08 mmol) was added boron trifluoride diethyl etherate (0.144 mL, 1.14 mmol). It was heated for 90 minutes. The reaction mixture was concentrated under reduced pressure and the residue dissolved in chloroform. The resulting organic layer was washed with aqueous hydrochloric acid 2N (2×80 mL), aqueous sodium bicarbonate 4% (1×80 mL) and water (2×80 mL), it was dried over anhydrous sodium sulphate and the solvent removed under reduced pressure to yield the title compound (2.70 g, 79%) as a yellow oil.

b) N'-(4-Iodopyridin-2-yl)-1,2,4-oxadiazole-3-carbohydrazide

To a solution of Intermediate 1 (4.30 g, 17.75 mmol) in ethanol (65 mL) was added dropwise) a solution of ethyl 1,2,4-oxadiazole-3-carboxylate (2.66 g, 17.78 mmol) in ethanol (10 mL) under argon. It was stirred at room temperature during 8 days. The reaction mixture was filtered and the solid obtained (1.05 g, 13%) was dried and used in the next step without further purification.

c) 7-Iodo-3-(1,2,4-oxadiazol-3-yl)[1,2,4]triazolo[4,3-a]pyridine

This compound was prepared (24%) from N'-(4-Iodopyridin-2-yl)-1,2,4-oxadiazole-3-carbohydrazide following the experimental procedure described for the synthesis of Intermediate 21, step b.
LRMS (m/z): 314 (M+1)+.

EXAMPLES

Example 1

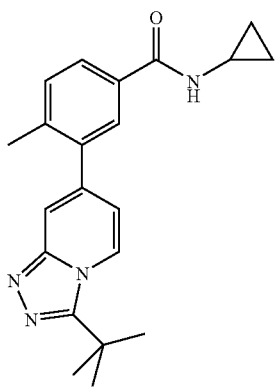

3-(3-tert-Butyl-[1,2,4]triazolo[4,3-a]pyridin-7-yl)-N-cyclopropyl-4-methylbenzamide In a Schlenk tube were charged Intermediate 2 (1.07 g, 3.56 mmol), Intermediate 11 (1.26 g, 4.18 mmol), cesium carbonate (2M aqueous solution, 5 mL, 10.0 mmol) and dioxane (60 mL). The mixture was submitted to three vacuum-argon cycles, then [1,1'-bis(diphenylphosphino)ferrocene]dichloropalladium(II) complex with dichloromethane (1:1) (168 mg, 0.206 mmol) was added and the mixture purged in the same way. The reaction was stirred at 95° C. under argon for 17 hours. Subsequently, the reaction crude was filtered through Celite® washing with ethyl acetate. This organic phase was washed with water and brine, dried over anhydrous sodium sulphate and concentrated to yield a greenish oil. This oil was taken up in ethyl acetate and was extracted with hydrochloric acid 2N (3×200 mL). The acidic aqueous phase was basified with sodium hydroxide 2N (620 mL) and extracted with dichloromethane (2×250 mL). The organic phase was dried over anhydrous sodium sulphate and concentrated to give a residue that was purified by column chromatography on silica flash, using ethyl acetate/methanol (10/0.5) as eluents, to yield the title compound (922 mg, 74%) as an off-white solid.
LRMS (m/z): 349 (M+1)+.
1H-NMR δ (CDCl3): 0.64 (m, 2H), 0.89 (m, 2H), 1.64 (s, 9H), 2.37 (s, 3H), 2.93 (m, 1H), 6.39 (brs, 1H), 6.80 (d, J=7.5 Hz, 1H), 7.37 (d, J=7.3 Hz, 1H), 7.64-7.71 (m, 3H), 8.22 (d, J=7.2 Hz, 1H).

Example 2

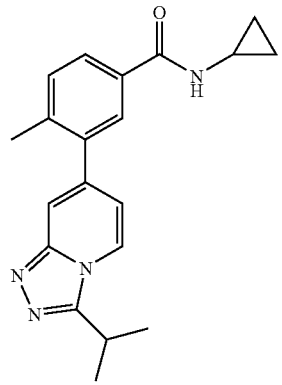

N-Cyclopropyl-3-(3-isopropyl-[1,2,4]triazolo[4,3-a]pyridin-7-yl)-4-methylbenzamide Obtained as a white solid (47%) from Intermediate 3 and Intermediate 11 following the experimental procedure described for the synthesis of Example 1.
LRMS (m/z): 335 (M+1)+.
1H-NMR δ (CDCl3): 0.65 (m, 2H), 0.88 (m, 2H), 1.57 (d, J=7.1 Hz, 6H), 2.35 (s, 3H), 2.93 (m, 1H), 3.42 (m, 1H), 6.51 (brs, 1H), 6.83 (d, J=7.1 Hz, 1H), 7.36 (d, J=7.6 Hz, 1H), 7.59 (s, 1H), 7.70 (m, 2H), 7.96 (d, J=7.6 Hz, 1H).

Example 3

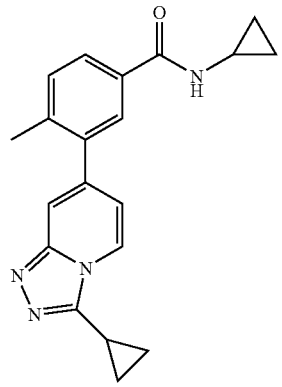

N-Cyclopropyl-3-(3-cyclopropyl-[1,2,4]triazolo[4,3-a]pyridin-7-yl)-4-methylbenzamide Obtained as a white solid (57%) from Intermediate 4 and Intermediate 11 following the experimental procedure described for the synthesis of Example 1.

LRMS (m/z): 333 (M+1)⁺.

¹H-NMR δ (CDCl₃): 0.60-0.70 (m, 2H), 0.82-0.95 (m, 2H), 1.16-1.32 (m, 4H), 2.02-2.17 (m, 1H), 2.39 (s, 3H), 2.85-3.02 (m, 1H), 6.49 (s, 1H), 6.87 (d, J=8.5 Hz, 1H), 7.36 (d, J=8.5 Hz, 1H), 7.61 (s, 1H), 7.66-7.74 (m, 2H), 8.15 (d, J=8.5 Hz, 1H).

Example 4

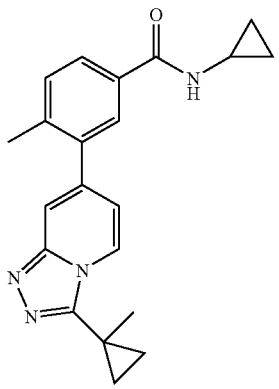

N-Cyclopropyl-4-methyl-3-(3-(1-methylcyclopropyl)-[1,2,4]triazolo[4,3-a]pyridin-7-yl)benzamide Obtained as a light yellow solid (26%) from Intermediate 5 and Intermediate 11 following the experimental procedure described for the synthesis of Example 1.

LRMS (m/z): 347 (M+1)⁺.

¹H-NMR δ (CDCl₃): 0.59-0.69 (m, 2H), 0.83-0.91 (m, 2H), 1.00 (m, 2H), 1.19-1.24 (m, 2H), 1.53 (s, 3H), 2.36 (s, 3H), 2.88-2.97 (m, 1H), 6.38 (brs, 1H), 6.86 (dd, J=7.0, 1.5 Hz, 1H), 7.37 (d, J=8.0 Hz, 1H), 7.60-7.62 (m, 1H), 7.68 (s, 1H), 7.71 (dd, J=7.0, 1.1 Hz, 1H), 8.21 (dd, J=7.0, 1.1 Hz, 1H).

Example 5

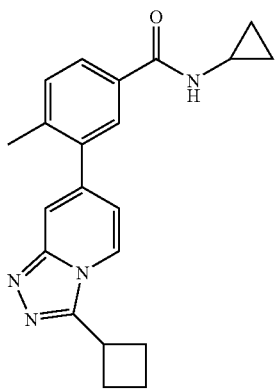

3-(3-Cyclobutyl-[1,2,4]triazolo[4,3-a]pyridin-7-yl)-N-cyclopropyl-4-methylbenzamide Obtained as a white solid (75%) from Intermediate 6 and Intermediate 11 following the experimental procedure described for the synthesis of Example 1.

LRMS (m/z): 347 (M+1)⁺.

¹H-NMR δ (CDCl₃): 0.56-0.73 (m, 2H), 0.84-0.93 (m, 2H), 2.08-2.29 (m, 2H), 2.33 (s, 3H), 2.53-2.75 (m, 4H), 2.87-2.98 (m, 1H), 3.81-4.00 (m, 1H), 6.60 (s, 1H), 6.80 (d, J=6.3 Hz, 1H), 7.35 (d, J=7.7 Hz, 1H), 7.58 (s, 1H), 7.68 (s, 1H), 7.71 (d, J=7.7 Hz, 1H), 7.83 (d, J=6.3 Hz, 1H).

Example 6

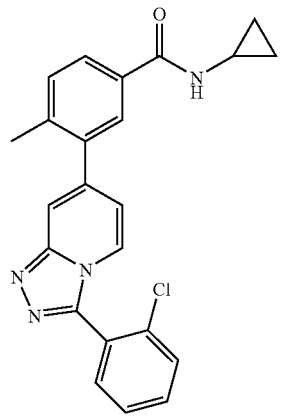

3-(3-(2-Chlorophenyl)-[1,2,4]triazolo[4,3-a]pyridin-7-yl)-N-cyclopropyl-4-methylbenzamide Obtained as a light yellow solid (15%) from Intermediate 7 and Intermediate 11 following the experimental procedure described for the synthesis of Example 1.

LRMS (m/z): 403 (M+1)⁺.

¹H-NMR δ (CDCl₃): 0.56-0.70 (m, 2H), 0.82-0.93 (m, 2H), 2.38 (s, 3H), 2.85-2.97 (m, 1H), 6.45 (s, 1H), 6.87 (d, J=7.1 Hz, 1H), 7.38 (d, J=7.7 Hz, 1H), 7.47-7.66 (m, 3H), 7.68-7.77 (m, 4H), 7.85 (d, J=7.1 Hz, 1H).

Example 7

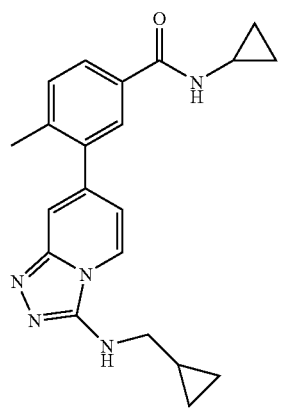

N-Cyclopropyl-3-(3-(cyclopropylmethylamino)-[1,2,4]triazolo[4,3-a]pyridin-7-yl)-4-methylbenzamide Obtained as a yellow solid (38%) from Intermediate 8 and Intermediate 11 following the experimental procedure described for the synthesis of Example 1.
LRMS (m/z): 362 (M+1)+.
1H-NMR δ (CDCl3): 0.21-0.37 (m, 2H), 0.45-0.61 (m, 4H), 0.66-0.74 (m, 2H), 1.14-1.33 (m, 1H), 2.34 (s, 3H), 2.79-2.93 (m, 1H), 3.28 (m, 2H), 6.79-6.89 (m, 1H), 7.40-7.44 (m, 2H), 7.76 (s, 1H), 7.79 (d, J=4.1 Hz, 1H), 8.20 (d, J=7.4 Hz, 1H), 8.47 (d, J=4.1 Hz, 1H).

Example 8

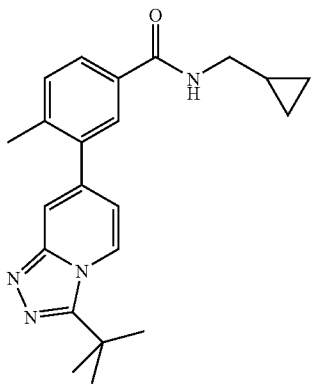

3-(3-tert-Butyl-[1,2,4]triazolo[4,3-a]pyridin-7-yl)-N-(cyclopropylmethyl)-4-methylbenzamide Obtained as a white solid (52%) from Intermediate 2 and Intermediate 13 following the experimental procedure described for the synthesis of Example 1.
LRMS (m/z): 363 (M+1)+.
1H-NMR δ (CDCl3): 0.25-0.30 (m, 2H), 0.53-0.59 (m, 2H), 1.00-1.14 (m, 1H), 1.64 (s, 9H), 2.38 (s, 3H), 3.32 (dd, J=5.5 Hz, 7.0 Hz, 2H), 6.41 (brs, 1H), 6.81 (dd, J=3.0 Hz, 9.0 Hz, 1H), 7.38 (d, J=9.0 Hz, 1H), 7.66 (dd, J=1.1 Hz, 2.1, 1H), 7.72 (d, J=3.0 Hz, 1H), 7.75 (dd, J=3.0 Hz, 9 Hz, 1H), 8.22 (dd, J=3.0 Hz, 9 Hz, 1H).

Example 9

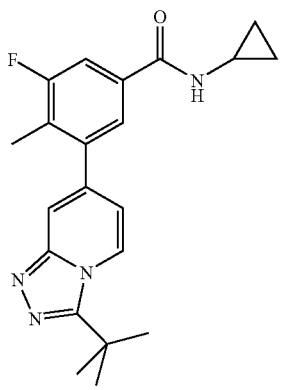

3-(3-tert-Butyl-[1,2,4]triazolo[4,3-a]pyridin-7-yl)-N-cyclopropyl-5-fluoro-4-methylbenzamide Obtained as a white solid (49%) from Intermediate 2 and Intermediate 12 following the experimental procedure described for the synthesis of Example 1.
LRMS (m/z): 367 (M+1)+.
1H-NMR δ (CDCl3): 0.63-0.67 (m, 2H), 0.82-0.87 (m, 2H), 1.59 (s, 9H), 2.23 (s, 3H), 2.91-2.97 (m, 1H), 6.76 (d, J=4.0 Hz, 1H), 7.35 (brs, 1H), 7.48 (s, 1H), 7.55 (s, 1H), 7.57 (d, J=6.0 Hz, 1H), 8.20 (d, J=6.0 Hz, 1H).

Example 10

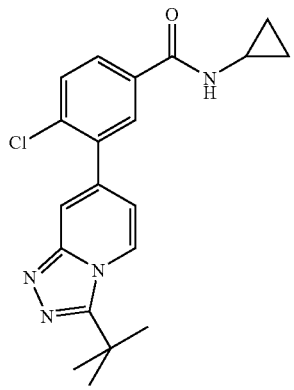

3-(3-tert-Butyl-[1,2,4]triazolo[4,3-a]pyridin-7-yl)-4-chloro-N-cyclopropylbenzamide Obtained as a white solid (72%) from Intermediate 2 and Intermediate 10, following the experimental procedure described for the synthesis of Example 1.
LRMS (m/z): 369 (M+1)+.
1H-NMR δ (CDCl3): 0.65-0.70 (m, 2H), 0.83-0.87 (m, 2H), 1.57 (s, 9H), 2.92-2.97 (m, 1H), 6.89 (d, J=4.0 Hz, 1H), 7.50 (brs, 1H), 7.54 (d, J=4.0 Hz, 1H), 7.61 (s, 1H), 7.84 (d, J=6.0 Hz, 1H), 7.87 (s, 1H), 8.15 (d, J=6.0 Hz, 1H).

Example 11

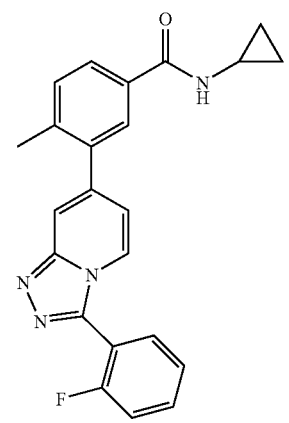

N-Cyclopropyl-3-[3-(2-fluorophenyl)-[1,2,4]triazolo[4,3-a]pyridin-7-yl]-4-methyl-benzamide This compound was prepared (22%) from Intermediate 14 and Intermediate 11 following the experimental procedure described for the synthesis of Example 1.

LRMS (m/z): 387 (M+1)+.

$^1$H-NMR δ (CDCl$_3$): 0.59-0.69 (m, 2H), 0.84-0.91 (m, 2H), 2.38 (s, 3H), 2.86-2.97 (m, 1H), 6.48 (s, 1H), 6.89 (d, J=8.0 Hz, 1H), 7.31 (d, J=8.0 Hz, 1H), 7.34-7.46 (m, 2H), 7.56-7.65 (m, 1H), 7.69-7.75 (m, 3H), 7.88 (dd, J=8.0, 8.0 Hz, 1H), 7.96-8.03 (m, 1H).

Example 12

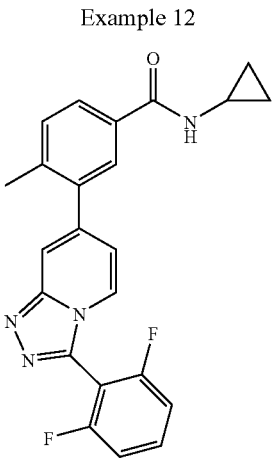

N-Cyclopropyl-3-[3-(2,6-difluorophenyl)-[1,2,4]triazolo[4,3-a]pyridin-7-yl]-4-methylbenzamide This compound was prepared (29%) from Intermediate 15 and Intermediate 11 following the experimental procedure described for the synthesis of Example 1.

LRMS (m/z): 405 (M+1)+.

$^1$H-NMR δ (CDCl$_3$): 0.55-0.69 (m, 2H), 0.82-0.94 (m, 2H), 2.38 (s, 3H), 2.84-2.97 (m, 1H), 6.49 (brs, 1H), 6.91 (dd, J=7.1, 1.4 Hz, 1H), 7.18 (t, J=7.8 Hz, 2H), 7.38 (d, J=8.5 Hz, 1H), 7.53-7.65 (m, 1H), 7.69-7.77 (m, 3H), 7.87 (d, J=8.0 Hz, 1H).

Example 13

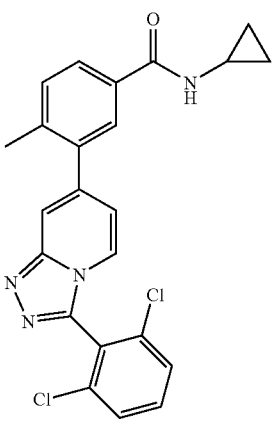

N-Cyclopropyl-3-[3-(2,6-dichlorophenyl)-[1,2,4]triazolo[4,3-a]pyridin-7-yl]-4-methylbenzamide Obtained as a yellowish solid (67%) from Intermediate 16 and Intermediate 11 following the experimental procedure described for the synthesis of Example 1.

LRMS (m/z): 437 (M+1)+.

$^1$H-NMR δ (CDCl$_3$): 0.53-0.67 (m, 2H), 0.75-0.90 (m, 2H), 2.30-2.42 (m, 3H), 2.80-2.94 (m, 1H), 6.66-6.77 (m, 1H), 6.82-6.93 (m, 1H), 7.33-7.41 (m, 1H), 7.46-7.59 (m, 3H), 7.61-7.82 (m, 4H).

Example 14

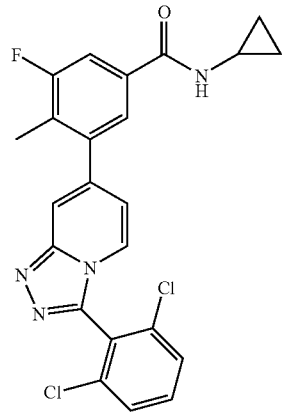

N-Cyclopropyl-3-[3-(2,6-dichlorophenyl)-[1,2,4]triazolo[4,3-a]pyridin-7-yl]-5-fluoro-4-methylbenzamide Obtained as a light yellow solid (52%) from Intermediate 16 and Intermediate 12 following the experimental procedure described for the synthesis of Example 1.

LRMS (m/z): 455 (M+1)+.

$^1$H-NMR δ (CDCl$_3$): 0.56-0.65 (m, 2H), 0.77-0.88 (m, 2H), 2.23-2.34 (m, 3H), 2.78-2.93 (m, 1H), 6.86 (dd, J=7.0, 1.6 Hz, 2H), 6.89-6.95 (m, 1H), 7.52-7.56 (m, 2H), 7.56-7.59 (m, 1H), 7.59-7.64 (m, 1H), 7.66-7.69 (m, 1H), 7.69-7.73 (m, 1H).

Example 15

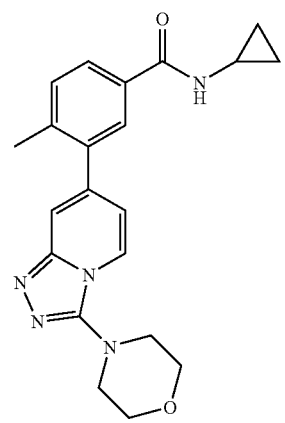

N-Cyclopropyl-4-methyl-3-(3-morpholin-4-yl-[1,2,4]triazolo[4,3-a]pyridin-7-yl)-benzamide Obtained as a white solid (62%) from Intermediate 17 and Intermediate 11 following the experimental procedure described for the synthesis of Example 1.

LRMS (m/z): 378 (M+1)+.

$^1$H-NMR δ (CDCl$_3$): 0.60-0.69 (m, 2H), 0.83-0.94 (m, 2H), 2.34 (s, 3H), 2.89-2.96 (m, 1H), 3.33-3.41 (m, 4H), 3.91-4.01 (m, 4H), 6.42 (s, 1H), 6.77 (dd, J=7.0, 1.5 Hz, 1H), 7.35 (d, J=9.0 Hz, 1H), 7.52 (s, 1H), 7.66 (d, J=7.0 Hz, 1H), 7.69 (s, 1H), 7.86 (d, J=7.0 Hz, 1H).

Example 16

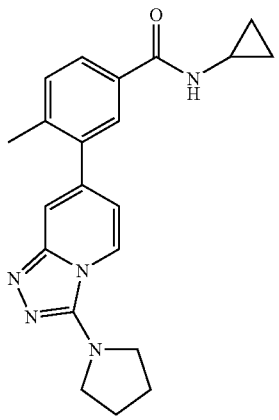

N-Cyclopropyl-4-methyl-3-(3-pyrrolidin-1-yl-[1,2,4]triazolo[4,3-a]pyridin-7-yl)-benzamide Obtained as a yellow solid (35%) from Intermediate 18 and Intermediate 11 following the experimental procedure described for the synthesis of Example 1.

LRMS (m/z): 362 (M+1)+.

$^1$H-NMR δ (CDCl$_3$): 0.64 (m, 2H), 0.84-0.93 (m, 2H), 2.03-2.12 (m, 4H), 2.35 (s, 3H), 2.87-2.96 (m, 1H), 3.60-3.69 (m, 4H), 6.41 (s, 1H), 6.64 (d, J=7.0 Hz, 1H), 7.35 (d, J=7.5 Hz, 1H), 7.42-7.43 (m, 1H), 7.66 (s, 1H), 7.66 (d, J=7.5 Hz, 1H), 7.94 (d, J=7.5 Hz, 1H).

Example 17

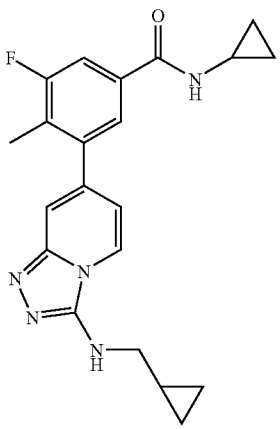

N-Cyclopropyl-3-[3-(cyclopropylmethylamino)-[1,2,4]triazolo[4,3-a]pyridin-7-yl]-5-fluoro-4-methylbenzamide Obtained as a yellow solid (38%) from Intermediate 8 and Intermediate 12 following the experimental procedure described for the synthesis of Example 1.

LRMS (m/z): 380 (M+1)+.

$^1$H-NMR δ (CDCl$_3$): 0.27-0.35 (m, 2H), 0.54-0.63 (m, 2H), 0.64-0.71 (m, 2H), 0.85-0.91 (m, 2H), 1.18-1.31 (m, 1H), 2.21 (s, 3H), 2.87-2.98 (m, 1H), 3.41 (d, J=7.0 Hz, 2H), 4.37-4.56 (m, 1H), 6.58 (d, J=7.0 Hz, 1H), 6.76 (s, 1H), 7.30 (s, 1H), 7.42 (s, 1H), 7.49 (d, J=8.0 Hz, 1H), 7.73 (d, J=7.0 Hz, 1H).

Example 18

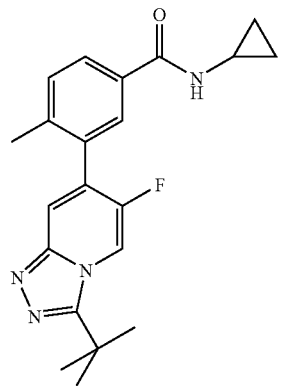

3-(3-tert-Butyl-6-fluoro-[1,2,4]triazolo[4,3-a]pyridin-7-yl)-N-cyclopropyl-4-methylbenzamide Obtained as a yellow solid (59%) from Intermediate 16 and Intermediate 11 following the experimental procedure described for the synthesis of Example 1.

LRMS (m/z): 367 (M+1)+.

$^1$H-NMR δ (CDCl$_3$): 0.58-0.68 (m, 2H), 0.84-0.91 (m, 2H), 1.64 (s, 9H), 2.30 (s, 3H), 2.86-2.96 (m, 1H), 6.36 (s, 1H), 7.38 (d, J=8.0 Hz, 1H), 7.64 (d, J=7.0 Hz, 1H), 7.67 (d, J=2.0 Hz, 1H), 7.75 (dd, J=8.0, 2.0 Hz, 1H), 8.18 (d, J=7.0 Hz, 1H).

Example 19

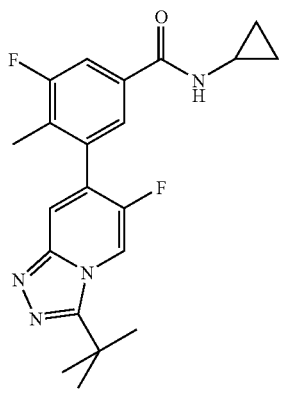

3-(3-tert-Butyl-6-fluoro-[1,2,4]triazolo[4,3-a]pyridin-7-yl)-N-cyclopropyl-5-fluoro-4-methylbenzamide Obtained as a white solid (48%) from Intermediate 19 and Intermediate 12 following the experimental procedure described for the synthesis of Example 1.

LRMS (m/z): 385 (M+1)+.

$^1$H-NMR δ (CDCl$_3$): 0.59-0.68 (m, 2H), 0.82-0.93 (m, 2H), 1.63 (s, 9H), 2.21 (s, 3H), 2.87-2.97 (m, 1H), 6.49 (s, 1H), 7.48 (s, 1H), 7.57 (d, J=8.0 Hz, 1H), 7.65 (d, J=8.0 Hz, 1H), 8.18 (d, J=8.0 Hz, 1H).

Example 20

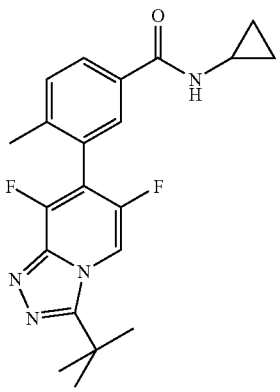

3-(3-tert-Butyl-6,8-difluoro-[1,2,4]triazolo[4,3-a]pyridin-7-yl)-N-cyclopropyl-4-methylbenzamide Obtained as a white solid (22%) from Intermediate 20 and Intermediate 11 following the experimental procedure described for the synthesis of Example 1.

LRMS (m/z): 385 (M+1)+.

$^1$H-NMR δ (CDCl$_3$): 0.51-0.61 (m, 2H), 0.65-0.75 (m, 2H), 1.56 (s, 9H), 2.26 (s, 3H), 2.78-2.90 (m, 1H), 7.52 (d, J=8.0 Hz, 1H), 7.85 (d, J=2.0 Hz, 1H), 7.90 (dd, J=8.0, 2.0 Hz, 1H), 8.46 (d, J=4.0 Hz, 1H), 9.05 (d, J=4.0 Hz, 1H).

Example 21

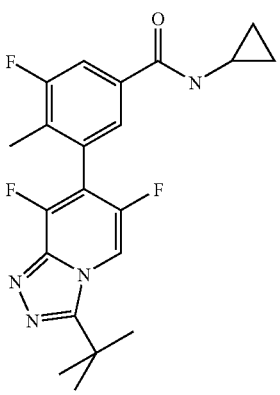

3-(3-tert-Butyl-6,8-difluoro-[1,2,4]triazolo[4,3-a]pyridin-7-yl)-N-cyclopropyl-5-fluoro-4-methylbenzamide Obtained as a white solid (23%) from Intermediate 20 and Intermediate 12 following the experimental procedure described for the synthesis of Example 1.

LRMS (m/z): 403 (M+1)+.

$^1$H-NMR δ (CDCl$_3$): 0.54-0.59 (m, 2H), 0.67-0.74 (m, 2H), 1.56 (s, 9H), 2.18 (s, 3H), 2.79-2.91 (m, 1H), 7.76 (s, 1H), 7.79 (s, 1H), 8.55 (d, J=4.5 Hz, 1H), 9.07 (d, J=4.5 Hz, 1H).

Example 22

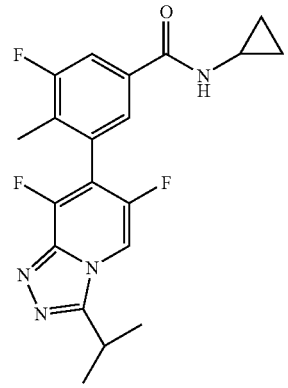

N-Cyclopropyl-3-(6,8-difluoro-3-isopropyl[1,2,4]triazolo[4,3-a]pyridin-7-yl)-5-fluoro-4-methylbenzamide Obtained as a light pink solid (54%) from Intermediate 31 and Intermediate 12 following the experimental procedure described for the synthesis of Example 1.

LRMS (m/z): 389 (M+1)+.

$^1$H-NMR δ (CDCl$_3$): 0.54-0.60 (m, 2H), 0.68-0.74 (m, 2H), 1.41-1.44 (m, 6H), 2.17 (s, 3H), 2.79-2.89 (m, 1H), 3.52-3.63 (m, 1H), 7.75 (s, 1H), 7.79 (d, J=8.0 Hz, 1H), 8.56 (d, J=4.5 Hz, 1H), 8.95 (d, J=4.5 Hz, 1H).

Example 23

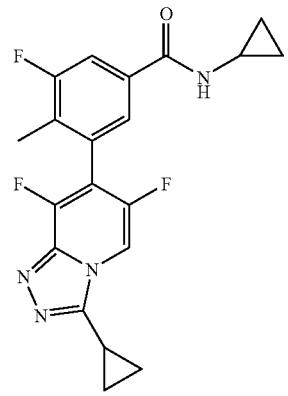

N-cyclopropyl-3-(3-cyclopropyl-6,8-difluoro[1,2,4]triazolo[4,3-a]pyridin-7-yl)-5-fluoro-4-methylbenzamide Obtained as a white solid (59%) from Intermediate 32 and Intermediate 12 following the experimental procedure described for the synthesis of Example 1.
LRMS (m/z): 387 (M+1)$^+$.
$^1$H-NMR δ (CDCl$_3$): 0.54-0.59 (m, 2H), 0.67-0.74 (m, 2H), 1.05-1.12 (m, 2H), 1.21-1.30 (m, 2H), 2.17 (s, 3H), 2.40-2.55 (m, 2H), 2.80-2.90 (m, 1H), 7.75 (s, 1H), 7.79 (d, J=8.0 Hz, 1H), 8.57 (s, 1H), 9.02 (s, 1H).

Example 24

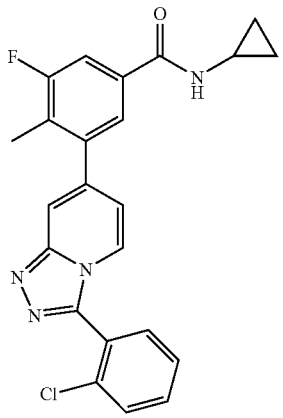

3-(3-(2-Chlorophenyl)-[1,2,4]triazolo[4,3-a]pyridin-7-yl)-N-cyclopropyl-5-fluoro-4-methylbenzamide Obtained as an off-white solid (46%) from Intermediate 7 and Intermediate 12 following the experimental procedure described for the synthesis of Example 1.
LRMS (m/z): 421 (M+1)$^+$.
$^1$H-NMR δ (CDCl$_3$): 0.61-0.65 (m, 2H), 0.84-0.94 (m, 2H), 2.29 (s, 3H), 2.87-2.94 (m, 1H), 6.55 (brs, 1H), 7.50-7.65 (m, 6H), 7.71-7.73 (m, 2H), 7.85 (d, J=9.0 Hz, 1H).

Example 25

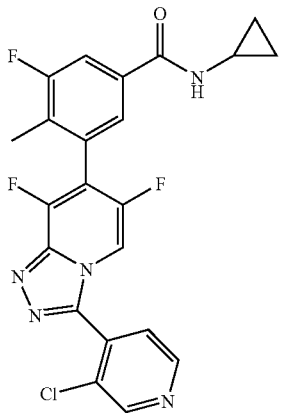

3-[3-(3-Chloropyridin-4-yl)-6,8-difluoro[1,2,4]triazolo[4,3-a]pyridin-7-yl]-N-cyclopropyl-5-fluoro-4-methylbenzamide Obtained as a white solid (32%) from Intermediate 30 and Intermediate 12 following the experimental procedure described for the synthesis of Example 1.
LRMS (m/z): 458 (M+1)$^+$.
$^1$H-NMR δ (CDCl$_3$): 0.55-0.64 (m, 2H), 0.77-0.89 (m, 2H), 2.21 (s, 3H), 2.82-2.90 (m, 1H), 6.93 (brs, 1H), 7.62-7.66 (m, 3H), 7.83 (d, J=3.0 Hz, 1H), 8.77 (d, J=6.0 Hz, 1H), 8.90 (s, 1H).

Example 26

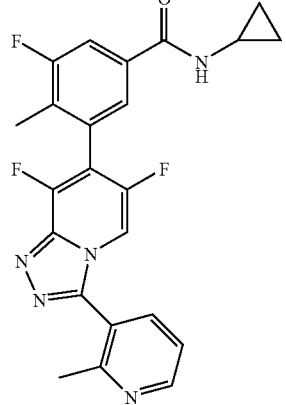

N-Cyclopropyl-3-[6,8-difluoro-3-(2-methylpyridin-3-yl)[1,2,4]triazolo[4,3-a]pyridin-7-yl]-5-fluoro-4-methylbenzamide Obtained as a white solid (27%) from Intermediate 29 and Intermediate 12 following the experimental procedure described for the synthesis of Example 1.
LRMS (m/z): 437 (M+1)$^+$.
$^1$H-NMR δ (CDCl$_3$): 0.59-0.64 (m, 2H), 0.84-0.91 (m, 2H), 2.23 (s, 3H), 2.56 (s, 3H), 2.85-2.94 (m, 1H), 6.46-6.51 (brs, 1H), 7.40 (dd, J=6.0, 3.0 Hz, 1H), 7.58 (s, 1H), 7.61 (s, 1H), 7.73 (dd, J=6.0, 3.0 Hz, 1H), 7.83 (dd, J=6.0, 3.0 Hz, 1H), 8.79 (dd, J=6.0, 3.0 Hz, 1H).

Example 27

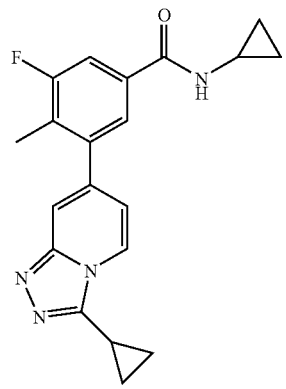

N-cyclopropyl-3-(3-cyclopropyl[1,2,4]triazolo[4,3-a]pyridin-7-yl)-5-fluoro-4-methylbenzamide Obtained as a white solid (84%) from Intermediate 4 and Intermediate 12 following the experimental procedure described for the synthesis of Example 1.

LRMS (m/z): 351 (M+1)$^+$.

$^1$H-NMR δ (CDCl$_3$): 0.60-0.69 (m, 2H), 0.84-0.93 (m, 2H), 1.17-1.29 (m, 4H), 2.02-2.16 (m, 1H), 2.25 (s, 3H), 2.87-2.97 (m, 1H), 6.50 (brs, 1H), 6.83 (d, J=7.0 Hz, 1H), 7.49-7.53 (m, 2H), 7.58 (s, 1H), 8.16 (d, J=7.0 Hz, 1H).

Example 28

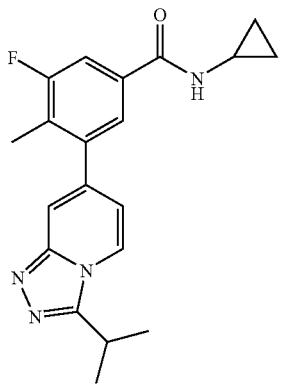

N-cyclopropyl-3-fluoro-5-(3-isopropyl[1,2,4]triazolo[4,3-a]pyridin-7-yl)-4-methylbenzamide Obtained as a white solid (75%) from Intermediate 3 and Intermediate 12 following the experimental procedure described for the synthesis of Example 1.

LRMS (m/z): 353 (M+1)$^+$.

$^1$H-NMR δ (CDCl$_3$): 0.62-0.67 (m, 2H), 0.86-0.92 (m, 2H), 1.57 (d, J=6.0 Hz, 6H), 2.25 (s, 3H), 2.88-2.97 (m, 1H), 3.38-3.52 (m, 1H), 6.48 (brs, 1H), 6.81 (dd, J=9.0, 1.5 Hz, 1H), 7.48-7.52 (m, 2H), 7.61 (s, 1H), 7.97 (d, J=9.0 Hz, 1H).

Example 29

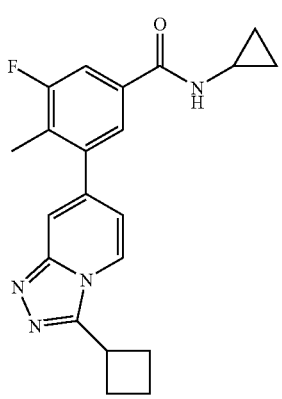

3-(3-Cyclobutyl[1,2,4]triazolo[4,3-a]pyridin-7-yl)-N-cyclopropyl-5-fluoro-4-methylbenzamide Obtained as a white solid (73%) from Intermediate 6 and Intermediate 12 following the experimental procedure described for the synthesis of Example 1.

LRMS (m/z): 365 (M+1)$^+$.

$^1$H-NMR δ (CDCl$_3$): 0.60-0.70 (m, 2H), 0.84-0.94 (m, 2H), 1.19-1.26 (m, 1H), 2.25 (s, 3H), 2.52-2.75 (m, 6H), 3.84-3.96 (m, 1H), 6.48 (brs, 1H), 6.78 (d, J=6.0 Hz, 1H), 7.48-7.52 (m, 2H), 7.60 (s, 1H), 7.84 (d, J=9.0 Hz, 1H).

Example 30

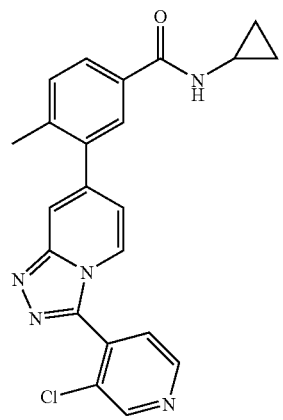

3-[3-(3-Chloropyridin-4-yl)[1,2,4]triazolo[4,3-a]pyridin-7-yl]-N-cyclopropyl-4-methylbenzamide Obtained as an off-white solid (83%) from Intermediate 30 and Intermediate 11 following the experimental procedure described for the synthesis of Example 1.

LRMS (m/z): 404 (M+1)$^+$.

$^1$H-NMR δ (CDCl$_3$): 0.61-0.67 (m, 2H), 0.86-0.92 (m, 2H), 2.39 (s, 3H), 2.88-2.97 (m, 1H), 6.36 (brs, 1H), 6.97 (d, J=7.0 Hz, 1H), 7.39 (d, J=7.0 Hz, 1H), 7.69-7.76 (m, 3H), 7.81 (s, 1H), 7.90 (d, J=8.0 Hz, 1H), 8.76 (d, J=7.0 Hz, 1H).

Example 31

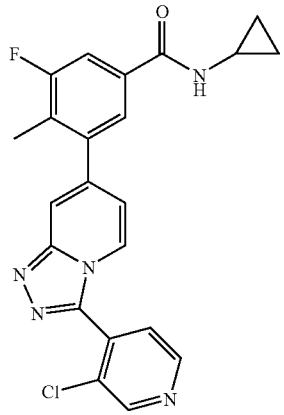

3-[3-(3-Chloropyridin-4-yl)[1,2,4]triazolo[4,3-a]pyridin-7-yl]-N-cyclopropyl-5-fluoro-4-methylbenzamide Obtained as a white solid (57%) from Intermediate 30 and Intermediate 12 following the experimental procedure described for the synthesis of Example 1.
LRMS (m/z): 422 (M+1)$^+$.
$^1$H-NMR δ (CDCl$_3$): 0.62-0.67 (m, 2H), 0.87-0.93 (m, 2H), 2.30 (s, 3H), 2.86-2.97 (m, 1H), 6.34 (brs, 1H), 6.95 (dd, J=7.0, 1.5 Hz, 1H), 7.50-7.53 (m, 2H), 7.72 (d, J=6.0 Hz, 1H), 7.82 (t, J=1.5 Hz, 1H), 7.92 (dd, J=7.0, 1.5 Hz, 1H), 8.77 (d, J=6.0 Hz, 1H), 8.89 (s, 1H).

Example 32

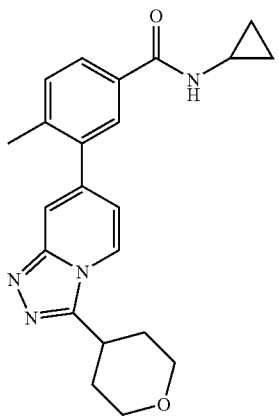

N-Cyclopropyl-4-methyl-3-[3-(tetrahydro-2H-pyran-4-yl)[1,2,4]triazolo[4,3-a]pyridin-7-yl]benzamide Obtained as a white solid (94%) from Intermediate 22 and Intermediate 11 following the experimental procedure described for the synthesis of Example 1.
LRMS (m/z): 377 (M+1)$^+$.
$^1$H-NMR δ (CD$_3$OD): 0.61-0.66 (m, 2H), 0.77-0.84 (m, 2H), 2.02-2.15 (m, 4H), 2.81-2.90 (m, 1H), 3.57-3.77 (m, 3H), 4.11 (d, J=12 Hz, 2H), 7.08 (d, J=6.0 Hz, 2H), 7.44 (d, J=6.0 Hz, 1H), 7.66 (s, 1H), 7.77 (s, 1H), 7.78 (d, J=9.0 Hz, 1H), 8.52 (d, J=9.0 Hz, 1H).

Example 33

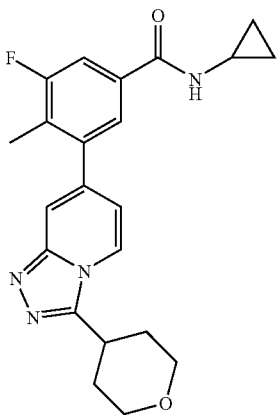

N-Cyclopropyl-3-fluoro-4-methyl-5-[3-(tetrahydro-2H-pyran-4-yl)[1,2,4]triazolo[4,3-a]pyridin-7-yl]benzamide Obtained as a beige solid (87%) from Intermediate 22 and Intermediate 12 following the experimental procedure described for the synthesis of Example 1.
LRMS (m/z): 395 (M+1)$^+$.
$^1$H-NMR δ (CD$_3$OD): 0.62-0.68 (m, 2H), 0.78-0.87 (m, 2H), 2.03-2.16 (m, 4H), 2.30 (s, 3H), 2.82-2.93 (m, 1H), 3.56-3.79 (m, 3H), 4.10-4.14 (m, 2H), 7.07-7.13 (m, 1H), 7.59-7.74 (m, 3H), 8.54-8.59 (m, 1H).

Example 34

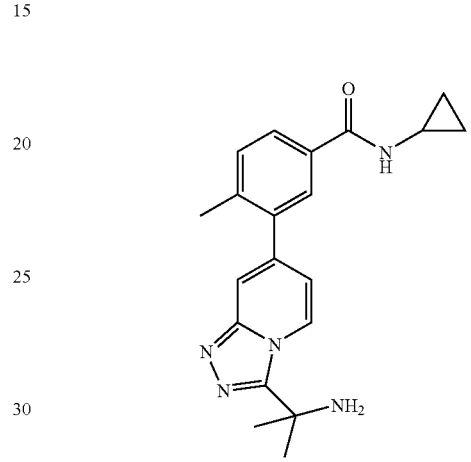

3-[3-(1-Amino-1-methylethyl)[1,2,4]triazolo[4,3-a]pyridin-7-yl]-N-cyclopropyl-4-methylbenzamide Obtained as an off-white solid (45%) from Intermediate 23 and Intermediate 11 following the experimental procedure described for the synthesis of Example 1.
LRMS (m/z): 350 (M+1)$^+$.
$^1$H-NMR δ (CDCl$_3$): 0.61-0.67 (m, 2H), 0.85-0.92 (m, 2H), 1.80 (s, 6H), 2.36 (s, 3H), 2.87-2.98 (m, 1H), 6.44 (brs, 1H), 6.75 (d, J=9.0 Hz, 1H), 7.36 (d, J=6.0 Hz, 1H), 7.59 (s, 1H), 7.68 (s, 1H), 7.69 (d, J=9.0 Hz, 1H), 9.05 (d, J=9.0 Hz, 1H).

Example 35

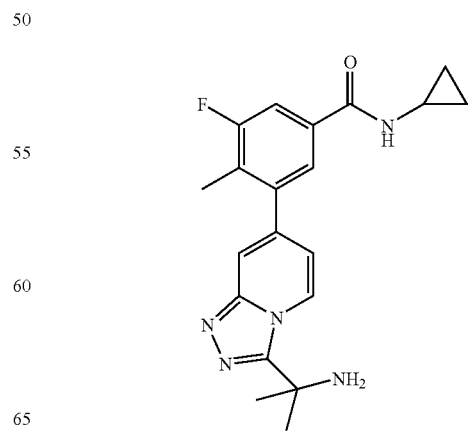

3-[3-(1-Amino-1-methylethyl)[1,2,4]triazolo[4,3-a]pyridin-7-yl]-N-cyclopropyl-5-fluoro-4-methylbenzamide Obtained as a beige solid (45%) from Intermediate 23 and Intermediate 12 following the experimental procedure described for the synthesis of Example 1.

LRMS (m/z): 367 (M+1)$^+$.

$^1$H-NMR δ (CDCl$_3$): 0.62-0.67 (m, 2H), 0.86-0.92 (m, 2H), 1.80 (s, 3H), 2.26 (s, 3H), 2.87-2.96 (m, 1H), 6.40 (brs, 1H), 6.73 (d, J=9.0 Hz, 1H), 7.46 (s, 1H), 7.50 (d, J=9.0 Hz, 1H), 7.61 (s, 1H), 9.03 (d, J=9.0 Hz, 1H).

Example 36

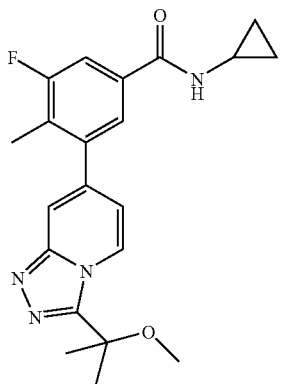

N-Cyclopropyl-3-[3-(1-methoxy-1-methylethyl)[1,2,4]triazolo[4,3-a]pyridin-7-yl]-5-fluoro-4-methylbenzamide Obtained as an off-white solid (40%) from Intermediate 24 and Intermediate 12 following the experimental procedure described for the synthesis of Example 1.

LRMS (m/z): 383 (M+1)$^+$.

$^1$H-NMR δ (CDCl$_3$): 0.61-0.67 (m, 2H), 0.86-0.92 (m, 2H), 1.84 (s, 6H), 2.28 (s, 3H), 2.87-2.95 (m, 1H), 3.14 (s, 3H), 6.34 (bs, 1H), 6.82 (d, J=6.0 Hz, 1H), 7.47 (s, 1H), 7.51 (d, J=9.0 Hz, 1H), 7.70 (s, 1H), 8.57 (d, J=9.0 Hz, 1H).

Example 37

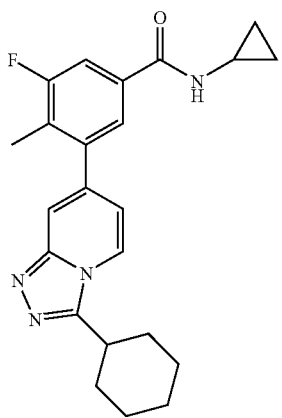

3-(3-Cyclohexyl[1,2,4]triazolo[4,3-a]pyridin-7-yl)-N-cyclopropyl-5-fluoro-4-methylbenzamide Obtained as an off-white solid (76%) from Intermediate 25 and Intermediate 12 following the experimental procedure described for the synthesis of Example 1.

LRMS (m/z): 393 (M+1)$^+$.

$^1$H-NMR δ (CDCl$_3$): 0.61-0.68 (m, 2H), 0.86-0.92 (m, 2H), 1.40-1.54 (m, 2H), 1.79-2.03 (m, 6H), 2.11-2.16 (m, 2H), 2.25 (s, 3H), 2.88-2.96 (m, 1H), 2.99-3.15 (m, 1H), 6.48 (s, 1H), 6.78 (d, J=9.0 Hz, 1H), 7.48 (s, 1H), 7.50 (d, J=9.0 Hz, 1H), 7.60 (s, 1H), 7.99 (d, J=9.0 Hz, 1H).

Example 38

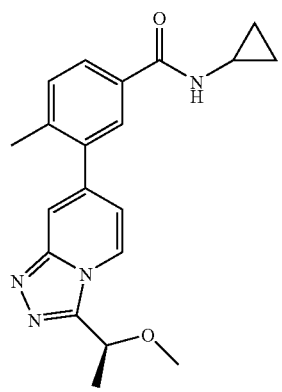

N-Cyclopropyl-3-{3-[(1S)-1-methoxyethyl][1,2,4]triazolo[4,3-a]pyridin-7-yl}-4-methylbenzamide Obtained as a white solid (34%) from Intermediate 26 and Intermediate 11 following the experimental procedure described for the synthesis of Example 1.

LRMS (m/z): 351 (M+1)$^+$.

$^1$H-NMR δ (CDCl$_3$): 0.61-0.66 (m, 2H), 0.86-0.92 (m, 2H), 1.65 (s, 3H), 1.77 (d, J=6.0 Hz, 3H), 2.37 (s, 3H), 2.88-2.98 (m, 1H), 3.34 (s, 3H), 5.18 (q, J=6.0 Hz, 1H), 6.37 (s, 1H), 6.83 (d, J=6.0 Hz, 1H), 7.37 (d, J=9.0 Hz, 1H), 7.65 (s, 1H), 7.70 (d, J=6.0 Hz, 1H), 8.40 (d, J=6.0 Hz, 1H).

Example 39

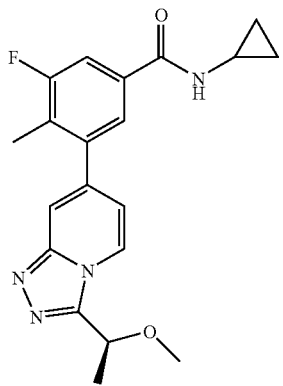

N-Cyclopropyl-3-fluoro-5-{3-[(1S)-1-methoxyethyl][1,2,4]triazolo[4,3-a]pyridin-7-yl}-4-methylbenzamide Obtained as a white solid (38%) from Intermediate 26 and Intermediate 12 following the experimental procedure described for the synthesis of Example 1.

LRMS (m/z): 351 (M+1)+.

¹H-NMR δ (CDCl₃): 0.62-0.67 (m, 2H), 0.85-0.92 (m, 2H), 1.68 (s, 3H), 1.77 (d, J=6.0 Hz, 3H), 2.27 (s, 3H), 2.88-2.97 (m, 1H), 3.34 (s, 3H), 5.17 (q, J=6.0 Hz, 1H), 6.53 (s, 1H), 6.80 (d, J=9.0 Hz, 1H), 7.50 (s, 1H), 7.52 (d, J=9.0 Hz, 1H), 7.63 (s, 1H), 8.41 (d, J=9.0 Hz, 1H).

Example 40

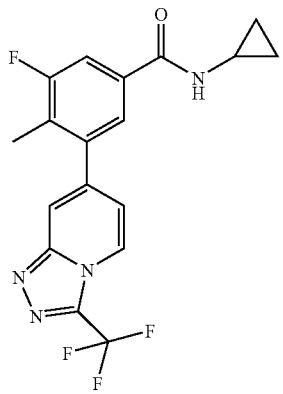

N-Cyclopropyl-3-fluoro-4-methyl-5-[3-(trifluoromethyl)[1,2,4]triazolo[4,3-a]pyridin-7-yl]benzamide Obtained as a beige solid (50%) from Intermediate 27 and Intermediate 12 following the experimental procedure described for the synthesis of Example 1.

LRMS (m/z): 421 (M+1)+.

¹H-NMR δ (CDCl₃): 0.61-0.69 (m, 2H), 0.84-0.95 (m, 2H), 1.93 (s, 6H), 2.28 (s, 3H), 2.88-2.98 (m, 1H), 6.33 (s, 1H), 6.85 (d, J=9.0 Hz, 1H), 7.48 (s, 1H), 7.52 (d, J=9.0 Hz, 1H), 7.73 (s, 1H), 8.32 (d, J=6.0 Hz, 1H).

Example 41

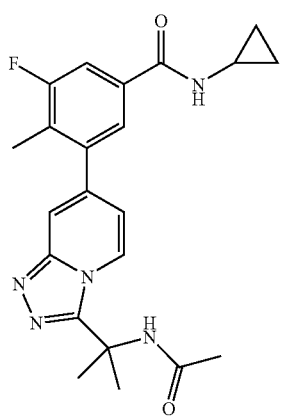

3-{3-[1-(Acetylamino)-1-methylethyl][1,2,4]triazolo[4,3-a]pyridin-7-yl}-N-cyclopropyl-5-fluoro-4-methylbenzamide To a solution of Example 35 (0.20 g, 0.55 mmol) in dichloromethane (3 mL) under argon atmosphere was added triethylamine (0.15 mL, 0.73 mmol) and acetic anhydride (0.078 mL, 0.82 mmol). The reaction mixture was stirred for 5 hours, washed with water and an aqueous saturated solution of ammonium chloride, extracted with dichloromethane and the solvent was removed under reduced pressure. The resulting crude was purified by reverse phase chromatography on a C18 cartridge eluting with water/acetonitrile:methanol (1:1), using a gradient from 100% water to 100% acetonitrile:methanol (1:1), to yield the title compound (47%) as a white solid.

LRMS (m/z): 410 (M+1)+.

¹H-NMR δ (CD₃OD): 0.61-0.66 (m, 2H), 0.78-0.84 (m, 2H), 1.87 (s, 6H), 1.96 (s, 3H), 2.29 (s, 3H), 2.82-2.89 (m, 1H), 7.05 (d, J=6.0 Hz, 1H), 7.61 (d, J=9.0 Hz, 1H), 7.63 (s, 1H), 7.71 (s, 1H), 8.51 (d, J=9.0 Hz, 1H).

Example 42

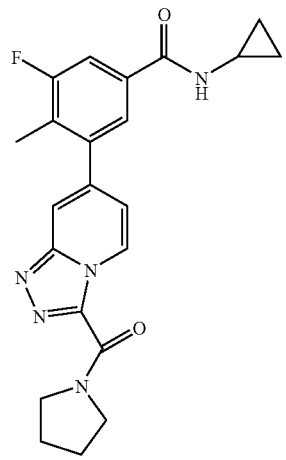

N-Cyclopropyl-3-fluoro-4-methyl-5-[3-(pyrrolidin-1-ylcarbonyl)[1,2,4]triazolo[4,3-a]pyridin-7-yl]benzamide Obtained as a white solid (30%) from Intermediate 28 and Intermediate 12 following the experimental procedure described for the synthesis of Example 1.

LRMS (m/z): 408 (M+1)+.

¹H-NMR δ (CDCl₃): 0.62-0.68 (m, 2H), 0.86-0.93 (m, 2H), 1.97-2.14 (m, 4H), 2.26 (s, 3H), 2.89-2.96 (m, 1H), 3.79 (t, J=7.0 Hz, 2H), 4.31 (t, J=7.0 Hz, 2H), 6.30-6.36 (brs, 1H), 6.96 (d, J=6.0 Hz, 1H), 7.48 (s, 1H), 7.52 (d, J=9.0 Hz, 1H), 7.77 (s, 1H), 9.44 (d, J=9.0 Hz, 1H).

Example 43

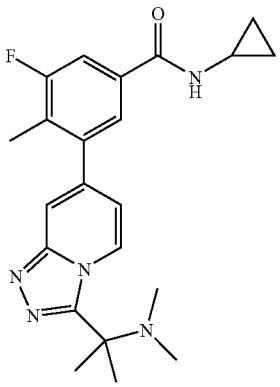

N-Cyclopropyl-3-{3-[1-(dimethylamino)-1-methyl-ethyl][1,2,4]triazolo[4,3-a]pyridin-7-yl}-5-fluoro-4-methylbenzamide To a solution of Example 35 (027 g, 0.73 mmol) in dichloroethane (3 mL) under argon atmosphere was added formaldehyde (0.067 mL, 0.89 mmol) followed by sodium triacetoxy-borohydride (0.28 g, 1.28 mmol) and the resulting mixture was stirred at room temperature for 2 hours. A saturated aqueous sodium bicarbonate solution was added and it was extracted with ethyl acetate. The combined organic layers were dried, filtered and the solvent was removed under reduced pressure. The resulting crude was purified by reverse phase chromatography on a C18 cartridge eluting with water/acetonitrile:methanol (1:1), using a gradient from 100% water to 100% acetonitrile:methanol (1:1), to yield the title compound (39%) as a white solid.

LRMS (m/z): 396 (M+1)$^+$.

$^1$H-NMR δ (CDCl$_3$): 0.60-0.67 (m, 2H), 0.85-0.92 (m, 2H), 1.63 (s, 6H), 2.22 (s, 6H), 2.27 (s, 3H), 2.88-2.97 (m, 1H), 6.59 (brs, 1H), 6.72 (d, J=9.0 Hz, 1H), 7.48 (s, 1H), 7.53 (d, J=9.0 Hz, 1H), 7.63 (s, 1H), 8.96 (d, J=9.0 Hz, 1H).

Example 44

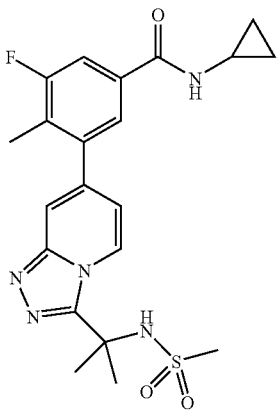

N-Cyclopropyl-3-fluoro-4-methyl-5-(3-{1-methyl-1-[(methylsulfonyl)amino]ethyl}[1,2,4]triazolo[4,3-a]pyridin-7-yl)benzamide To a solution of Example 35 (0.20 g, 0.54 mmol) in dichloromethane (5 mL) under argon atmosphere was added triethylamine (0.152 mL, 1.09 mmol) and methanesulfonyl chloride (0.063 mL, 0.82 mmol). The resulting mixture was stirred at room temperature overnight. More triethylamine (0.152 mL, 1.09 mmol) and methanesulfonyl chloride (0.063 mL, 0.82 mmol) were added and the mixture stirred at room temperature for one additional night. The mixture was washed with saturated aqueous ammonium chloride (1 mL) and water (2 mL). The organic layer was separated and the aqueous layer was concentrated and purified by reverse phase chromatography on a C18 cartridge eluting with water/acetonitrile:methanol (1:1), using a gradient from 100% water to 100% acetonitrile:methanol (1:1), to yield the title compound (17%) as a white solid.

LRMS (m/z): 446 (M+1)$^+$.

$^1$H-NMR δ (CD$_3$OD): 0.54-0.71 (m, 2H), 0.72-0.86 (m, J=5.8 Hz, 2H), 1.96 (s, 6H), 2.30 (s, 3H), 2.85 (brs, 1H), 3.06 (s, 3H), 7.04-7.17 (m, 1H), 7.54-7.82 (m, 3H), 8.85 (brs, 1H).

Example 45

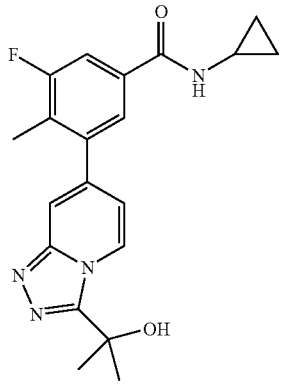

N-Cyclopropyl-3-fluoro-5-[3-(1-hydroxy-1-methyl-ethyl)[1,2,4]triazolo[4,3-a]pyridin-7-yl]-4-methyl-benzamide a) N-Cyclopropyl-3-fluoro-4-methyl-5-{3-[1-methyl-1-(tetrahydro-2H-pyran-2-yloxy)ethyl][1,2,4]triazolo[4,3-a]pyridin-7-yl}benzamide Obtained as a solid (42%) from Intermediate 33 and Intermediate 12 following the experimental procedure described for the synthesis of Example 1.

LRMS (m/z): 453 (M+1)$^+$.

$^1$H-NMR δ (CDCl$_3$): 0.57-0.75 (m, 2H), 0.79-0.96 (m, 2H), 1.38-1.66 (m, 6H), 1.84 (s, 3H), 1.91 (s, 3H), 2.26 (s, 3H), 2.79-3.04 (m, 1H), 3.22-3.45 (m, 1H), 3.74-3.93 (m, 1H), 4.46-4.61 (m, 1H), 6.68-6.88 (m, 2H), 7.43-7.57 (m, 2H), 7.60 (s, 1H), 8.59 (d, J=7.4 Hz, 1H).

b) N-Cyclopropyl-3-fluoro-5-[3-(1-hydroxy-1-methylethyl)[1,2,4]triazolo[4,3-a]pyridin-7-yl]-4-methyl-benzamide To a solution of N-cyclopropyl-3-fluoro-4-methyl-5-{3-[1-methyl-1-(tetrahydro-2H-pyran-2-yloxy)ethyl][1,2,4]triazolo[4,3-a]pyridin-7-yl}benzamide (0.065 g, 0.14 mmol) in methanol (1 mL) was added 4-methylbenzenesulfonic acid hydrate (0.010 mg, 0.06 mmol). The reaction mixture was stirred at room temperature for 5 hours, the solvent was concentrated under reduced pressure and the oil obtained was dissolved in ethyl acetate. The organic layer was washed with an aqueous solution of sodium bicarbonate and brine, dried over anhydrous sodium sulphate and concentrated. The crude was treated with diethyl ether to obtain the title compound (78%) as a solid.

LRMS (m/z): 369 (M+1)+.

$^1$H-NMR δ (CD$_3$OD): 0.51-0.66 (m, 2H), 0.69-0.85 (m, 2H), 1.76 (s, 6H), 2.30 (s, 3H), 2.81-2.99 (m, 1H), 5.96 (s, 1H), 7.09 (d, J=9.1 Hz, 1H), 7.66-7.77 (m, 2H), 7.85 (s, 1H), 8.59 (d, J=3.9 Hz, 1H), 8.84 (d, J=7.1 Hz, 1H)

Example 46

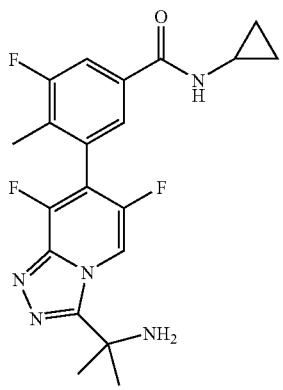

3-[3-(1-Amino-1-methylethyl)-6,8-difluoro[1,2,4]triazolo[4,3-a]pyridin-7-yl]-N-cyclopropyl-5-fluoro-4-methylbenzamide a) tert-Butyl [1-(7-{5-[(cyclopropylamino)carbonyl]-3-fluoro-2-methylphenyl}-6,8-difluoro[1,2,4]triazolo[4,3-a]pyridin-3-yl)-1-methylethyl]carbamate Obtained as a white solid (40%) from Intermediate 34 and Intermediate 12 following the experimental procedure described for the synthesis of Example 1:

LRMS (m/z): 468 (M+1)+.

$^1$H-NMR δ (CDCl$_3$): 0.52-0.60 (m, 2H), 0.65-0.75 (m, 2H), 1.21 (brs, 9H), 1.73 (d, J=3.6 Hz, 6H), 2.13 (s, 3H), 2.74-2.91 (m, 1H), 7.76 (s, 1H), 7.80 (d, J=10.4 Hz, 1H), 8.57 (d, J=3.9 Hz, 1H), 8.76 (d, J=4.1 Hz, 1H).

b) 3-[3-(1-Amino-1-methylethyl)-6,8-difluoro[1,2,4]triazolo[4,3-a]pyridin-7-yl]-N-cyclo-propyl-5-fluoro-4-methylbenzamide To a solution of tert-butyl [1-(7-{5-[(cyclopropylamino)carbonyl]-3-fluoro-2-methylphenyl}[1,2,4]triazolo[4,3-a]pyridin-3-yl)-1-methylethyl]carbamate (0.160 g, 0.28 mmol) in tetrahydrofuran (2.5 mL) was added concentrated hydrochloric acid (2.5 mL). The reaction mixture was stirred at room temperature for 90 min, it was neutralised with aqueous potassium carbonate until basic pH and extracted with dichloromethane. The organic layer was dried with a phase separator and concentrated under reduced pressure. The crude was purified with silica C18 chromatography eluting with acetonitrile/water, using a gradient from 5% to 70% of acetonitrile to yield the title compound (0.114 g, 41%) as a yellow solid.

LRMS (m/z): 404 (M+1)+.

$^1$H-NMR δ (CDCl$_3$): 0.69 (brs, 2H), 0.91 (brs, 2H), 1.83 (s, 6H), 2.23 (s, 3H), 2.96 (brs, 1H), 7.09 (brs, 1H), 7.62 (s, 1H), 7.68 (d, J=9.6 Hz, 1H), 9.13 (s, 1H).

Example 47

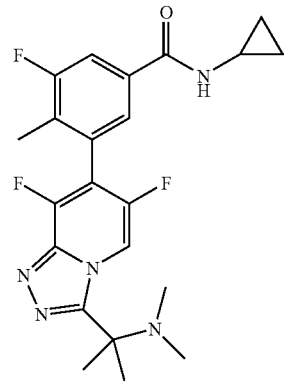

N-Cyclopropyl-3-{3-[1-(dimethylamino)-1-methylethyl]-6,8-difluoro[1,2,4]triazolo-[4,3-a]pyridin-7-yl}-5-fluoro-4-methylbenzamide To a suspension of Example 46 (0.129 g, 0.32 mmol) in dichloroethane (3 mL) were sequentially added paraformaldehyde (0.052 mL, 0.69 mmol) and sodium triacetoxyborohydride (0.170 g, 0.8 mmol). The reaction mixture was stirred at room temperature for 2.5 hours. Aqueous saturated sodium bicarbonate was added and it was extracted with ethyl acetate. The combined organic layers were dried over anhydrous sodium sulphate and concentrated under reduced pressure. The crude was purified by silica C18 chromatography eluting with acetonitrile:methanol (1:1)/water, using a gradient from 0% to 100% of acetonitrile:methanol (1:1) to yield the title compound (0.134 g, 54%) as a white solid.

LRMS (m/z): 432 (M+1)+.

$^1$H-NMR δ (CDCl$_3$): 0.52-0.70 (m, 2H), 0.79-0.97 (m, 2H), 1.63 (d, J=4.9 Hz, 6H), 2.11-2.29 (m, 9H), 2.77-3.02 (m, 1H), 6.61 (brs, 1H), 7.53 (s, 1H), 7.61 (d, J=9.9 Hz, 1H), 8.88-8.99 (m, 1H).

Example 48

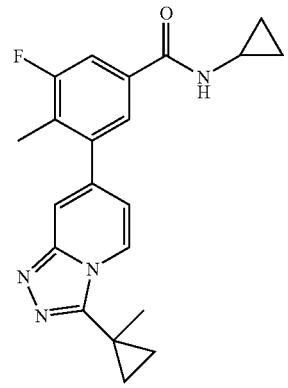

N-Cyclopropyl-3-fluoro-4-methyl-5-[3-(1-methylcyclopropyl)[1,2,4]triazolo[4,3-a]pyridin-7-yl]benzamide Obtained as a beige solid (70%) from Intermediate 5 and Intermediate 12 following the experimental procedure described for the synthesis of Example 1.

LRMS (m/z): 401 (M+1)+.

1H-NMR δ (CDCl3): 0.55-0.71 (m, 2H), 0.80-0.95 (m, 2H), 0.96-1.07 (m, 2H), 1.14-1.31 (m, 2H), 1.55 (s, 3H), 2.26 (s, 3H), 2.84-3.00 (m, 1H), 6.46 (brs, 1H), 6.84 (d, J=6.9 Hz, 1H), 7.40-7.56 (m, 2H), 7.60 (s, 1H), 8.22 (d, J=7.1 Hz, 1H).

Example 49

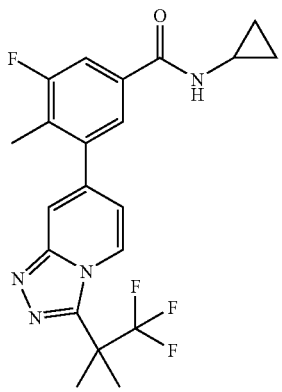

N-Cyclopropyl-3-fluoro-4-methyl-5-[3-(2,2,2-trifluoro-1,1-dimethylethyl)[1,2,4]triazolo-[4,3-a]pyridin-7-yl]benzamide Obtained as a beige solid (50%) from Intermediate 35 and Intermediate 12 following the experimental procedure described for the synthesis of Example 1.

LRMS (m/z): 421 (M+1)+.

1H-NMR δ (CDCl3): 0.63 (brs, 2H), 0.80-0.96 (m, 2H), 1.93 (s, 6H), 2.27 (s, 3H), 2.81-2.99 (m, 1H), 6.33 (brs, 1H), 6.85 (d, J=7.1 Hz, 1H), 7.41-7.56 (m, 2H), 7.72 (s, 1H), 8.32 (d, J=7.4 Hz, 1H).

Example 50

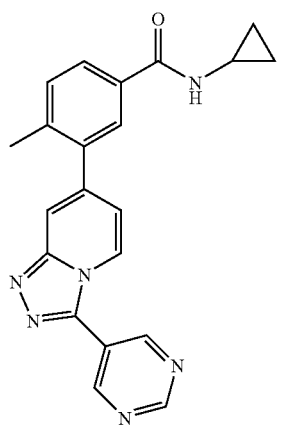

N-Cyclopropyl-4-methyl-3-(3-pyrimidin-5-yl[1,2,4]triazolo[4,3-a]pyridin-7-yl)benzamide Obtained as a solid (22%) from Intermediate 36 and Intermediate 11 following the experimental procedure described for the synthesis of Example 1.

LRMS (m/z): 371 (M+1)+.

1H-NMR δ (CDCl3): 0.54-0.73 (m, 2H), 0.80-0.99 (m, 2H), 2.37 (s, 3H), 2.80-3.05 (m, 1H), 6.66 (s, 1H), 7.03 (d, J=8.5 Hz, 1H), 7.37 (d, J=8.0 Hz, 1H), 7.65-7.85 (m, 3H), 8.33 (d, J=7.1 Hz, 1H), 9.31 (s, 2H), 9.40 (s, 1H).

Example 51

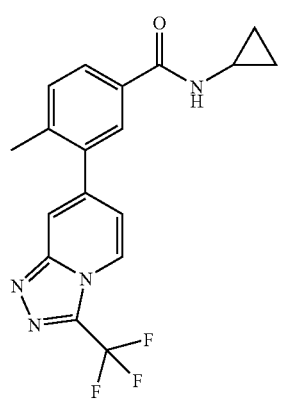

N-Cyclopropyl-4-methyl-3-[3-(trifluoromethyl)[1,2,4]triazolo[4,3-a]pyridin-7-yl]benzamide Obtained as a beige solid (22%) from Intermediate 27 and Intermediate 11 following the experimental procedure described for the synthesis of Example 1.

LRMS (m/z): 361 (M+1)+.

1H-NMR δ (CDCl3): 0.64 (brs, 2H), 0.86 (brs, 2H), 2.36 (s, 3H), 2.91 (brs, 1H), 6.74 (brs, 2H), 7.11 (d, J=6.9 Hz, 1H), 7.37 (d, J=8.0 Hz, 1H), 7.68-7.88 (m, 2H), 8.27 (d, J=6.6 Hz, 1H).

Example 52

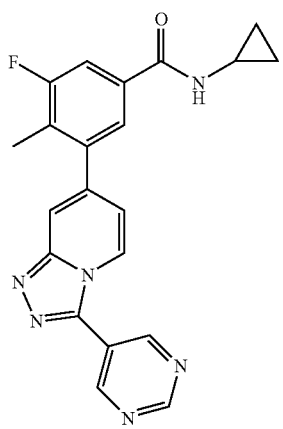

N-Cyclopropyl-3-fluoro-4-methyl-5-(3-pyrimidin-5-yl[1,2,4]triazolo[4,3-a]pyridin-7-yl)benzamide Obtained as a solid (34%) from Intermediate 36 and Intermediate 12 following the experimental procedure described for the synthesis of Example 1.
LRMS (m/z): 389 (M+1)+.
$^1$H-NMR δ (CDCl$_3$): 0.57-0.76 (m, 2H), 0.81-1.00 (m, 2H), 2.29 (s, 3H), 2.81-3.05 (m, 1H), 6.39 (s, 1H), 7.00 (d, J=7.1 Hz, 1H), 7.44-7.63 (m, 2H), 7.80 (s, 1H), 8.33 (d, J=7.4 Hz, 1H), 9.32 (s, 2H), 9.42 (s, 1H).

Example 53

7-{5-[(Cyclopropylamino)carbonyl]-3-fluoro-2-methylphenyl}[1,2,4]triazolo[4,3-a]pyridine-3-carboxamide Obtained as a white solid (20%) from Intermediate 37 and Intermediate 12 following the experimental procedure described for the synthesis of Example 1.
LRMS (m/z): 354 (M+1)+.
$^1$H-NMR δ (DMSO-d6): 0.46-0.62 (m, 2H), 0.64-0.79 (m, 2H), 2.25 (s, 3H), 2.86 (brs, 1H), 7.28 (d, J=7.1 Hz, 1H), 7.61-7.82 (m, 2H), 8.03 (s, 2H), 8.55 (brs, 2H), 9.27 (d, J=7.1 Hz, 1H).

The invention claimed is:
1. A compound of formula (I)

(I)

wherein
R$^1$ is chosen from C$_{1-4}$ alkyl, C$_{3-7}$ cycloalkyl, and —(CH$_2$)$_{(1-3)}$—C$_{3-7}$cycloalkyl;
R$^2$ is chosen from hydrogen and halogen atoms;
R$^3$ is chosen from methyl and halogen atoms;
L is a direct bond;
R$^4$ is chosen from C$_{1-4}$ alkyl, and C$_{3-6}$ cycloalkyl optionally substituted with methyl;
Y$^1$ and Y$^2$ are independently chosen from fluorine, and chlorine atoms;
or a pharmaceutically acceptable salt or a N-oxide thereof.
2. A compound according to claim 1, wherein R$^1$ is chosen from C$_{3-6}$ cycloalkyl and —(CH$_2$)$_{(1-3)}$—C$_{3-6}$ cycloalkyl.
3. A compound according to claim 2, wherein R$^1$ is a C$_{3-4}$ cycloalkyl.
4. A compound according to claim 1, wherein R$^2$ is chosen from hydrogen and fluorine.
5. A compound according to claim 1, wherein R$^3$ is methyl.
6. A compound according to claim 1, wherein R$^4$ is chosen from branched C$_{3-4}$ alkyl.
7. A compound according to claim 1, wherein Y$^1$ and Y$^2$ are each a fluorine atom.
8. A compound according to claim 1, wherein R$^1$ is cyclopropyl, R$^2$ is chosen from hydrogen and fluorine, R$^3$ is methyl, L is a direct bond, R$^4$ is chosen from branched C$_{3-4}$ alkyl, and Y$^1$ and Y$^2$ are each a fluorine atom.
9. A compound chosen from:
N-Cyclopropyl-3-(3-cyclopropyl-[1,2,4]triazolo[4,3-a]pyridin-7-yl)-4-methylbenzamide;
N-Cyclopropyl-4-methyl-3-(3-(1-methylcyclopropyl)-[1,2,4]triazolo[4,3-a]pyridin-7-yl)benzamide;
3-(3-Cyclobutyl-[1,2,4]triazolo[4,3-a]pyridin-7-yl)-N-cyclopropyl-4-methylbenzamide;
3-(3-tert-Butyl-[1,2,4]triazolo[4,3-a]pyridin-7-yl)-N-(cyclopropylmethyl)-4-methylbenzamide;
3-(3-tert-Butyl-[1,2,4]triazolo[4,3-a]pyridin-7-yl)-N-cyclopropyl-5-fluoro-4-methylbenzamide;
3-(3-tert-Butyl-[1,2,4]triazolo[4,3-a]pyridin-7-yl)-4-chloro-N-cyclopropylbenzamide;
3-(3-tert-Butyl-6-fluoro-[1,2,4]triazolo[4,3-a]pyridin-7-yl)-N-cyclopropyl-4-methylbenzamide;
3-(3-tert-Butyl-6-fluoro-[1,2,4]triazolo[4,3-a]pyridin-7-yl)-N-cyclopropyl-5-fluoro-4-methylbenzamide;
3-(3-tert-Butyl-6,8-difluoro-[1,2,4]triazolo[4,3-a]pyridin-7-yl)-N-cyclopropyl-4-methylbenzamide;
3-(3-tert-Butyl-6,8-difluoro-[1,2,4]triazolo[4,3-a]pyridin-7-yl)-N-cyclopropyl-5-fluoro-4-methylbenzamide;
N-Cyclopropyl-3-(6,8-difluoro-3-isopropyl[1,2,4]triazolo[4,3-a]pyridin-7-yl)-5-fluoro-4-methylbenzamide;
N-cyclopropyl-3-(3-cyclopropyl-6,8-difluoro[1,2,4]triazolo[4,3-a]pyridin-7-yl)-5-fluoro-4-methylbenzamide;
N-cyclopropyl-3-(3-cyclopropyl[1,2,4]triazolo[4,3-a]pyridin-7-yl)-5-fluoro-4-methylbenzamide;
N-cyclopropyl-3-fluoro-5-(3-isopropyl[1,2,4]triazolo[4,3-a]pyridin-7-yl)-4-methylbenzamide;
3-(3-Cyclobutyl[1,2,4]triazolo[4,3-a]pyridin-7-yl)-N-cyclopropyl-5-fluoro-4-methylbenzamide;
3-(3-Cyclohexyl[1,2,4]triazolo[4,3-a]pyridin-7-yl)-N-cyclopropyl-5-fluoro-4-methylbenzamide; and
N-Cyclopropyl-3-fluoro-4-methyl-5-[3-(1-methylcyclopropyl)[1,2,4]triazolo[4,3-a]pyridin-7-yl]benzamide;
or a pharmaceutically acceptable salt or a N-oxide thereof.
10. A pharmaceutical composition comprising a compound according to claim 1 and a pharmaceutically acceptable diluent or carrier.
11. A combination product comprising:
(i) a compound according to claim 1; and
(ii) another compound chosen from (1) antagonists of M3 muscarinic receptors, (2) β2-agonists, (3) PDE4 inhibitors, (4) corticosteroids, (5) leukotriene D4 antagonists, (6) inhibitors of egfr-kinase, (7) antagonists of the A2B adenosine receptor, (8) NK1 receptor agonists, (9) CRTh2 antagonists, (10) syk kinase inhibitors, (11) CCR3 antagonists, (12) VLA-4 antagonists, and (13) a DMARD (disease modifying antirheumatic drug) for simultaneous, separate or sequential use in the treatment of the human or animal body.

12. A compound of formula (I)

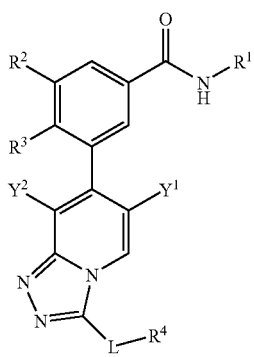

wherein
R¹ is chosen from $C_{1-4}$ alkyl, $C_{3-7}$ cycloalkyl, and —$(CH_2)_{(1-3)}$—$C_{3-7}$cycloalkyl;
R² is chosen from hydrogen and halogen atoms;
R³ is chosen from methyl and halogen atoms;
L is a direct bond;
R⁴ is chosen from methyl, and $C_{3-6}$ cycloalkyl optionally substituted with methyl;
Y¹ and Y² are independently chosen from hydrogen, fluorine, and chlorine atoms;
or a pharmaceutically acceptable salt or a N-oxide thereof;
with the proviso that the compound of formula (I) is not N-Cyclopropyl-3-(3-isopropyl-[1,2,4]triazolo[4,3-a]pyridin-7-yl)-4-methylbenzamide.

* * * * *